US012390519B2

(12) United States Patent
Moser et al.

(10) Patent No.: US 12,390,519 B2
(45) Date of Patent: Aug. 19, 2025

(54) INFLUENZA B VIRUS MUTANTS AND USES THEREFOR

(71) Applicant: FluGen, Inc., Madison, WI (US)

(72) Inventors: Michael J. Moser, Madison, WI (US); Yasuko Hatta, Madison, WI (US); Pamuk Bilsel, Madison, WI (US)

(73) Assignee: FluGen, Inc., Madison, WI (US)

( * ) Notice: Subject to any disclaimer, the term of this patent is extended or adjusted under 35 U.S.C. 154(b) by 0 days.

(21) Appl. No.: 18/074,220

(22) Filed: Dec. 2, 2022

(65) Prior Publication Data

US 2024/0091337 A1 Mar. 21, 2024

Related U.S. Application Data

(62) Division of application No. 16/488,913, filed as application No. PCT/US2018/019690 on Feb. 26, 2018, now Pat. No. 11,529,409.

(60) Provisional application No. 62/463,994, filed on Feb. 27, 2017.

(51) Int. Cl.
*C12N 7/00* (2006.01)
*A61K 39/145* (2006.01)
*A61K 39/39* (2006.01)
*C07K 14/005* (2006.01)

(52) U.S. Cl.
CPC ............ *A61K 39/145* (2013.01); *A61K 39/39* (2013.01); *C07K 14/005* (2013.01); *C12N 7/00* (2013.01); *C12N 2760/16121* (2013.01); *C12N 2760/16122* (2013.01); *C12N 2760/16134* (2013.01); *C12N 2760/16161* (2013.01); *C12N 2760/16221* (2013.01); *C12N 2760/16222* (2013.01); *C12N 2760/16234* (2013.01); *C12N 2760/16261* (2013.01)

(58) Field of Classification Search
None
See application file for complete search history.

(56) References Cited

U.S. PATENT DOCUMENTS

2010/0322970 A1  12/2010  Kittel et al.

FOREIGN PATENT DOCUMENTS

| CN | 101903043 | 12/2010 | |
|---|---|---|---|
| EP | 2 072 058 A1 | 6/2009 | |
| JP | 2011-505863 | 3/2011 | |
| WO | WO-2012177924 A2 * | 12/2012 | ............ A61K 35/76 |
| WO | WO-2015/142671 A2 | 9/2015 | |

OTHER PUBLICATIONS

Hatta et al., "Influenza B Virus Requires BM2 Protein for Replication," Journal of Virology, vol. 78, No. 11: 5576-5583 (Year: 2004).*

(Continued)

*Primary Examiner* — M Franco G Salvoza
(74) *Attorney, Agent, or Firm* — Foley & Lardner LLP

(57) ABSTRACT

Disclosed herein are compositions and methods related to mutant viruses, and in particular, mutant influenza viruses. The mutant viruses disclosed herein include a mutant BM2 sequence, and are useful in immunogenic compositions, e.g., as vaccines. Also disclosed herein are methods, compositions and cells for propagating the viral mutants, and methods, devices and compositions related to vaccination.

7 Claims, 28 Drawing Sheets
Specification includes a Sequence Listing.

(56) References Cited

OTHER PUBLICATIONS

Wanitchang et al., "Influenza V virus M2 protein can functionally replace its influenza A virus counterpart in promoting virus replication," Virology 498: 99-108 (Year: 2016).*
"Genbank", CY115136.1, 2012.
Database GenBank [online], Accession No. CY033877.1, Jul. 21, 2008 accessed Sep. 16, 2022.
Hatta et al. "Influenza B Virus Requires BM2 Protein for Replication," Journal of Virology, vol. 78, No. 11 (2004) (pp. 5576-5583).
Imai et al. "Influenza B Virus BM2 Protein Is a Crucial Component for Incorporation of Viral Ribonucleoprotein Complex into Virions during Virus Assembly," Journal of Virology, 2004, vol. 78, No. 20, p. 11007-1101.
Imai, "Cytoplasmic Domain of Influenza B Virus BM2 Protein Plays Critical Roles in Production of Infectious Virus," Journal of Virology, Jan. 2008, vol. 82, No. 2, pp. 728-739.
International Preliminary Report on Patentability in International Application No. PCT/US2018/019690 mailed on Sep. 6, 2019 (8 pages).
International Search Report and Written Opinion in International Application PCT/US2018/019690 mailed on Jul. 12, 2018 (35 pages).
Ohigashi, et al., "An amantadine-sensitive chimeric BM2 ion channel of influenza B virus has implications for the mechanism of drug inhibition," PNAS, Nov. 3, 2009, vol. 106, No. 44, pp. 18775-18779.
Watanabe, et al., "Influenza A Virus Lacking M2 Protein as a Live Attenuated Vaccine," Journal of Virology, Jun. 2009, vol. 83, No. 11, pp. 5947-5950.

\* cited by examiner

FIG. 2

TCID$_{50}$ Titration FluA and FluB M2SR Virus M2CK vs. BM2CK Cell Substrate

FIG. 9

BM2 protein evolution

- B/Maryland/23/2015
- B/Wisconsin/17/2016
- B/Florida/14/2016
- B/Auckland/501/2013
- B/Brisbane/74/2012
- B/Brisbane/1/2007
- B/Colorado/13/2004
- B/Florida/4/2006
- B/South Dakota/12/2016
- B/Christchurch/25/2011
- B/Brisbane/39/2010
- B/Townsville/9/2002
- B/Christchurch/90/2002
- B/Temple/B3/1999
- B/Yamanashi/166/1998
- B/Chile/3162/2002
- B/New York/1007/1995
- B/Hong Kong/03/1992
- B/Memphis/3/89
- B/Texas/37/1988
- B/Ann Arbor/1/1966 [wild-type]
- B/Lee/1940

Wild-type & BM2SR4 B/CA/12/2015
AOF Virus Growth – Vero Cell Lines

SEQUENCE LISTING

```
Sequence total quantity: 37
SEQ ID NO: 1            moltype = DNA  length = 861
FEATURE                 Location/Qualifiers
source                  1..861
                        mol_type = other DNA
                        organism = synthetic construct
SEQUENCE: 1
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaaacaa aagatgctta   180
actgacatac agaaagcact aattggcgcc tctatctgct ttttaaaacc caaagaccag   240
gaaagaaaaa gaagattcat cacagagccc ctatcaggaa tggggacaac agcaacaaaa   300
aagaagggcc tgattctagc tgagagaaaa atgagaagat gtgtgagctt ccatgaagca   360
tttgaaatag cagaaggcca tgaaagctca gcgttactat attgtctcat ggtcatgtac   420
ctgaatcctg gaaattattc aatgcaagta aaactaggaa cgctctgtgc tttgtgcgaa   480
aaacaagcat cacattcaca cagggctcat agcagagcag cgagatcttc agtgcctgga   540
gtgagacggg aaatgcagat ggtctcagct atgaacacag caaaaacaat gaatggaatg   600
ggaaaaggag aagacgttca aaaactggca gaagaactgc aaagcaacat tggagtattg   660
agatctcttg gggcaagtca aaagaatggg gaaggaattg caaaggatgt aatggaagtg   720
ctaaagcaga gctctatggg aaattcagct cttgtgaaga aataccctata aattcaattt   780
ttactgtact tcttactatg catttaagca aattgtaatc aatgtcagca aataaactgg   840
aaaaagtgcg ttgtttctac t                                             861

SEQ ID NO: 2            moltype = DNA  length = 904
FEATURE                 Location/Qualifiers
source                  1..904
                        mol_type = other DNA
                        organism = synthetic construct
```

SEQUENCE: 2
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaacaa aagatgctta   180
actgacatac agaaagcact aattggcgcc tctatctgct ttttaaaacc caaagaccag   240
gaaagaaaaa gaagattcat cacagagccc ctatcaggaa tggggacaac agcaacaaaa   300
aagaagggcc tgattctagc tgagagaaaa atgagaagat gtgtgagctt ccatgaagca   360
tttgaaaatag cagaaggcca tgaaagctca gcgttactat attgtctcat ggtcatgtac   420
ctgaatcctg gaaattattc aatgcaagta aaactaggaa cgctctgtgc tttgtgcgaa   480
aaacaagcat cacattcaca cagggctcat agcagagca cgagatcttc agtgcctgga   540
gtgagacggg aaatgcagat ggtctcagct atgaacacag caaaaacaat gaatggaatg   600
ggaaaaggag aagacgttca aaaactggca gaagaactgc aaagcaacat tggagtattg   660
agatctcttg gggcaagtca aaagaatggg gaaggaattg caaggatgt aatggaagtg   720
ctaaagcaga gctctatggg aaattcagct cttgtgaaga aatacctata atgctcgaac   780
catttcagat tctttcaatt tgttagatag ctaaattcaa ttttttactgt acttcttact   840
atgcatttaa gcaaattgta atcaatgtca gcaaataaac tggaaaaagt gcgttgtttc   900
tact                                                              904

SEQ ID NO: 3          moltype = DNA   length = 904
FEATURE               Location/Qualifiers
source                1..904
                      mol_type = other DNA
                      organism = synthetic construct
SEQUENCE: 3
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaacaa aagatgctta   180
actgacatac agaaagcact aattggcgcc tctatctgct ttttaaaacc caaagaccag   240
gaaagaaaaa gaagattcat cacagagccc ctatcaggaa tggggacaac agcaacaaaa   300
aagaagggcc tgattctagc tgagagaaaa atgagaagat gtgtgagctt ccatgaagca   360
tttgaaaatag cagaaggcca tgaaagctca gcgttactat attgtctcat ggtcatgtac   420
ctgaatcctg gaaattattc aatgcaagta aaactaggaa cgctctgtgc tttgtgcgaa   480
aaacaagcat cacattcaca cagggctcat agcagagcg cgagatcttc agtgcctgga   540
gtgagacggg aaatgcagat ggtctcagct atgaacacag caaaaacaat gaatggaatg   600
ggaaaaggag aagacgttca aaaactggca gaagaactgc aaagcaacat tggagtattg   660
agatctcttg gggcaagtca aaagaatggg gaaggaattg caaggatgt aatggaagtg   720
ctaaagcaga gctctatggg aaattcagct cttgtgaaga aatacctata atgctcgaac   780
catttcagat tctttcaatt tgttagatag ctaaattcaa ttttttactgt acttcttact   840
atgcatttaa gcaaattgta atcaatgtca gcaaataaac tggaaaaagt gcgttgtttc   900
tact                                                              904

SEQ ID NO: 4          moltype = DNA   length = 1111
FEATURE               Location/Qualifiers
source                1..1111
                      mol_type = other DNA
                      organism = synthetic construct
SEQUENCE: 4
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaacaa aagatgctta   180
actgacatac agaaagcact aattggcgcc tctatctgct ttttaaaacc caaagaccag   240
gaaagaaaaa gaagattcat cacagagccc ctatcaggaa tggggacaac agcaacaaaa   300
aagaagggcc tgattctagc tgagagaaaa atgagaagat gtgtgagctt ccatgaagca   360
tttgaaaatag cagaaggcca tgaaagctca gcgttactat attgtctcat ggtcatgtac   420
ctgaatcctg gaaattattc aatgcaagta aaactaggaa cgctctgtgc tttgtgcgaa   480
aaacaagcat cacattcaca cagggctcat agcagagcg cgagatcttc agtgcctgga   540
gtgagacggg aaatgcagat ggtctcagct atgaacacag caaaaacaat gaatggaatg   600
ggaaaaggag aagacgttca aaaactggca gaagaactgc aaagcaacat tggagtattg   660
agatctcttg gggcaagtca aaagaatggg gaaggaattg caaggatgt aatggaagtg   720
ctaaagcaga gctctatggg aaattcagct cttgtgaaga aatacctata atgctcgaac   780
catttcagat tctttcaatt tgttagatag ctaaaggggg ccaaataaag agacaataaa   840
cagagaggta tcaattttga gacacagtta ccaaaaagaa atccaggcca aagaagcaat   900
gaaggaagta ctctctgaca acatggaggt attgagtgac cacatagtaa ttgaggggct   960
ttctgctgaa gataataa aaatgggtga aacagttttg gaggtagaag aattgcatta  1020
aattcaattt ttactgtact tcttactatg catttaagca aattgtaatc aatgtcagca  1080
aataaactgg aaaaagtgcg ttgtttctac t                                1111

SEQ ID NO: 5          moltype = DNA   length = 1111
FEATURE               Location/Qualifiers
source                1..1111
                      mol_type = other DNA
                      organism = synthetic construct
SEQUENCE: 5
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaacaa aagatgctta   180
actgacatac agaaagcact aattggcgcc tctatctgct ttttaaaacc caaagaccag   240
gaaagaaaaa gaagattcat cacagagccc ctatcaggaa tggggacaac agcaacaaaa   300
aagaagggcc tgattctagc tgagagaaaa atgagaagat gtgtgagctt ccatgaagca   360

```
tttgaaatag cagaaggcca tgaaagctca gcgttactat attgtctcat ggtcatgtac    420
ctgaatcctg gaaattattc aatgcaagta aaactaggaa cgctctgtgc tttgtgcgaa    480
aaacaagcat cacattcaca cagggctcat agcagagcag cgagatcttc agtgcctgga    540
gtgagacggg aaatgcagat ggtctcagct atgaacacag caaaaacaat gaatggaatg    600
ggaaaaggag aagacgttca aaaactggca gaagaactgc aaagcaacat tggagtattg    660
agatctcttg ggcaagtca aaagaatggg aaggaattg caaaggatgt aatggaagtg    720
ctaaagcaga gctctatggg aaattcagct cttgtgaaga atacctata atgctcgaac    780
catttcagat tctttcaatt tgttagatag ctaaaggggg ccaaataaag agacaataaa    840
cagagaggta tcaattttga gacacagtta ccaaaaagaa atccaggcca aagaagcaat    900
gaaggaagta ctctctgaca acatggaggt attgagtgac cacatagtaa ttgagggct    960
ttctgctgaa gagataataa aatgggtga aacagttttg gaggtagaag aattgcatta   1020
aattcaattt ttactgtact tcttactatg catttaagca aattgtaatc aatgtcagca   1080
aataaactgg aaaaagtgcg ttgtttctac t                                  1111

SEQ ID NO: 6            moltype = DNA  length = 862
FEATURE                 Location/Qualifiers
source                  1..862
                        mol_type = other DNA
                        organism = synthetic construct
SEQUENCE: 6
agcagaagca cgcactttct taaaatgtcg ctgtttggag acacaattgc ctacctgctt     60
tcactaatag aagatggaga aggcaaagca gaactagctg aaaaattaca ctgttggttc    120
ggtgggaaag aatttgacct agattctgct ttggaatgga taaaaaacaa aaggtgccta    180
actgatatac aaaaagcact aattggtgcc tctatatgct ttttaaaacc caaagaccaa    240
gaaagaaaaa ggagattcat cacagagccc ctgtcaggaa tgggaacaac agcaacaaag    300
aagaaaggcc taattctagc tgagagaaaa atgagaagat gtgtaagctt tcatgaagca    360
tttgaaatag cagaaggcca cgaaagctca gcattactat attgtcttat ggtcatgtac    420
ctaaaccctg aaaactattc aatgcaagta aaactaggaa cgctctgtgc tttatgcgag    480
aaacaagcat cgcactcgca tagagcccat agcagagcag caaggtcttc ggtacctgga    540
gtaagacgag aaatgcagat ggtttcagct atgaacacag caaagacaat gaatggaatg    600
ggaaagggag aagacgtcca aaaactagca gaagagctgc aaaacaacat tggagtgttg    660
agatctctag gagcaagtca aaagaatgga gaaggaattg ccaaagatgt aatggaagtg    720
ctaaaacaga gctctatggg aaattcagct cttgtgagga atacttata gcccaatttt    780
tcactgtatt tcttactatg catttaagca aattgtaatc aatgtcagtg aataaactg    840
gaaaaagtgc gttgtttcta ct                                             862

SEQ ID NO: 7            moltype = DNA  length = 1191
FEATURE                 Location/Qualifiers
source                  1..1191
                        mol_type = other DNA
                        organism = unidentified
SEQUENCE: 7
agcagaagca cgcactttct taaaatgtcg ctgtttggag acacaattgc ctacctgctt     60
tcactaatag aagatggaga aggcaaagca gaactagctg aaaaattaca ctgttggttc    120
ggtgggaaag aatttgacct agattctgct ttggaatgga taaaaaacaa aaggtgccta    180
actgatatac aaaaagcact aattggtgcc tctatatgct ttttaaaacc caaagaccaa    240
gaaagaaaaa ggagattcat cacagagccc ctgtcaggaa tgggaacaac agcaacaaag    300
aagaaaggcc taattctagc tgagagaaaa atgagaagat gtgtaagctt tcatgaagca    360
tttgaaatag cagaaggcca cgaaagctca gcattactat attgtcttat ggtcatgtac    420
ctaaaccctg aaaactattc aatgcaagta aaactaggaa cgctctgtgc tttatgcgag    480
aaacaagcat cgcactcgca tagagcccat agcagagcag caaggtcttc ggtacctgga    540
gtaagacgag aaatgcagat ggtttcagct atgaacacag caaagacaat gaatggaatg    600
ggaaagggag aagacgtcca aaaactagca gaagagctgc aaaacaacat tggagtgttg    660
agatctctag gagcaagtca aaagaatgga gaaggaattg ccaaagatgt aatggaagtg    720
ctaaaacaga gctctatggg aaattcagct cttgtgagga atacttata atgctcgaac    780
cacttcagat tctttcaatt tgttcttca ttttatcagc tctccattc atggcttga    840
caatagggca tttgaatcaa ataagaagag ggtaaacct gaaatacaa ataaggaatc    900
caaataagga ggcaataaac agagaggtgt caattctgag acacaattac caaaaggaaa    960
tccaagccaa agaaacaatg aagaaaatac tctctgacaa catggaagta ttgggtgacc   1020
acatagtagt tgaagggctt tcaactgatg ataataaa atgggtgaa acagttttgg   1080
aggtggaaga attgcaatga gcccaatttt cactgtattt cttactatgc atttaagcaa   1140
attgtaatca atgtcagtga ataaaactgg aaaaagtgcg ttgtttctac t             1191

SEQ ID NO: 8            moltype = AA  length = 248
FEATURE                 Location/Qualifiers
source                  1..248
                        mol_type = protein
                        organism = unidentified
SEQUENCE: 8
MSLFGDTIAY LLSLIEDGEG KAELAEKLHC WFGGKEFDLD SALEWIKNKR CLTDIQKALI     60
GASICFLKPK DQERKRRFIT EPLSGMGTTA TKKKGLILAE RKMRRCVSFH EAFEIAEGHE    120
SSALLYCLMV MYLNPENYSM QVKLGTLCAL CEKQASHSHR AHSRAARSSV PGVRREMQMV    180
SAMNTAKTMN GMGKGEDVQK LAEELQNNIG VLRSLGASQK NGEGIAKDVM EVLKQSSMGN    240
SALVRKYL                                                             248

SEQ ID NO: 9            moltype = AA  length = 248
FEATURE                 Location/Qualifiers
source                  1..248
                        mol_type = protein
```

```
                        organism = unidentified
SEQUENCE: 9
MSLFGDTIAY LLSLTEDGEG KAELAEKLHC WFGGKEFDLD SALEWIKNKR CLTDIQKALI    60
GASICFLKPK DQERKRRFIT EPLSGMGTTA TKKKGLILAE RKMRRCVSFH EAFEIAEGHE   120
SSALLYCLMV MYLNPGNYSM QVKLGTLCAL CEKQASHSHR AHSRAARSSV PGVRREMQMV   180
SAMNTAKTMN GMGKGEDVQK LAEELQSNIG VLRSLGASQK NGEGIAKDVM EVLKQSSMGN   240
SALVKKYL                                                           248

SEQ ID NO: 10           moltype = AA   length = 248
FEATURE                 Location/Qualifiers
source                  1..248
                        mol_type = protein
                        organism = unidentified
SEQUENCE: 10
MSLFGDTIAY LLSLTEDGEG KAELAEKLHC WFGGKEFDLD SALEWIKNKR CLTDIQKALI    60
GASICFLKPK DQERKRRFIT EPLSGVGTTA TKKKGLILAE RKMRRCVSFH EAFEIAEGHE   120
SSALLYCLMV MYLNPGNYSM QVKLGTLCAL CEKQASHSHR AHSRAARSSV PGVRREMQMV   180
SAMNTAKTMN GMGKGEDVQK LAEELQSNIG VLRSLGASQK NGEGIAKDVM EVLKQSSMGN   240
SALVKKYL                                                           248

SEQ ID NO: 11           moltype = AA   length = 109
FEATURE                 Location/Qualifiers
source                  1..109
                        mol_type = protein
                        organism = unidentified
SEQUENCE: 11
MLEPLQILSI CSFILSALHF MAWTIGHLNQ IRRGVNLKIQ IRNPNKEAIN REVSILRHNY    60
QKEIQAKETM KKILSDNMEV LGDHIVVEGL STDEIIKMGE TVLEVEELQ              109

SEQ ID NO: 12           moltype = AA   length = 109
FEATURE                 Location/Qualifiers
source                  1..109
                        mol_type = protein
                        organism = unidentified
SEQUENCE: 12
MLEPFQILSI CSFILSALHF VAWTIGHLNQ IKRGVNMKIR IKGPNKETIN REVSILRHSY    60
QKEIQAKEAM KEVLSDNMEV LSDHIVIEGL SAEEIIKMGE TVLEVEELH              109

SEQ ID NO: 13           moltype = DNA   length = 421
FEATURE                 Location/Qualifiers
source                  1..421
                        mol_type = other DNA
                        organism = unidentified
SEQUENCE: 13
atgctcgaac cacttcagat tctttcaatt tgttctttca ttttatcagc tctccatttc    60
atggcttgga caatagggca tttgaatcaa ataagaagag gggtaaacct gaaaatacaa   120
ataagaatca caaataagga ggcaataaac agagaggtgt caattctgag acacaattac   180
caaaaggaaa tccaagccaa agaaacaatg aagaaaatac tctctgacaa catggaagta   240
ttgggtgacc acatagtagt tgaagggctt tcaactgatg agataataaa atgggtgaa   300
acagttttgg aggtggaaga attgcaatga gcccaatttt cactgtattt cttactatgc   360
atttaagcaa attgtaatca atgtcagtga ataaactgg aaaaagtgcg ttgtttctac   420
t                                                                  421

SEQ ID NO: 14           moltype = AA   length = 97
FEATURE                 Location/Qualifiers
source                  1..97
                        mol_type = protein
                        organism = unidentified
SEQUENCE: 14
MSLLTEVETP IRNEWGCRCN GSSDPLTIAA NIIGILHLTL WILDRLFFKC IYRRFKYGLK    60
GGPSTEGVPK SMREEYRKEQ QSAVDADDGH FVSIELE                             97

SEQ ID NO: 15           moltype = AA   length = 109
FEATURE                 Location/Qualifiers
source                  1..109
                        mol_type = protein
                        organism = unidentified
SEQUENCE: 15
MLEPLQILSI CSFILSALHF MAWTIGHLNQ IRRGVNLKIQ IRNPNKEAIN REVSILRHNY    60
QKEIQAKETM KKILSDNMEV LGDHIVVEGL STDEIIKMGE TVLEVEELQ              109

SEQ ID NO: 16           moltype = AA   length = 109
FEATURE                 Location/Qualifiers
source                  1..109
                        mol_type = protein
                        organism = unidentified
SEQUENCE: 16
MLEPLQILSI CSFILSALCF MAWTIGHLNQ IRRGVNLKIQ IRNPNKEAIN REVSILRHNY    60
QKEIQAKETM KKILSDNMEV LGDHIVVEGL STDEIIKMGE TVLEVEELQ              109
```

```
SEQ ID NO: 17            moltype = AA   length = 127
FEATURE                  Location/Qualifiers
source                   1..127
                         mol_type = protein
                         organism = synthetic construct
SEQUENCE: 17
MSLLTEVETP IRNEWGCRCN GSSDPLSICS FILSALHFMA WTIGHLNQIR RGVNLKIQIR    60
NPNKEAINRE VSILRHNYQK EIQAKETMKK ILSDNMEVLG DHIVVEGLST DEIIKMGETV   120
LEVEELQ                                                            127

SEQ ID NO: 18            moltype = AA   length = 127
FEATURE                  Location/Qualifiers
source                   1..127
                         mol_type = protein
                         organism = synthetic construct
SEQUENCE: 18
MSLLTEVETP IRNEWGCRCN GSSDPLTIAA NIIGILHLTL WILDRLNQIR RGVNLKIQIR    60
NPNKEAINRE VSILRHNYQK EIQAKETMKK ILSDNMEVLG DHIVVEGLST DEIIKMGETV   120
LEVEELQ                                                            127

SEQ ID NO: 19            moltype = AA   length = 127
FEATURE                  Location/Qualifiers
source                   1..127
                         mol_type = protein
                         organism = synthetic construct
SEQUENCE: 19
MSLLTEVETP IRNEWGCRCN GSSDPLTIAA NIIGILHFMA WTIGHLNQIR RGVNLKIQIR    60
NPNKEAINRE VSILRHNYQK EIQAKETMKK ILSDNMEVLG DHIVVEGLST DEIIKMGETV   120
LEVEELQ                                                            127

SEQ ID NO: 20            moltype = AA   length = 109
FEATURE                  Location/Qualifiers
source                   1..109
                         mol_type = protein
                         organism = synthetic construct
SEQUENCE: 20
MLEPLQILTI AANIIGILHL TLWILDRLNQ IRRGVNLKIQ IRNPNKEAIN REVSILRHNY    60
QKEIQAKETM KKILSDNMEV LGDHIVVEGL STDEIIKMGE TVLEVEELQ              109

SEQ ID NO: 21            moltype = AA   length = 79
FEATURE                  Location/Qualifiers
source                   1..79
                         mol_type = protein
                         organism = synthetic construct
SEQUENCE: 21
MLEPLQILSI CSFILSALHF MAWTIGHLFF KCIYRRFKYG LKGGPSTEGV PKSMREEYRK    60
EQQSAVDADD GHFVSIELE                                                79

SEQ ID NO: 22            moltype = AA   length = 109
FEATURE                  Location/Qualifiers
source                   1..109
                         mol_type = protein
                         organism = synthetic construct
SEQUENCE: 22
MLEPLQILTI AANIIGILHF MAWTIGHLNQ IRRGVNLKIQ IRNPNKEAIN REVSILRHNY    60
QKEIQAKETM KKILSDNMEV LGDHIVVEGL STDEIIKMGE TVLEVEELQ              109

SEQ ID NO: 23            moltype = DNA  length = 294
FEATURE                  Location/Qualifiers
source                   1..294
                         mol_type = other DNA
                         organism = unidentified
SEQUENCE: 23
atgagtcttc taaccgaggt cgaaacgcct atcagaaacg aatggggtg cagatgcaac     60
ggttcaagtg atcctctcac tattgccgca aatatcattg gatcttgca cttgacattg   120
tggattcttg atcgtctttt tttcaaatgc atttaccgtc gctttaaata cggactgaaa   180
ggagggcctt ctacggaagg agtgccaaag tctatgaggg agaatatcg aaaggaacag   240
cagagtgctg tggatgctga cgatggtcat tttgtcagca tagagctgga gtaa         294

SEQ ID NO: 24            moltype = DNA  length = 330
FEATURE                  Location/Qualifiers
source                   1..330
                         mol_type = other DNA
                         organism = unidentified
SEQUENCE: 24
atgctcgaac cacttcagat tcttttcaatt tgttctttca ttttatcagc tctccatttc    60
atggcttgga caatagggca tttgaatcaa ataagaagag gggtaaacct gaaaatacaa   120
ataaggaatc caaataagga ggcaataaac agagaggtgt caattctgag acacaattac   180
```

```
caaaaggaaa tccaagccaa agaaacaatg aagaaaatac tctctgacaa catggaagta    240
ttgggtgacc acatagtagt tgaagggctt tcaactgatg agataataaa aatgggtgaa    300
acagttttgg aggtggaaga attgcaataa                                     330

SEQ ID NO: 25          moltype = DNA  length = 330
FEATURE                Location/Qualifiers
source                 1..330
                       mol_type = other DNA
                       organism = unidentified
SEQUENCE: 25
atgctcgaac acttcagat tctttcaatt tgtcttttca ttttatcagc tctctgtttc    60
atggcttgga caatagggca tttgaatcaa ataagaagag gggtaaacct gaaaatacaa   120
ataaggaatc caaataagga ggcaataaac agagaggtgt caattctgag acacaattac   180
caaaaggaaa tccaagccaa agaaacaatg aagaaaatac tctctgacaa catggaagta   240
ttgggtgacc acatagtagt tgaagggctt tcaactgatg agataataaa aatgggtgaa   300
acagttttgg aggtggaaga attgcaataa                                    330

SEQ ID NO: 26          moltype = DNA  length = 294
FEATURE                Location/Qualifiers
source                 1..294
                       mol_type = other DNA
                       organism = synthetic construct
SEQUENCE: 26
atgtccctgc tgaccgaagt ggaaactcct attagaaacg agtggggctg tagatgtaac    60
ggctcaagcg accctctgac cattgctgcc aacatcattg gcatcctgca cctgaccctg   120
tggattctgg accgactgtt cttaagtgc atctaccgga gattcaagta tggactgaaa    180
ggaggaccaa gcacagaggg agtgcctaaa tccatgaggg aggaataccg caaagagcag   240
cagagcgccg tggacgcaga tgatggacat tcgtgagca ttgaactgga atga           294

SEQ ID NO: 27          moltype = DNA  length = 330
FEATURE                Location/Qualifiers
source                 1..330
                       mol_type = other DNA
                       organism = synthetic construct
SEQUENCE: 27
atgctggaac cactgcagat cctgagtatt tgctcttta tcctgagcgc actgcacttt     60
atggcctgga ctatcgggca cctgaaccag atcagaaggg gcgtgaacct gaagatccag   120
atcagaaacc caaacaagga ggccatcaac cgcgaagtga gcatcctgag acacaattac   180
cagaaggaga tccaggctaa agaaaccatg aagaaaatcc tgtctgacaa tatggaggtg   240
ctgggcgatc acatcgtggt ggaaggactg agcaccgacg aaatcatcaa aatgggcgag   300
actgtcctgg aagtggaaga actgcagtaa                                    330

SEQ ID NO: 28          moltype = DNA  length = 384
FEATURE                Location/Qualifiers
source                 1..384
                       mol_type = other DNA
                       organism = synthetic construct
SEQUENCE: 28
atgtccctgc tgaccgaagt ggaaactcct attagaaacg agtggggctg tagatgtaac    60
ggctcaagcg accctctgac cattgctgcc aacatcattg gcatcctgca cctgaccctg   120
tggattctgg accgactgaa ccagatcaga aggggcgtga acctgaagat ccagatcaga   180
aacccaaaca aggaggccat caaccgcgaa gtgagcatcc tgagacacaa ttaccagaag   240
gagatccagg ctaaagaaac catgaagaaa atcctgtctg acaatatgga ggtgctgggc   300
gatcacatcg tggtggaagg actgagcacc gacgaaatca tcaaaatggg cgagactgtc   360
ctggaagtgg aagaactgca gtaa                                          384

SEQ ID NO: 29          moltype = DNA  length = 384
FEATURE                Location/Qualifiers
source                 1..384
                       mol_type = other DNA
                       organism = synthetic construct
SEQUENCE: 29
atgtccctgc tgaccgaagt ggaaactcct attagaaacg agtggggctg tagatgtaac    60
ggctcaagcg accctctgac cattgctgcc aacatcattg gcatcctgca cctgaccctg   120
tggattctgg accgactgaa ccagatcaga aggggcgtga acctgaagat ccagatcaga   180
aacccaaaca aggaggccat caaccgcgaa gtgagcatcc tgagacacaa ttaccagaag   240
gagatccagg ctaaagaaac catgaagaaa atcctgtctg acaatatgga ggtgctgggc   300
gatcacatcg tggtggaagg actgagcacc gacgaaatca tcaaaatggg cgagactgtc   360
ctggaagtgg aagaactgca gtaa                                          384

SEQ ID NO: 30          moltype = DNA  length = 390
FEATURE                Location/Qualifiers
source                 1..390
                       mol_type = other DNA
                       organism = synthetic construct
SEQUENCE: 30
atgtccctgc tgaccgaagt ggaaactcct attagaaacg agtggggctg tagatgtaac    60
ggctcaagcg accctctgac cattgctgcc aacatcattg gcatcctgca cctgaccctg   120
tggattctgg accgactgtt cttaaccag atcagaaggg gcgtgaacct gaagatccag    180
```

```
atcagaaacc caaacaagga ggccatcaac cgcgaagtga gcatcctgag acacaattac    240
cagaaggaga tccaggctaa agaaaccatg aagaaaatcc tgtctgacaa tatggaggtg    300
ctgggcgatc acatcgtggt ggaaggactg agcaccgacg aaatcatcaa aatgggcgag    360
actgtcctgg aagtggaaga actgcagtaa                                    390

SEQ ID NO: 31           moltype = DNA  length = 330
FEATURE                 Location/Qualifiers
source                  1..330
                        mol_type = other DNA
                        organism = synthetic construct
SEQUENCE: 31
atgctcgaac cacttcagat tcttactatt gctgccaaca tcattggcat cctgcacctg     60
accctgtgga ttctggaccg actgaaccag atcagaaggg gcgtgaacct gaagatccag    120
atcagaaacc caaacaagga ggccatcaac cgcgaagtga gcatcctgag acacaattac    180
cagaaggaga tccaggctaa agaaaccatg aagaaaatcc tgtctgacaa tatggaggtg    240
ctgggcgatc acatcgtggt ggaaggactg agcaccgacg aaatcatcaa aatgggcgag    300
actgtcctgg aagtggaaga actgcagtaa                                    330

SEQ ID NO: 32           moltype = DNA  length = 240
FEATURE                 Location/Qualifiers
source                  1..240
                        mol_type = other DNA
                        organism = synthetic construct
SEQUENCE: 32
atgctggaac cactgcagat cctgagtatt tgctctttta tcctgagcgc actgcacttt     60
atggcctgga ctatcgggca cctgttcttt aagtgcatct accggagatt caagtgagcg    120
ctgaaaggag gaccaagcac agagggagtg cctaaatcca tgaggggagga ataccgcaaa    180
gagcagcaga gcgccgtgga cgcagatgat ggacatttcg tgagcattga actggaatga    240

SEQ ID NO: 33           moltype = DNA  length = 976
FEATURE                 Location/Qualifiers
source                  1..976
                        mol_type = other DNA
                        organism = synthetic construct
SEQUENCE: 33
agcaaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggtttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagtcc agtgctggtc tgaaaaatga    720
tcttcttgaa aatttgcagg cctatcagaa acgaatgggg gtgcagatgc aacggttcaa    780
gtgattaata ggatcgtctt ttttttcaaat gcatttaccg tcgctttaaa tacggactga    840
aaggaggggcc ttctacggaa ggagtgccaa agtctatgag gaagaatat cgaaaggaac    900
agcagagtgc tgtggatgct gacgatggtc atttttgtcag catagagctg gagtaaaaaa    960
ctaccttgtt tctact                                                   976

SEQ ID NO: 34           moltype = AA  length = 24
FEATURE                 Location/Qualifiers
source                  1..24
                        mol_type = protein
                        organism = unidentified
SEQUENCE: 34
MSLLTEVETP IRNEWGCRCN GSSD                                           24

SEQ ID NO: 35           moltype = RNA  length = 113
FEATURE                 Location/Qualifiers
source                  1..113
                        mol_type = other RNA
                        organism = unidentified
SEQUENCE: 35
aaggaattgc aaaggatgta atggaagtgc taaagcagag ctctatggga aattcagctc     60
ttgtgaagaa ataccctataa tgctcgaacc atttcagatt ctttcaattt gtt          113

SEQ ID NO: 36           moltype = RNA  length = 101
FEATURE                 Location/Qualifiers
source                  1..101
                        mol_type = other RNA
                        organism = synthetic construct
SEQUENCE: 36
ggatgtaatg gaagtgctaa agcagagctc tatgggaaat tcagctcctg tgaagaaata     60
cctataaatt caatttttac tgtacttctt actatgcatt t                        101
```

```
SEQ ID NO: 37        moltype = RNA  length = 113
FEATURE              Location/Qualifiers
source               1..113
                     mol_type = other RNA
                     organism = synthetic construct
SEQUENCE: 37
aaggaattgc aaaggatgta atggaagtgc taaagcagag ctctatggga aattcagctc  60
ttgtgaagaa atacctataa tgctcgaacc atttcagatt ctttcaattt gtt        113
```

INFLUENZA B VIRUS MUTANTS AND USES THEREFOR

CROSS-REFERENCE TO RELATED APPLICATION

This application is a divisional of U.S. patent application Ser. No. 16/488,913, filed Aug. 26, 2019, now U.S. Pat. No. 11,529,409, which is a U.S. National Phase Application under 35 U.S.C. § 371 of International Application No. PCT/US2018/019690, filed Feb. 26, 2018, which claims the benefit of and priority to U.S. Application No. 62/463,994, filed Feb. 27, 2017, the contents of which are incorporated herein by reference in their entirety.

SEQUENCE LISTING

The present application further incorporates by reference the sequence listing submitted herewith. The sequence listing .xml file identified as "090248-0240.xml" is 46,739 bytes in size, and was created on Mar. 30, 2023. The sequence listing, electronically filed herewith, does not extend beyond the scope of the specification, and does not contain new matter.

BACKGROUND

Influenza is a leading cause of death among American adults. Each year, about 36,000 people die from influenza, and more than 200,000 people are hospitalized. Influenza is a highly contagious disease that is spread by coughing, sneezing and through direct physical contact with objects that carry the virus such as doorknobs and telephones. Symptoms of influenza include fever, extreme fatigue, headache, chills and body aches; about 50 percent of infected people have no symptoms but are still contagious. Immunization is 50-60 percent effective in preventing influenza in healthy people under the age of 65, as long as the antigenicities of the circulating virus strain match those of the vaccine.

Vaccination is the main method for preventing influenza, and both live attenuated and inactivated (killed) virus vaccines are currently available. Live virus vaccines, typically administered intranasally, activate all phases of the immune system and can stimulate an immune response to multiple viral antigens. Thus, the use of live viruses overcomes the problem of destruction of viral antigens that may occur during preparation of inactivated viral vaccines. In addition, the immunity produced by live virus vaccines is generally more durable, more effective, and more cross-reactive than that induced by inactivated vaccines, and live virus vaccines are less costly to produce than inactivated virus vaccines. However, the mutations in attenuated virus are often ill-defined, and reversion is a concern.

SUMMARY

In one aspect, the present disclosure provides a recombinant influenza B virus having a mutant BM2 gene comprising SEQ ID NO: 1, SEQ ID NO: 2, SEQ ID NO: 3, SEQ ID NO: 4, or SEQ ID NO: 5. In some embodiments, the mutation in the BM2 gene results in failure of the virus to express the BM2 protein, or causes the virus to express a truncated BM2 protein. In some embodiments, the mutant BM2 gene does not revert to wild-type or to a non-wild-type sequence encoding a functional BM2 protein for at least 10 passages in an in vitro host cell system, wherein the host cell is modified to produce a functional version of the mutant gene, thereby providing the gene product to the virus in trans. In some embodiments, the recombinant virus elicits an immune response in a mammal infected with the virus. In some embodiments, the recombinant virus is non-pathogenic to a mammal infected with the virus. In some embodiments, the in vitro cell system comprises Madin-Darby Canine Kidney (MDCK) cells or Vero cells.

In one aspect, the present disclosure provides a composition comprising: a recombinant influenza B virus having a mutant BM2 gene comprising SEQ ID NO: 1, SEQ ID NO: 2, SEQ ID NO: 3, SEQ ID NO: 4, or SEQ ID NO: 5. In some embodiments, the mutation of the BM2 gene results in failure of the virus to express the BM2 protein, or causes the virus to express a truncated BM2 protein. In some embodiments, the virus elicits an immune response in a mammal infected with the virus. In some embodiments, the virus is non-pathogenic to a mammal infected with the virus. In some embodiments, the composition further comprises an adjuvant.

In one aspect, the present disclosure provides a method for propagating a recombinant influenza B virus, comprising: contacting a host cell with a recombinant influenza virus comprising SEQ ID NO: 1, SEQ ID NO: 2, SEQ ID NO: 3, SEQ ID NO: 4, or SEQ ID NO: 5; and incubating the host cell for a sufficient time and under conditions suitable for viral replication, wherein the host cell is modified to produce a functional version of the influenza BM2 gene, thereby providing the gene product to the virus in trans. In some embodiments, the method further comprises isolating progeny virus particles. In some embodiments, the method further comprises formulating the virus particles into a vaccine. In some embodiments, the virus fails to express the BM2 protein, or expresses a truncated BM2 protein. In some embodiments, the virus elicits an immune response in a mammal infected with the virus. In some embodiments, the virus is non-pathogenic to a mammal infected with the virus. In some embodiments, the mutant BM2 gene does not revert to wild-type or to a non-wild-type sequence encoding a functional BM2 protein for at least 10 passages of the host cell. In some embodiments, the host cell is an MDCK cell or a Vero cell.

In one aspect, the present disclosure provides a method for propagating a recombinant influenza A virus, comprising: contacting a host cell with a recombinant influenza A virus comprising SEQ ID NO: 33; and incubating the host cell for a sufficient time and under conditions suitable for viral replication, wherein the host cell is an MDCK cell modified to produce a wild-type version of the influenza BM2 gene, thereby providing a BM2 gene product to the virus in trans.

In one aspect, the present disclosure provides a method for propagating a recombinant influenza A virus comprising: contacting a host cell with a recombinant influenza A virus comprising SEQ ID NO: 33; and incubating the host cell for a sufficient time and under conditions suitable for viral replication, wherein the host cell is a Vero cell modified to produce a chimeric version of the influenza A M2 and influenza B BM2 gene selected from the group consisting of SEQ ID NO: 28, SEQ ID NO: 29, SEQ ID NO: 30, SEQ ID NO: 31, and SEQ ID NO: 32, thereby providing a chimeric M2:BM2 gene product to the virus in trans.

In one aspect, the present disclosure provides a method for propagating a recombinant influenza A virus comprising: contacting a host cell with a recombinant influenza A virus comprising SEQ ID NO: 33; and incubating the host cell for a sufficient time and under conditions suitable for viral replication, wherein the host cell is a Vero cell modified to produce a codon-optimized version of the BM2 gene comprising SEQ ID NO: 27, thereby providing a BM2 gene product to the virus in trans.

In one aspect, the present disclosure provides a recombinant influenza A virus comprising a mutant BM2 protein.

In one aspect, the present disclosure provides a host cell for propagating a recombinant influenza virus, wherein the host cell is a Vero cell modified to produce a gene product encoded by a cDNA sequence selected from the group consisting of SEQ ID NO: 27, SEQ ID NO: 28, SEQ ID NO: 29, SEQ ID NO: 30, SEQ ID NO: 31, and SEQ ID NO: 32. In some embodiments, the recombinant influenza virus is an influenza A virus comprising a mutant M2 gene as set forth in SEQ ID NO: 33. In some embodiments, the recombinant influenza virus is an influenza B virus comprising a mutant BM2 gene as set forth in SEQ ID NO: 4 or SEQ ID NO: 6, and wherein the Vero cell is modified to produce a gene product encoded by SEQ ID NO: 27.

BRIEF DESCRIPTION OF THE DRAWINGS

FIG. 2 is a schematic diagram of the influenza genomic segment 7 of B/FL/04/2006 in wild-type (WT) and six mutant BM2 genes (BM2SR also known as BM2SR-0), BM2SR-1, BM2SR-2, BM2SR-3, BM2SR-4, BM2SR-5). The pentanucleotide translational stop-start region is indicated by TAATG. Both the BM2SR-0 and BM2SR-1 mutants comprise a complete deletion of the BM2 open reading frame (ORF). The BM2SR-2 mutant comprises a BM2 deletion with the M1 translational regulatory elements intact. The BM2SR-3 mutant comprises a complete deletion of the BM2 ORF and an M1 M86V mutation. The BM2SR-4 mutant comprises a partial BM2 deletion, with the M1 translational regulatory elements intact. The BM2SR-5 mutant comprises a partial BM2 deletion with the M1 translational regulatory elements intact, and an M1 M86V mutation.

FIG. 9 is a chart showing the growth of M2-deficient influenza A M2SR (A/CA/07 M2SR and A/Brisbane/10 M2SR) and BM2-deficient influenza B M2SR (B/WI/01 BM2SR and B/Brisbane/60 BM2SR) strains in M2- and BM2-expressing MDCK cell substrates (M2CK and BM2CK).

FIGS. 17A and 17B are phylogenetic trees showing the evolutionary relationships between B/Lee/40 and modern influenza B viruses for BM2 protein (FIG. 17A) and BM1 protein (FIG. 17).

FIG. 22B is a chart showing the results of wild-type influenza B/CA/12/2015 (YL) and BM2SR4 B/CA/12/2015 virus infection of Vero (WT Vero), M2-expressing Vero (M2VeroA), and BM2-expressing (BM2Vero) Vero cell lines at MOI of 0.001. Aliquots of virus culture supernatant were withdrawn at time points (t=1, 2, 3, 4 Days) after inoculation and were frozen. Aliquots were tested for viral replication by $TCID_{50}$ assay in BM2CK cells. Samples with no detectable replication are plotted as $\log_{10} TCID_{50}=1.50$. Assay limit of detection $\log_{10} TCID_{50}=1.67$ shown as dotted line.

DETAILED DESCRIPTION

I. Definitions

Figure 1:
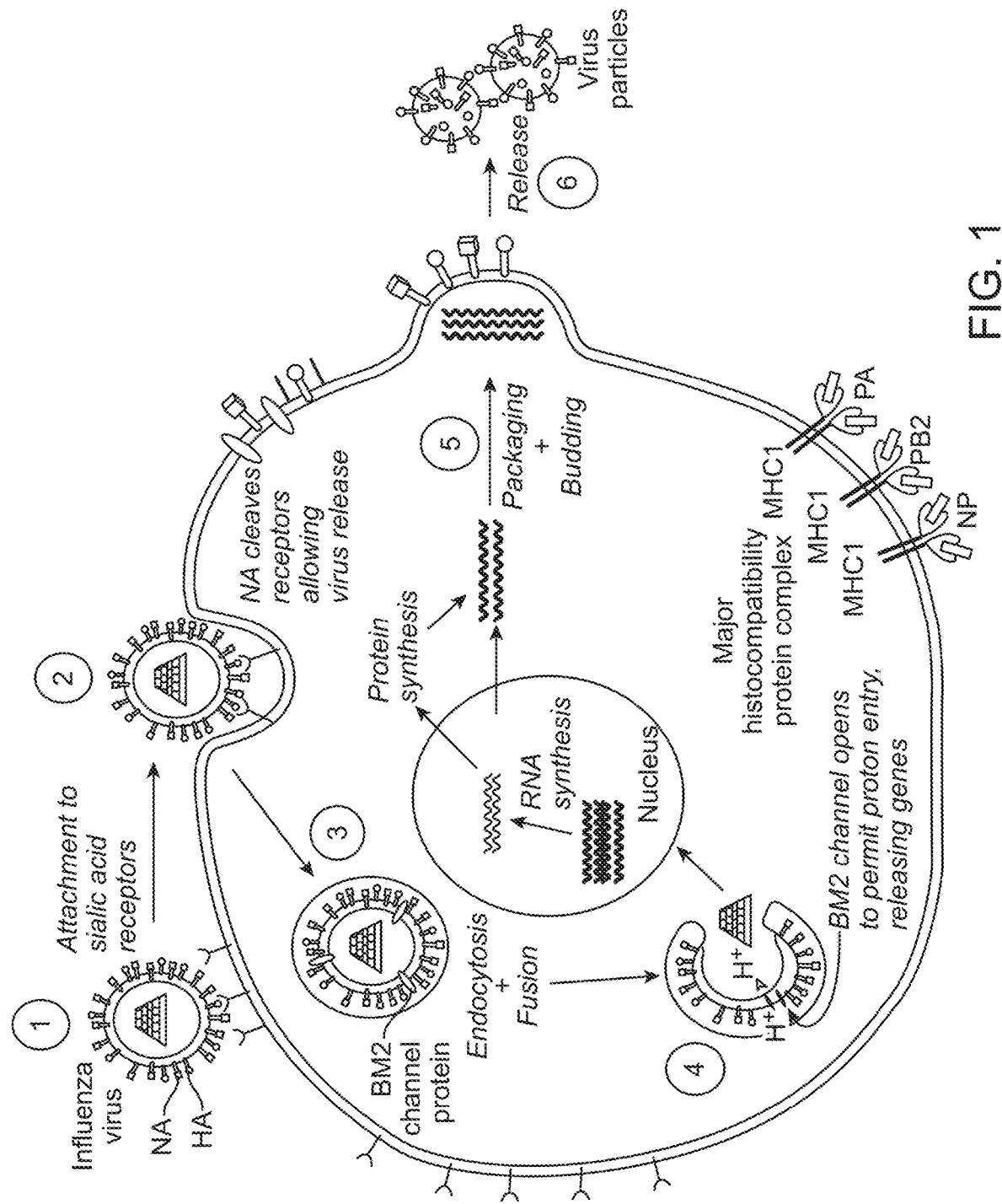
FIG. 1 is a graphic depicting the role of BM2 ion channel in an influenza virus life cycle, wherein (1) the influenza virus attaches to sialic acid receptors on a cell surface; (2) the virus is internalized into the cell; (3) the BM2 ion channel is expressed on the viral surface; (4) the BM2 ion channel opens to permit proton entry, leading to a release of viral RNA that enters the nucleus, is replicated and results in viral protein synthesis; and (5) the viral components are packaged into virions and released (6).

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus. This is in contrast to killed or completely inactivated virus.

As used herein, the terms "effective amount" or "therapeutically effective amount" or "pharmaceutically effective amount" refer to a quantity sufficient to achieve a desired therapeutic and/or prophylactic effect, e.g., an amount which results in the prevention of, disease, condition and/or symptom(s) thereof. In the context of therapeutic or prophylactic applications, the amount of a composition administered to the subject will depend on the type and severity of the disease and on the characteristics of the individual, such as general health, age, sex, body weight and tolerance to the composition drugs. It will also depend on the degree, severity and type of disease or condition. The skilled artisan will be able to determine appropriate dosages depending on these and other factors. In some embodiments, multiple doses are administered. Additionally or alternatively, in some embodiments, multiple therapeutic compositions or compounds (e.g., immunogenic compositions, such as vaccines) are administered.

As used herein, the term "host cell" refers to a cell in which a pathogen, such as a virus, can replicate. In some embodiments, host cells are in vitro, cultured cells (e.g., CHO cells, Vero cells, MDCK cells, etc.). Additionally or alternatively, in some embodiments, host cells are in vivo (e.g., cells of an infected vertebrate, such as an avian or mammal). In some embodiments, the host cells may be modified, e.g., to enhance viral production such as by enhancing viral infection of the host cell and/or by enhancing viral growth rate. By way of example, but not by way of limitation, exemplary host cell modifications include recombinant expression of 2-6-linked sialic acid receptors on the cell surface of the host cell, and/or recombinant expression of a protein in the host cells that has been rendered absent or ineffective in the pathogen or virus.

The term "immunogenic composition" is used herein to refer to a composition that will elicit an immune response in a mammal that has been exposed to the composition. In some embodiments, an immunogenic composition includes at least one of five BM2-deficient influenza B BM2SR mutants (e.g., BM2SR-1, BM2SR-2, BM2SR-3, BM2SR-4, BM2SR-5).

In some embodiments, the immunogenic compositions described herein may be formulated for administration (i.e., formulated for "exposure" to the mammal) in a number of forms. For example, in some embodiments, the immunogenic compositions are prepared for oral, pulmonary, intravenous, intramuscular, subcutaneous, parenteral, nasal, or topical administration. Compositions may also be formulated for specific dosage forms. For example, in some embodiments, the immunogenic composition may be formulated as a liquid, gel, aerosol, ointment, cream, lyophilized formulation, powder, cake, tablet, or capsule. In other embodiments, the immunogenic composition is formulated as a controlled release formulation, delayed release formulation, extended release formulation, pulsatile release formulation, and mixed immediate release formulation. In some embodiments, the immunogenic composition is provided as a liquid. In other embodiments, the immunogenic composition is provided in lyophilized form.

As used herein, the term "infected" refers to harboring a disease or pathogen, such as a virus. An infection can be intentional, such as by administration of a virus or pathogen (e.g., by vaccination), or unintentional, such as by natural transfer of the pathogen from one organism to another, or from a contaminated surface to the organism.

As used herein, the terms "isolated" and/or "purified" refer to in vitro preparation, isolation and/or purification of a nucleic acid (e.g., a vector or plasmid), polypeptide, virus or cell such that it is not associated with unwanted in vivo substances, or is substantially purified from unwanted in vivo substances with which it normally occurs. For example, in some embodiments, an isolated virus preparation is obtained by in vitro culture and propagation, and is substantially free from other infectious agents. As used herein, "substantially free" means below the level of detection for a particular compound, such as unwanted nucleic acids, proteins, cells, viruses, infectious agents, etc., using standard detection methods for that compound or agent.

As used herein the terms "mutant," "mutation," and "variant" are used interchangeably and refer to a nucleic acid or polypeptide sequence which differs from a wild-type sequences. In some embodiments, mutant or variant sequences are naturally occurring. In other embodiments, mutant or variant sequences are recombinantly and/or chemically introduced. In some embodiments, nucleic acid mutations include modifications (e.g., additions, deletions, substitutions) to RNA and/or DNA sequences. In some embodiments, modifications include chemical modification (e.g., methylation) and may also include the substitution or addition of natural and/or non-natural nucleotides. Nucleic acid mutations may be silent mutations (e.g., one or more nucleic acid changes which code for the same amino acid as the wild-type sequence) or may result in a change in the encoded amino acid, result in a stop codon, or may introduce splicing defects or splicing alterations. Nucleic acid mutations to coding sequences may also result in conservative or non-conservative amino acid changes.

As used herein the term "recombinant virus" refers to a virus that has been manipulated in vitro, e.g., using recombinant nucleic acid techniques, to introduce changes to the viral genome and/or to introduce changes to the viral proteins. For example, in some embodiments, recombinant viruses may include wild-type, endogenous, nucleic acid sequences and mutant and/or exogenous nucleic acid sequences. Additionally or alternatively, in some embodiments, recombinant viruses may include modified protein components, such as mutant or variant matrix, hemagglutinin, neuraminidase, nucleoprotein, non-structural and/or polymerase proteins.

As used herein the term "recombinant cell" or "modified cell" refer to a cell that has been manipulated in vitro, e.g., using recombinant nucleic acid techniques, to introduce nucleic acid into the cell and/or to modify cellular nucleic acids. Examples of recombinant cells includes prokaryotic or eukaryotic cells carrying exogenous plasmids, expression vectors and the like, and/or cells which include modifications to their cellular nucleic acid (e.g., substitutions, mutations, insertions, deletions, etc., into the cellular genome). An exemplary recombinant cell is one which has been manipulated in vitro to stably express an exogenous protein, such as a viral BM2 protein.

As used herein the term "single replication (SR) virus" refers to a virus that is defective in a virion protein that functions in viral entry of a host cell or release from a host cell. For example, M2SR, as described herein, belongs to the novel class of single-replication (SR) virus vaccines in contrast to classical live attenuated influenza vaccines. SR viruses are defective in a virion protein that functions in viral entry or release, such as the flu M2 ion channel protein that does not affect viral genome replication but is indispensable for virus growth. In contrast, traditional attenuated live virus vaccines contain multiple mutations in the viral replication machinery resulting in a highly attenuated phenotype. The SR vaccine virus mechanisms therefore do not affect the virus infection kinetics and antigen production in contrast to attenuated live vaccines.

As used herein "subject" and "patient" are used interchangeably and refer to an animal, for example, a member of any vertebrate species. The methods and compositions of the presently disclosed subject matter are particularly useful for warm-blooded vertebrates including mammals and birds. Exemplary subjects may include mammals such as humans, as well as mammals and birds of importance due to being endangered, of economic importance (animals raised on farms for consumption by humans) and/or of social importance (animals kept as pets or in zoos) to humans. In some embodiments, the subject is a human. In some embodiments, the subject is not human.

As used herein, the term "type" and "strain" as used in conjunction with a virus are used interchangeably, and are used to generally refer to viruses having different characteristics. For example, influenza A virus is a different type of virus than influenza B virus. Likewise, influenza A H1N1 is a different type of virus than influenza A H2N1, H2N2 and H3N2. Additionally or alternatively, in some embodiments, different types of virus such as influenza A H2N1, H2N2 and H3N2 may be termed "subtypes" based on the antigenic difference of the tow viral transmembrane proteins, hemagglutinin (HA) and neuraminidase (NA). Influenza B viruses, which circulate almost exclusively in humans, are not classified into subtypes. Two closely related lineages of type B viruses (B/Victoria and B/Yamagata) are examples of influenza B viruses circulating in humans.

The term "vaccine" is used herein to refer to a composition that is administered to a subject to produce or increase immunity to a particular disease. In some embodiments, vaccines include a pharmaceutically acceptable adjuvant and/or a pharmaceutically acceptable carrier.

As used herein, the term "vRNA" refers to the RNA comprising a viral genome, including segmented or non-segmented viral genomes, as well as positive and negative strand viral genomes. vRNA may be wholly endogenous and "wild-type" and/or may include recombinant and/or mutant sequences.

As used herein, "BM2SR-1" refers to SEQ ID NO: 1, a virus comprising SEQ ID NO: 1, or a vaccine comprising a virus comprising SEQ ID NO: 1, depending on the context in which it is used. For example, in describing mutations of the BM2 gene demonstrated herein, "BM2SR-1" refers to SEQ ID NO: 1. As used herein, "BM2SR-2" refers to SEQ ID NO: 2, a virus comprising SEQ ID NO: 2, or a vaccine comprising a virus comprising SEQ ID NO: 2, depending on the context in which it is used. For example, in describing mutations of the BM2 gene demonstrated herein, "BM2SR-2" refers to SEQ ID NO: 2. As used herein, "BM2SR-3"

refers to SEQ ID NO: 3, a virus comprising SEQ ID NO: 3, or a vaccine comprising a virus comprising SEQ ID NO: 3, depending on the context in which it is used. For example, in describing mutations of the BM2 gene demonstrated herein, "BM2SR-3" refers to SEQ ID NO: 3. As used herein, "BM2SR-4" refers to SEQ ID NO: 4, a virus comprising SEQ ID NO: 4, or a vaccine comprising a virus comprising SEQ ID NO: 4, depending on the context in which it is used. For example, in describing mutations of the BM2 gene demonstrated herein, "BM2SR-4" refers to SEQ ID NO: 4. As used herein, "BM2SR-5" refers to SEQ ID NO: 5, a virus comprising SEQ ID NO: 5, or a vaccine comprising a virus comprising SEQ ID NO: 5, depending on the context in which it is used. For example, in describing mutations of the BM2 gene demonstrated herein, "BM2SR-5" refers to SEQ ID NO: 5. As used herein, "BM2SR-0" refers to SEQ ID NO: 6, a virus comprising SEQ ID NO: 6, or a vaccine comprising a virus comprising SEQ ID NO: 6, depending on the context in which it is used. For example, in describing mutations of the BM2 gene demonstrated herein, "BM2SR-0" refers to SEQ ID NO: 6. Unless otherwise noted, "BM2SR" refers to BM2SR-0.

II. Influenza B Virus

A. General

Influenza is a leading cause of death among American adults. The causal agent of influenza are viruses of the family Orthomyroviridae including influenza A virus, influenza B virus, and influenza C virus, with influenza B circulating almost exclusively in humans.

The influenza B virus is an enveloped, negative-strand RNA virus. The genome of influenza B virus is contained on eight single (non-paired) RNA strands the complements of which code for eleven proteins. Of these proteins, nine are also found in influenza A virus: three RNA-dependent RNA polymerase subunits (PB1, PB2, and PA), hemagglutinin (HA), nucleoprotein (NP), neuraminidase (NA), matrix protein (M1 or BM1), and two non-structural proteins (NS1 and NS2, also known as NEP). Two proteins, NB and BM2, are unique to influenza B virus. The total genome size is about 14,500 bases. The segmented nature of the genome allows for the exchange of entire genes between different viral strains during cellular cohabitation, a process known as reassortment. The eight RNA segments, numbered in order of decreasing length, are as follows. Segments 1, 2, and 3 encode PB1, PB2, and PA, respectively, which are RNA polymerase subunits. Segment 4 encodes HA (hemagglutinin). Segment 5 encodes NP (nucleoprotein). Segment 6 encodes both NB (NB protein, the function of which is unknown) and NA (neuraminidase). Segment 7 encodes both BM1 (matrix protein) and BM2 (ion channel) by a bicistronic mRNA, the translational strategy of which is unique. The BM2 initiation codon overlaps with the BM1 termination codon (TAATG, a stop-start pentanucleotide motif). The BM2 protein is translated by this stop-start translational mechanism unlike the M2 protein of influenza A virus, which is translated from a spliced mRNA. Segment 8 encodes both NS1 and NEP by using different reading frames from the same RNA segment.

Both influenza A and B evolve antigenically over time by the process of antigenic drift, in which mutations to hemagglutinin (HA) protein allow viruses to escape existing human immunity and persist in the human population. There are several subtypes of influenza A, named according to an H number (for the type of hemagglutinin) and an N number (for the type of neuraminidase). Currently, there are 16 different H antigens known (H1 to H16) and nine different N antigens known (N1 to N9). Each virus subtype has mutated into a variety of strains with differing pathogenic profiles; some pathogenic to one species but not others, some pathogenic to multiple species. Exemplary influenza A virus subtypes that have been confirmed in humans, include, but are not limited to H1N1 which caused the "Spanish Flu" and the 2009 swine flu outbreak; H2N2 which caused the "Asian Flu" in the late 1950s; H3N2 which caused the Hong Kong Flu in the late 1960s; H5N1, considered a global influenza pandemic threat through its spread in the mid-2000s; H7N7; H1N2 which is currently endemic in humans and pigs; and H9N2, H7N2, H7N3, H5N2, H10N7. Influenza B is not divided into subtypes; however, two antigenetically and genetically distinct lineages, Victoria and Yamagata named after strains B/Victoria/2/87 and B/Yamagata/16/88, are currently circulating in humans.

Influenza viruses have a standard nomenclature that includes virus type; species from which it was isolated (if non-human); location at which it was isolated; isolate number; isolate year; and, for influenza A viruses only, HA and NA subtype. Thus, B/Yamagata/16/88 was isolate number 16 of a human influenza B virus taken in Yamagata (Japan) in 1988.

B. Life Cycle and Structure

The life cycle of influenza viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell. Different viral proteins play a role in each of these steps.

The influenza B particle is made up of a lipid envelope which encapsulates the viral core. The inner side of the envelope is lined by the matrix protein (BM1), while the outer surface is characterized by two types of glycoprotein spikes: hemagglutinin (HA) and neuraminidase (NA). BM2, a transmembrane ion channel protein, is also part of the lipid envelope. See, e.g., FIG. 1.

The HA protein, a trimeric type I membrane protein, is responsible for binding to sialyloligosaccharides (oligosaccharides containing terminal sialic acid linked to galactose) on host cell surface glycoproteins or glycolipids. This protein is also responsible for fusion between viral and host cell membranes, following virion internalization by endocytosis.

Neuraminidase (NA), a tetrameric type II membrane protein, is a sialidase that cleaves terminal sialic acid residues from the glycoconjugates of host cells and the HA and NA, and thus is recognized as receptor-destroying enzyme. This sialidase activity is necessary for efficient release of progeny virions from the host cell surface, as well as prevention of progeny aggregation due to the binding activity of viral HAs with other glycoproteins. Thus, the receptor-binding activity of the HA and the receptor-destroying activity of the NA likely act as counterbalances, allowing efficient replication of influenza.

The genome segments are packaged into the core of the viral particle. The RNP (RNA plus nucleoprotein, NP) is in helical form with three viral polymerase polypeptides associated with each segment.

The influenza virus life cycle begins with binding of the HA to sialic acid-containing receptors on the surface of the host cell, followed by receptor-mediated endocytosis (FIG. 1). The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (BM1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: (1) synthesis of an mRNA with a 5' cap and 3' polyA structure, (2) a full-length complementary RNA (cRNA), and (3) genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a role late in infection by removing sialic acid from sialyloligosaccharides, thus releasing newly assembled virions from the cell surface and preventing the self-aggregation of virus particles. Although virus assembly involves protein-protein and protein-vRNA interactions, the nature of these interactions remains largely unknown.

C. Role of the BM2 Protein

As described above, spanning the viral membrane are three proteins: hemagglutinin (HA), neuramimidase (NA), and BM2. With respect to influenza A, the extracellular domains (ectodomains) of HA and NA are quite variable, while the ectodomain domain of M2 is essentially invariant among influenza A viruses. Without wishing to be bound by theory, in influenza A viruses, the M2 protein which possesses ion channel activity, is thought to function at an early state in the viral life cycle between host cell penetration and uncoating of viral RNA. Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm. In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment. It was also shown that the M2 transmembrane domain itself can function as an ion channel. M2 protein ion channel activity is thought to be essential in the life cycle of influenza viruses, because amantadine hydrochloride, which blocks M2 ion channel activity, has been shown to inhibit viral replication.

The functional counterpart to the influenza A virus M2 protein in influenza B viruses is the type III transmembrane protein known as BM2. The mechanism for translation of involves a coupled termination/reinitiation event that is described below.

III. BM2 Viral Mutants

In one aspect, influenza B viruses harboring a mutant BM2 vRNA sequence are disclosed. Typically, such mutants do not have BM2 ion channel activity, exhibit attenuated growth properties in vivo, cannot produce infectious progeny, and are non-pathogenic or show reduced pathogenesis in infected subjects. The mutant viruses are immunogenic, and when used as a vaccine, provide protection against infection with a counterpart wild-type and/or other pathogenic virus. Additionally, the BM2 mutants disclosed herein are stable, and do not mutate to express a functional BM2 polypeptide, regardless of the host cell used. Additionally or alternatively, in some embodiments, the BM1 protein of these mutants is produced without detectable alteration to its function. In some embodiments, viruses harboring the mutant BM2 nucleic acid sequences cannot multiply in a host cell in which a corresponding wild-type virus could be propagated. By way of example, but not by way of limitation, in some embodiments, the wild-type virus can be grown, propagated and replicate in culturing MDCK cells, CHO cells and/or Vero cells, while the corresponding virus harboring a mutant BM2 sequence cannot grow, replicate more than one cycle, or be propagated in the same type of cells.

As noted above, in some embodiments, the BM2 mutant virus is stable, and does not mutate or revert to wild-type or to a non-wild-type sequence encoding a functional BM2 protein in a host cell. For example, in some embodiments, the BM2 mutant virus is stable for 2 passages, 3 passages, 5 passages, 10 passages, 12 passages, 15 passages, 20 passages, 25 passages or more than 25 passages in a host cell. In some embodiments, the host cell is an unmodified host cell. In other embodiments, the host cell is a modified host cell, such as a MDCK cell which expresses the BM2 protein (i.e., a BM2CK cell).

In some embodiments, the BM2 mutants include one or more nucleic acid substitutions and/or deletions. In some embodiments, the mutations are localized in nucleic acids which code for one or more of the extracellular domains of the BM2 protein, the transmembrane domain of the BM2 proteins and/or the cytoplasmic tail of the BM2 protein. Additionally or alternatively, in some embodiments, one or more nucleic acid mutations results in one or more stop codons and/or one or more amino acid deletions of the BM2 peptide. In some embodiments, viruses carrying the mutant BM2 nucleic acid produce a non-functional BM2 polypeptide. In some embodiments, viruses carrying the mutant BM2 nucleic acid do not produce a BM2 polypeptide. In some embodiments, viruses carrying the mutant BM2 nucleic acid produce a truncated BM2 polypeptide.

As noted above, the influenza B genomic segment 7 expresses two major polypeptides that are required by the virus for replication, the BM1 matrix protein and the BM2 proton channel. Expression of the BM1 and the BM2 polypeptides is regulated in part by a pentanucleotide motif translational slippage site that lies at the junction between the BM1 and BM2 ORFs. The pentanucleotide motif, TAATG, contains both a TAA stop codon for termination of M1 translation and an ATG start codon for initiation of M2 in an alternate −1 reading frame. This pentanucleotide motif and flanking sequences have been shown to be important for the regulation of expression of the M1 protein. The BM2 protein is synthesized by a coupled translational termination-reinitiation mechanism at the overlapping stop-start pentanucleotide in a bicistronic mRNA transcribed from RNA segment 7. In the mRNA transcribed from RNA segment 7, there is a pentanucleotide, residues 769±773, in which the AUG initiation codon for the BM2 protein overlaps with the termination codon for the M1 protein (Horvath et al., *EMBO Joural* 9:2639-2647 (1990)). The BM2 protein is synthesized by a coupled translational stop±start mechanism at the pentanucleotide which is dependent upon the initiation and termination of the upstream M1 protein (Horvath et al., 1990). The process requires the close proximity of termination and reinitiation codons and a defined region of mRNA upstream of the stop-start site that includes a functionally essential stretch of bases with complementarity to helix 26 of 18S rRNA. This complementary region is located within the loop of a hairpin structure adjacent to the terminating ribosome and may play a role in the reinitiation process for the expression of the BM2 protein. This secondary structure may have an additional role in stabilizing the segment 7 mRNA, thus BM2 mutants that disrupt or affect the hairpin structure may have decreased M1 protein expression in addition to the desired lack of BM2 expression.

Another region required for replication and packing of all 8 genomic segments is the 5' non-coding region (5'NCR) of the genomic RNA. Because influenza is a negative-strand RNA virus, the genomic 5'NCR represents the 3'NCR of the mRNA and cDNA. Furthermore, the structural requirement for the 5'NCR may extend into the protein ORF itself. This has been demonstrated for influenza A; silent protein coding mutations near the 3'end of mRNA (or near the genomic 5'NCR) of segment 4 (HA) that change the codon but not the amino acid composition of HA can completely block virus replication. Thus, regions within the COOH terminus of M2 may be important structurally and for efficient genomic packing into the virion.

The requirement for BM2 in viral replication was demonstrated by constructing an influenza B virus with a precise deletion of the 109-amino acid BM2 ORF. This virus can replicate in M2CK cells, which are MDCK cells constitutively expressing BM2 protein. While this M2 deletion construct does allow replication in the MDCK lineage cells, the total deletion removes portions of regulatory elements that could adversely affect M1 protein expression, especially when limited by other factors, which may affect the production of virus. For example, while influenza B viruses grow to high titers in MDCK cells, they are highly restricted in Vero cells, in part by low expression of the M1 protein (Nakamura, 1981). Therefore, manipulation of the M segment may inadvertently further affect M1 expression.

Figure 2:
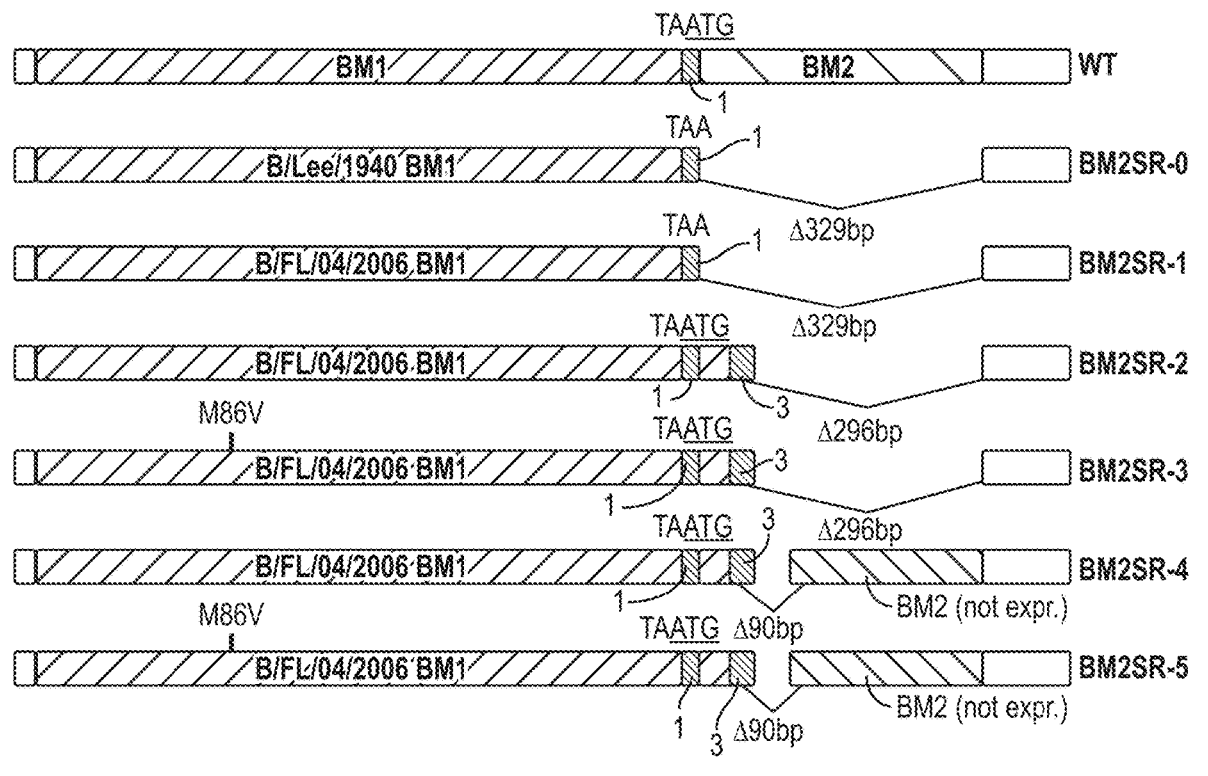

To address these shortcomings, a series of five novel BM2 null mutant constructs (BM2SR-1, BM2SR-2, BM2SR-3, BM2SR-4, and BM2SR-5) based upon the B/Florida/4/2006 segment 7 (FIG. 2) were designed and then synthesized as double-stranded DNA fragments that are suitable for standard in vitro gene-assembly procedures using standard techniques known in the art. The single-stranded mRNA or plus-sense DNA nucleotide sequences of the constructs are provided in Table 1, BM2SR-1 (SEQ ID NO: 1), BM2SR-2 (SEQ ID NO: 2), BM2SR-3 (SEQ ID NO: 3), BM2SR-4 (SEQ ID NO: 4), BM2SR-5 (SEQ ID NO: 5), and BM2SR-0 (SEQ ID NO: 6).

TABLE 1

M segment 7 sequences of BM2SR influenza viruses containing null mutations in BM2 genes.

```
BM2SR-1 (SEQ ID NO: 1) influenza B/FL/4/2006 Segment 7 with intact BM1 + total BM2
deletion of 329 bp (indicated by -) (mRNA sense).
5'AGCAGAAGCACGCACTTTCTTAAAATGTCGCTGTTTGGAGACACAATTGCCTAC
CTGCTTTCATTGACAGAAGATGGAGAAGGCAAAGCAGAACTAGCAGAAAAATTA
CACTGTTGGTTCGGTGGGAAAGAATTTGACCTAGACTCTGCCTTGGAATGGATAA
AAAACAAAAGATGCTTAACTGACATACAGAAAGCACTAATTGGCGCCTCTATCT
GCTTTTTAAAACCCAAAGACCAGGAAAGAAAAAGAAGATTCATCACAGAGCCCC
TATCAGGAATGGGGACAACAGCAACAAAAAAGAAGGGCCTGATTCTAGCTGAGA
GAAAAATGAGAAGATGTGTGAGCTTCCATGAAGCATTTGAAATAGCAGAAGGCC
ATGAAAGCTCAGCGTTACTATATTGTCTCATGGTCATGTACCTGAATCCTGGAAA
TTATTCAATGCAAGTAAAACTAGGAACGCTCTGTGCTTTGTGCGAAAAACAAGCA
TCACATTCACACAGGGCTCATAGCAGAGCAGCGAGATCTTCAGTGCCTGGAGTG
AGACGGGAAATGCAGATGGTCTCAGCTATGAACACAGCAAAAACAATGAATGGA
ATGGGAAAAGGAGAAGACGTTCAAAAACTGGCAGAAGAACTGCAAAGCAACAT
TGGAGTATTGAGATCTCTTGGGGCAAGTCAAAAGAATGGGGAAGGAATTGCAAA
GGATGTAATGGAAGTGCTAAAGCAGAGCTCTATGGGAAATTCAGCTCTTGTGAA
GAAATACCTAA---------------------------------------------
--------------------------------------------------------
---------------------
ATTCAATTTTTACTGTACTTCTTACTATGCATTTAAGCAAATTGTAATCAATGTCA
GCAAATAAACTGGAAAAAGTGCGTTGTTTCTACT
BOLD UPPER CASE = BM1 ORF Stop Codon
- = designates deleted nucleotides BM2SR-2 (SEQ ID NO: 2) influenza B/FL/4/2006 Segment 7 with intact BM1 + partial BM2
deletion of 296 bp (indicated by -) + insertion of stop codons in 3 frames. (mRNA sense).
5'AGCAGAAGCACGCACTTTCTTAAAATGTCGCTGTTTGGAGACACAATTGCCTAC
CTGCTTTCATTGACAGAAGATGGAGAAGGCAAAGCAGAACTAGCAGAAAAATTA
CACTGTTGGTTCGGTGGGAAAGAATTTGACCTAGACTCTGCCTTGGAATGGATAA
AAAACAAAAGATGCTTAACTGACATACAGAAAGCACTAATTGGCGCCTCTATCT
GCTTTTTAAAACCCAAAGACCAGGAAAGAAAAAGAAGATTCATCACAGAGCCCC
TATCAGGAATGGGGACAACAGCAACAAAAAAGAAGGGCCTGATTCTAGCTGAGA
GAAAAATGAGAAGATGTGTGAGCTTCCATGAAGCATTTGAAATAGCAGAAGGCC
ATGAAAGCTCAGCGTTACTATATTGTCTCATGGTCATGTACCTGAATCCTGGAAA
TTATTCAATGCAAGTAAAACTAGGAACGCTCTGTGCTTTGTGCGAAAAACAAGCA
TCACATTCACACAGGGCTCATAGCAGAGCAGCGAGATCTTCAGTGCCTGGAGTG
AGACGGGAAATGCAGATGGTCTCAGCTATGAACACAGCAAAAACAATGAATGGA
ATGGGAAAAGGAGAAGACGTTCAAAAACTGGCAGAAGAACTGCAAAGCAACAT
TGGAGTATTGAGATCTCTTGGGGCAAGTCAAAAGAATGGGGAAGGAATTGCAAA
GGATGTAATGGAAGTGCTAAAGCAGAGCTCTATGGGAAATTCAGCTCTTGTGAA
GAAATACCTATAATGCTCGAACCATTTCAGATTCTTTCAATTTGTtagAtagC-----
--------------------------------------------------------
-----------------------
taaATTCAATTTTTACTGTACTTCTTACTATGCATTTAAGCAAATTGTAATCAATGT
CAGCAAATAAACTGGAAAAAGTGCGTTGTTTCTACT
BOLD UPPER CASE = BM1 ORF Stop Codon
bold lower case= Inserted BM2 Stop Codons
- = designates deleted nucleotides
```

TABLE 1-continued

M segment 7 sequences of BM2SR influenza viruses containing null mutations in BM2 genes.

BM2SR-3 (SEQ ID NO: 3) influenza B/FL/4/2006 Segment 7 with intact BM1 + BM1
M86V mutation + partial BM2 deletion of 296 bp (indicated by -) + insertion of stop codons
in 3 frames. (mRNA sense).
5'AGCAGAAGCACGCACTTTCTTAAAATGTCGCTGTTTGGAGACACAATTGCCTAC
CTGCTTTCATTGACAGAAGATGGAGAAGGCAAAGCAGAACTAGCAGAAAAATTA
CACTGTTGGTTCGGTGGGAAAGAATTTGACCTAGACTCTGCCTTGGAATGGATAA
AAAACAAAAGATGCTTAACTGACATACAGAAAGCACTAATTGGCGCCTCTATCT
GCTTTTTAAAACCCAAAGACCAGGAAAGAAAAAGAAGATTCATCACAGAGCCCC
TATCAGGAgTGGGGACAACAGCAACAAAAAAGAAGGGCCTGATTCTAGCTGAGA
GAAAAATGAGAAGATGTGTGAGCTTCCATGAAGCATTTGAAATAGCAGAAGGCC
ATGAAAGCTCAGCGTTACTATATTGTCTCATGGTCATGTACCTGAATCCTGGAAA
TTATTCAATGCAAGTAAAACTAGGAACGCTCTGTGCTTTGTGCGAAAAACAAGCA
TCACATTCACACAGGGCTCATAGCAGAGCAGCGAGATCTTCAGTGCCTGGAGTG
AGACGGGAAATGCAGATGGTCTCAGCTATGAACACAGCAAAAACAATGAATGGA
ATGGGAAAAGGAGAAGACGTTCAAAAACTGGCAGAAGAACTGCAAAGCAACAT
TGGAGTATTGAGATCTCTTGGGGCAAGTCAAAAGAATGGGGAAGGAATTGCAAA
GGATGTAATGGAAGTGCTAAAGCAGAGCTCTATGGGAAATTCAGCTCTTGTGAA
GAAATACCTATAATGCTCGAACCATTTCAGATTCTTTCAATTTGTtagAtagC-----
--------------------------------------------------------
-----------------------------
taaATTCAATTTTTACTGTACTTCTTACTATGCATTTAAGCAAATTGTAATCAATGT
CAGCAAATAAACTGGAAAAAGTGCGTTGTTTCTACT
Bold Underline Mixed Case = BM1 M86V Mutation Codon
BOLD UPPER CASE = BMI ORF Stop Codon
UNDERLINE UPPERCASE = BM2 ORF remnant
bold lower case= Inserted BM2 Stop Codons
- = designates deleted nucleotides BM2SR-4 (SEQ ID NO: 4) influenza B/FL/4/2006 Segment 7 with intact BM1 + partial BM2
deletion of 90 bp (indicated by -) + insertion of 3 stop codons in 3 frames. (mRNA sense).
5'AGCAGAAGCACGCACTTTCTTAAAATGTCGCTGTTTGGAGACACAATTGCCTAC
CTGCTTTCATTGACAGAAGATGGAGAAGGCAAAGCAGAACTAGCAGAAAAATTA
CACTGTTGGTTCGGTGGGAAAGAATTTGACCTAGACTCTGCCTTGGAATGGATAA
AAAACAAAAGATGCTTAACTGACATACAGAAAGCACTAATTGGCGCCTCTATCT
GCTTTTTAAAACCCAAAGACCAGGAAAGAAAAAGAAGATTCATCACAGAGCCCC
TATCAGGAATGGGGACAACAGCAACAAAAAAGAAGGGCCTGATTCTAGCTGAGA
GAAAAATGAGAAGATGTGTGAGCTTCCATGAAGCATTTGAAATAGCAGAAGGCC
ATGAAAGCTCAGCGTTACTATATTGTCTCATGGTCATGTACCTGAATCCTGGAAA
TTATTCAATGCAAGTAAAACTAGGAACGCTCTGTGCTTTGTGCGAAAAACAAGCA
TCACATTCACACAGGGCTCATAGCAGAGCAGCGAGATCTTCAGTGCCTGGAGTG
AGACGGGAAATGCAGATGGTCTCAGCTATGAACACAGCAAAAACAATGAATGGA
ATGGGAAAAGGAGAAGACGTTCAAAAACTGGCAGAAGAACTGCAAAGCAACAT
TGGAGTATTGAGATCTCTTGGGGCAAGTCAAAAGAATGGGGAAGGAATTGCAAA
GGATGTAATGGAAGTGCTAAAGCAGAGCTCTATGGGAAATTCAGCTCTTGTGAA
GAAATACCTATAATGCTCGAACCATTTCAGATTCTTTCAATTTGTtagAtagCtaa---
----------------------------------------
AAGGGGCCAAATAAAGAGACAATAAACAGAGAGGTATCAATTTTGAGACACAGT
TACCAAAAAGAAATCCAGGCCAAAGAAGCAATGAAGGAAGTACTCTCTGACAAC
ATGGAGGTATTGAGTGACCACATAGTAATTGAGGGGCTTTCTGCTGAAGAGATA
ATAAAAATGGGTGAAACAGTTTTGGAGGTAGAAGAATTGCATTAAATTCAATTTT
TACTGTACTTCTTACTATGCATTTAAGCAAATTGTAATCAATGTCAGCAAATAAA-
CTGGAAAAAGTGCGTTGTTTCTACT
BOLD UPPER CASE = BMI ORF Stop Codon
UNDERLINE UPPERCASE = BM2 ORF remnant
BOLD UNDERLINE UPPERCASE = BM2 ORF Stop Codon
bold lower case= Inserted BM2 Stop Codons
- = designates deleted nucleotides BM2SR-5 (SEQ ID NO: 5) influenza B/FL/4/2006 Segment 7 with intact BM1 + BM1
M86V mutation + partial BM2 deletion of 90 bp (indicated by -) + insertion of 3 stop codons
in 3 frames. (mRNA sense).
5'AGCAGAAGCACGCACTTTCTTAAAATGTCGCTGTTTGGAGACACAATTGCCTAC
CTGCTTTCATTGACAGAAGATGGAGAAGGCAAAGCAGAACTAGCAGAAAAATTA
CACTGTTGGTTCGGTGGGAAAGAATTTGACCTAGACTCTGCCTTGGAATGGATAA
AAAACAAAAGATGCTTAACTGACATACAGAAAGCACTAATTGGCGCCTCTATCT
GCTTTTTAAAACCCAAAGACCAGGAAAGAAAAAGAAGATTCATCACAGAGCCCC
TATCAGGAgTGGGACAACAGCAACAAAAAAGAAGGGCCTGATTCTAGCTGAGA
GAAAAATGAGAAGATGTGTGAGCTTCCATGAAGCATTTGAAATAGCAGAAGGCC
ATGAAAGCTCAGCGTTACTATATTGTCTCATGGTCATGTACCTGAATCCTGGAAA
TTATTCAATGCAAGTAAAACTAGGAACGCTCTGTGCTTTGTGCGAAAAACAAGCA
TCACATTCACACAGGGCTCATAGCAGAGCAGCGAGATCTTCAGTGCCTGGAGTG
AGACGGGAAATGCAGATGGTCTCAGCTATGAACACAGCAAAAACAATGAATGGA
ATGGGAAAAGGAGAAGACGTTCAAAAACTGGCAGAAGAACTGCAAAGCAACAT

TABLE 1-continued

M segment 7 sequences of BM2SR influenza viruses containing null mutations in BM2 genes.

```
TGGAGTATTGAGATCTCTTGGGGCAAGTCAAAAGAATGGGGAAGGAATTGCAAA
GGATGTAATGGAAGTGCTAAAGCAGAGCTCTATGGGAAATTCAGCTCTTGTGAA
GAAATACCTATAATGCTCGAACCATTTCAGATTCTTTCAATTTGTtagAtagCtaa------
-------------------------------------
AAGGGGCCAAATAAAGAGACAATAAACAGAGAGGTATCAATTTTGAGACACAGT
TACCAAAAAGAAATCCAGGCCAAAGAAGCAATGAAGGAAGTACTCTCTGACAAC
ATGGAGGTATTGAGTGACCACATAGTAATTGAGGGGCTTTCTGCTGAAGAGATA
ATAAAAATGGGTGAAACAGTTTTGGAGGTAGAAGAATTGCATTAAATTCAATTTT
TACTGTACTTCTTACTATGCATTTAAGCAAATTGTAATCAATGTCAGCAAATAAA-
CTGGAAAAAGTGCGTTGTTTCTACT
Bold Underline Mixed Case = BM1 M86V Mutation Codon
BOLD UPPER CASE = BM1 ORF Stop Codon
UNDERLINE UPPERCASE = BM2 ORF remnant
bold lower case= Inserted BM2 Stop Codons
BOLD UNDERLINE UPPERCASE = BM2 ORF Stop Codon
- = designates deleted nucleotides BM2SR-0 (SEQ ID NO: 6) influenza B/Lee/1940 Segment 7 with intact BM1 + total BM2
deletion of 329 bp (indicated by -) (mRNA sense).
5'AGCAGAAGCACGCACTTTCTTAAAATGTCGCTGTTTGGAGACACAATTGCCTAC
CTGCTTTCACTAATAGAAGATGGAGAAGGCAAAGCAGAACTAGCTGAAAAATTA
CACTGTTGGTTCGGTGGGAAAGAATTTGACCTAGATTCTGCTTTGGAATGGATAA
AAAACAAAAGGTGCCTAACTGATATACAAAAAGCACTAATTGGTGCCTCTATAT
GCTTTTTAAAACCCAAAGACCAAGAAAGAAAAAGGAGATTCATCACAGAGCCCC
TGTCAGGAATGGGAACAACAGCAACAAAGAAGAAAGGCCTAATTCTAGCTGAGA
GAAAAATGAGAAGATGTGTAAGCTTTCATGAAGCATTTGAAATAGCAGAAGGCC
ACGAAAGCTCAGCATTACTATATTGTCTTATGGTCATGTACCTAAACCCTGAAAA
CTATTCAATGCAAGTAAAACTAGGAACGCTCTGTGCTTTATGCGAGAAACAAGC
ATCGCACTCGCATAGAGCCCATAGCAGAGCAGCAAGGTCTTCGGTACCTGGAGT
AAGACGAGAAATGCAGATGGTTTCAGCTATGAACACAGCAAAGACAATGAATGG
AATGGGAAAGGGAGAAGACGTCCAAAAACTAGCAGAAGAGCTGCAAAACAACA
TTGGAGTGTTGAGATCTCTAGGAGCAAGTCAAAAGAATGGAGAAGGAATTGCCA
AAGATGTAATGGAAGTGCTAAAACAGAGCTCTATGGGAAATTCAGCTCTTGTGA
GGAAATACTTATAA------------------------------------------
--------------------------------------------------------
-----------------
GCCCAATTTTCACTGTATTTCTTACTATGCATTTAAGCAAATTGTAATCAATGTCA
GTGAATAAAACTGGAAAAAGTGCGTTGTTTCTACT
BOLD UPPER CASE = BM1 ORF Stop Codon
- = designates deleted nucleotides
```

The BM2SR-0, BM2SR-1, and BM2SR-3 mutants do not express a BM2 polypeptide. The BM2SR-2, BM2SR-4, and BM2SR-5 mutants could potentially express a truncated polypeptide comprising the first eleven amino acids of the BM2 protein; however, this has not yet been demonstrated.

The wild-type influenza B segment 7 showing the BM1 and BM2 coding sequences and the pentanucleotide motif in bold underlining are provided in Table 2.

TABLE 2

Wild-type BM1 and BM2 coding sequences.

```
BM1/BM2 coding sequence (SEQ ID NO: 7) influenza B/Lee/40 Segment 7.
AGCAGAAGCACGCACTTTCTTAAAATGTCGCTGTTTGGAGACACAATTGCCTACC
TGCTTTCACTAATAGAAGATGGAGAAGGCAAAGCAGAACTAGCTGAAAAATTAC
ACTGTTGGTTCGGTGGGAAAGAATTTGACCTAGATTCTGCTTTGGAATGGATAAA
AAACAAAAGGTGCCTAACTGATATACAAAAAGCACTAATTGGTGCCTCTATATG
CTTTTTAAAACCCAAAGACCAAGAAAGAAAAAGGAGATTCATCACAGAGCCCCT
GTCAGGAATGGGAACAACAGCAACAAAGAAGAAAGGCCTAATTCTAGCTGAGA
GAAAAATGAGAAGATGTGTAAGCTTTCATGAAGCATTTGAAATAGCAGAAGGCC
ACGAAAGCTCAGCATTACTATATTGTCTTATGGTCATGTACCTAAACCCTGAAAA
CTATTCAATGCAAGTAAAACTAGGAACGCTCTGTGCTTTATGCGAGAAACAAGC
ATCGCACTCGCATAGAGCCCATAGCAGAGCAGCAAGGTCTTCGGTACCTGGAGT
AAGACGAGAAATGCAGATGGTTTCAGCTATGAACACAGCAAAGACAATGAATGG
AATGGGAAAGGGAGAAGACGTCCAAAAACTAGCAGAAGAGCTGCAAAACAACA
TTGGAGTGTTGAGATCTCTAGGAGCAAGTCAAAAGAATGGAGAAGGAATTGCCA
AAGATGTAATGGAAGTGCTAAAACAGAGCTCTATGGGAAATTCAGCTCTTGTGA
GGAAATACTTATAATGCTCGAACCACTTCAGATTCTTTCAATTTGTTCTTTCATTT
TATCAGCTCTCCATTTCATGGCTTGGACAATAGGGCATTTGAATCAAATAAGAAG
AGGGGTAAACCTGAAAATACAAATAAGGAATCCAAATAAGGAGGCAATAAACA
```

TABLE 2-continued

Wild-type BM1 and BM2 coding sequences.

```
GAGAGGTGTCAATTCTGAGACACAATTACCAAAAGGAAATCCAAGCCAAAGAAA
CAATGAAGAAAATACTCTCTGACAACATGGAAGTATTGGGTGACCACATAGTAG
TTGAAGGGCTTTCAACTGATGAGATAATAAAAATGGGTGAAACAGTTTTGGAGG
TGGAAGAATTGCAATGAGCCCAATTTTCACTGTATTTCTTACTATGCATTTAAGC
AAATTGTAATCAATGTCAGTGAATAAAACTGGAAAAAGTGCGTTGTTTCTACT
```

The amino acid sequences for wild-type BM1 and BM2 and the amino acid sequence for a BM1 M86V mutant are provided in Table 3.

TABLE 3

Amino acid sequences of segment 7 encoded proteins of wild-type influenza B viruses.

BM1 influenza B/Lee/1940 (SEQ ID NO: 8)
NH2-
MSLFGDTIAYLLSLIEDGEGKAELAEKLHCWFGGKEFDLDSALEWIKNKRCLTDIQK
ALIGASICFLKPKDQERKRRFITEPLSGMGTTATKKKGLILAERKMRRCVSFHEAFEIA
EGHESSALLYCLMVMYLNPENYSMQVKLGTLCALCEKQASHSHRAHSRAARSSVP
GVRREMQMVSAMNTAKTMNGMGKGEDVQKLAEELQNNIGVLRSLGASQKNGEGI
AKDVMEVLKQSSMGNSALVRKYL
-COOH BM1 influenza B/Florida/4/2006 (SEQ ID NO: 9)
NH2-
MSLFGDTIAYLLSLTEDGEGKAELAEKLHCWFGGKEFDLDSALEWIKNKRCLTDIQK
ALIGASICFLKPKDQERKRRFITEPLSGMGTTATKKKGLILAERKMRRCVSFHEAFEIA
EGHESSALLYCLMVMYLNPGNYSMQVKLGTLCALCEKQASHSHRAHSRAARSSVP
GVRREMQMVSAMNTAKTMNGMGKGEDVQKLAEELQSNIGVLRSLGASQKNGEGI
AKDVMEVLKQSSMGNSALVKKYL
-COOH BM1 M86V influenza B/Florida/4/2006 (SEQ ID NO: 10)
NH2-
MSLFGDTIAYLLSLTEDGEGKAELAEKLHCWFGGKEFDLDSALEWIKNKRCLTDIQK
ALIGASICFLKPKDQERKRRFITEPLSGVGTTATKKKGLILAERKMRRCVSFHEAFEIA
EGHESSALLYCLMVMYLNPGNYSMQVKLGTLCALCEKQASHSHRAHSRAARSSVP
GVRREMQMVSAMNTAKTMNGMGKGEDVQKLAEELQSNIGVLRSLGASQKNGEGI
AKDVMEVLKQSSMGNSALVKKYL
-COOH
BOLD UNDERLINE = Mutant M86V Residue BM2 influenza B/Lee/1940 (SEQ ID NO: 11)
NH2-
MLEPLQILSICSFILSALHFMAWTIGHLNQIRRGVNLKIQIRNPNKEAINREVSILRHNY
QKEIQAKETMKKILSDNMEVLGDHIVVEGLSTDEIIKMGETVLEVEELQ
-COOH BM2 influenza B/Florida/4/2006 (SEQ ID NO: 12)
NH2-
MLEPFQILSICSFILSALHFVAWTIGHLNQIKRGVNMKIRIKGPNKETINREVSILRHSY
QKEIQAKEAMKEVLSDNMEVLSDHIVIEGLSAEEIIKMGETVLEVEELH
-COOH The first construct, called BM2SR-1 (SEQ ID NO: 1), is the complete deletion of the BM2 ORF like previously reported by Hatta, et al., J. Virol. 83(11): 5939-5942 (2009), which corresponds to BM2SR-0 (SEQ ID NO: 6), but encodes a modern protein rather than the BM1 of B/Lee/1940.

Figure 17B:
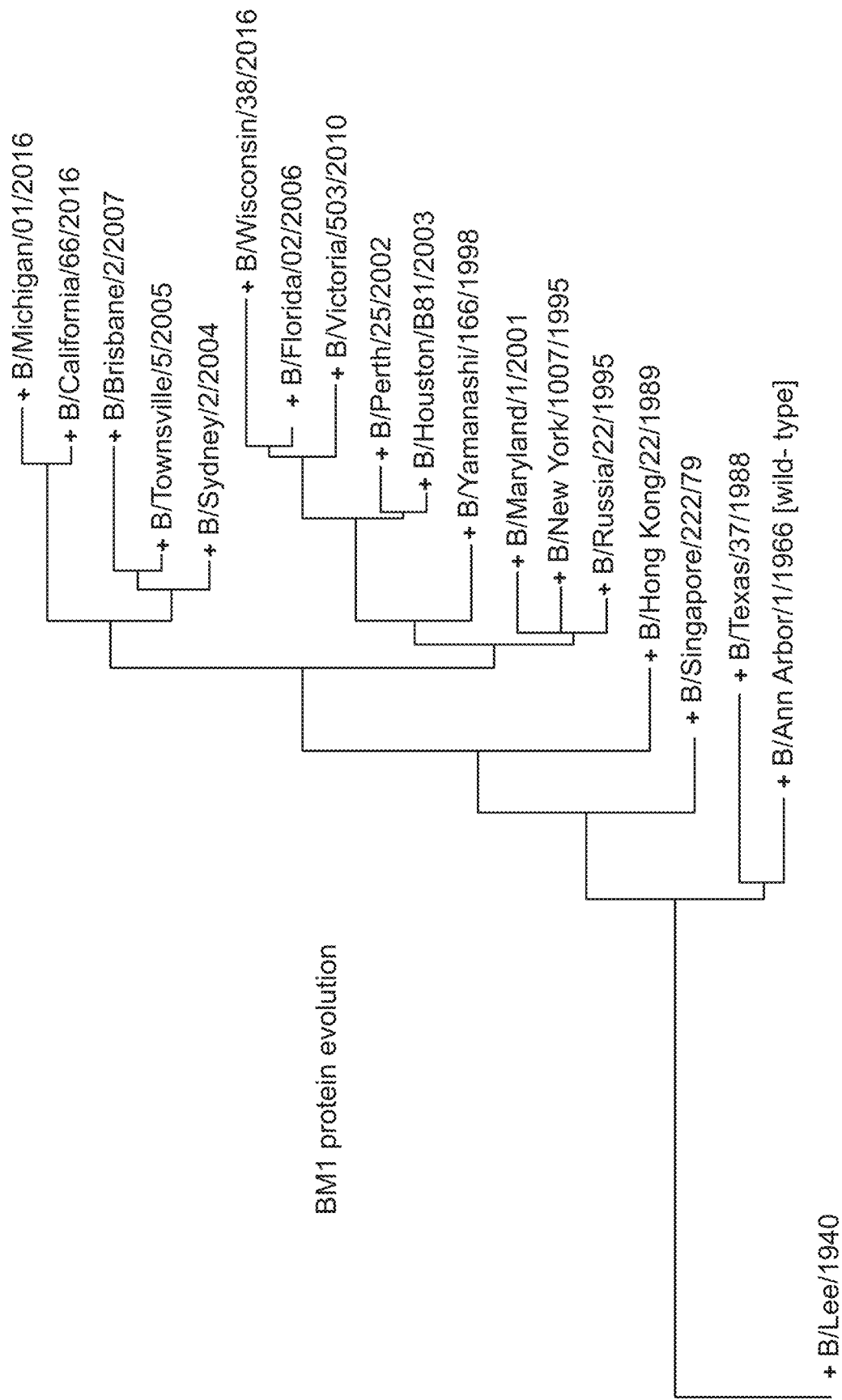

Two antigenically and genetically distinct lineages of influenza B viruses have co-circulated and caused disease in humans since at least 1988. Influenza viruses of the Victoria lineage were the predominant type B strains circulating worldwide in the 1980s with the Yamagata lineage becoming the dominant type B virus in the early 1990s. Since 1991, Victoria lineage viruses have been isolated infrequently and limited almost entirely to eastern Asia. Victoria viruses reemerged in 2002, and both Yamagata and Victoria lineages have coexisted since. Evolutionary relationships of influenza B viruses isolated from 1940 to 2016 indicate that the BM1 and BM2 proteins of modern isolates are more closely related to each other than to B/Lee/40. The phylogenetic relationships are shown in FIGS. 17A and 17B.

The BM2SR-2 construct (SEQ ID NO: 2) restores the BM1-BM2 pentanucleotide stop-start site and the native 3'-sequence context to improve BM1 expression and regulation. A five nucleotide sequence in the FluB mRNA, TAATG, encodes a ribosome slippage sequence called the pentanucleotide stop-start site that contains both the stop codon TAA of the upstream BM1 ORF and the start codon ATG of the downstream frame-shifted BM2 ORF. The native RNA sequence context both 5' and 3' of this sequence contains elements that regulate translation of BM1 protein expression. Restoration of the pentanucleotide necessitates restoration of the BM2 start codon and in native context. Thus, translation is expected to re-initiate at the BM2 ATG site. To block expression of any sequences 3' of the region, an artificial sequence was inserted into BM2SR-2 that encodes 3 stop codons in tandem, one in each potential translational open reading frame downstream.

Figure 3:
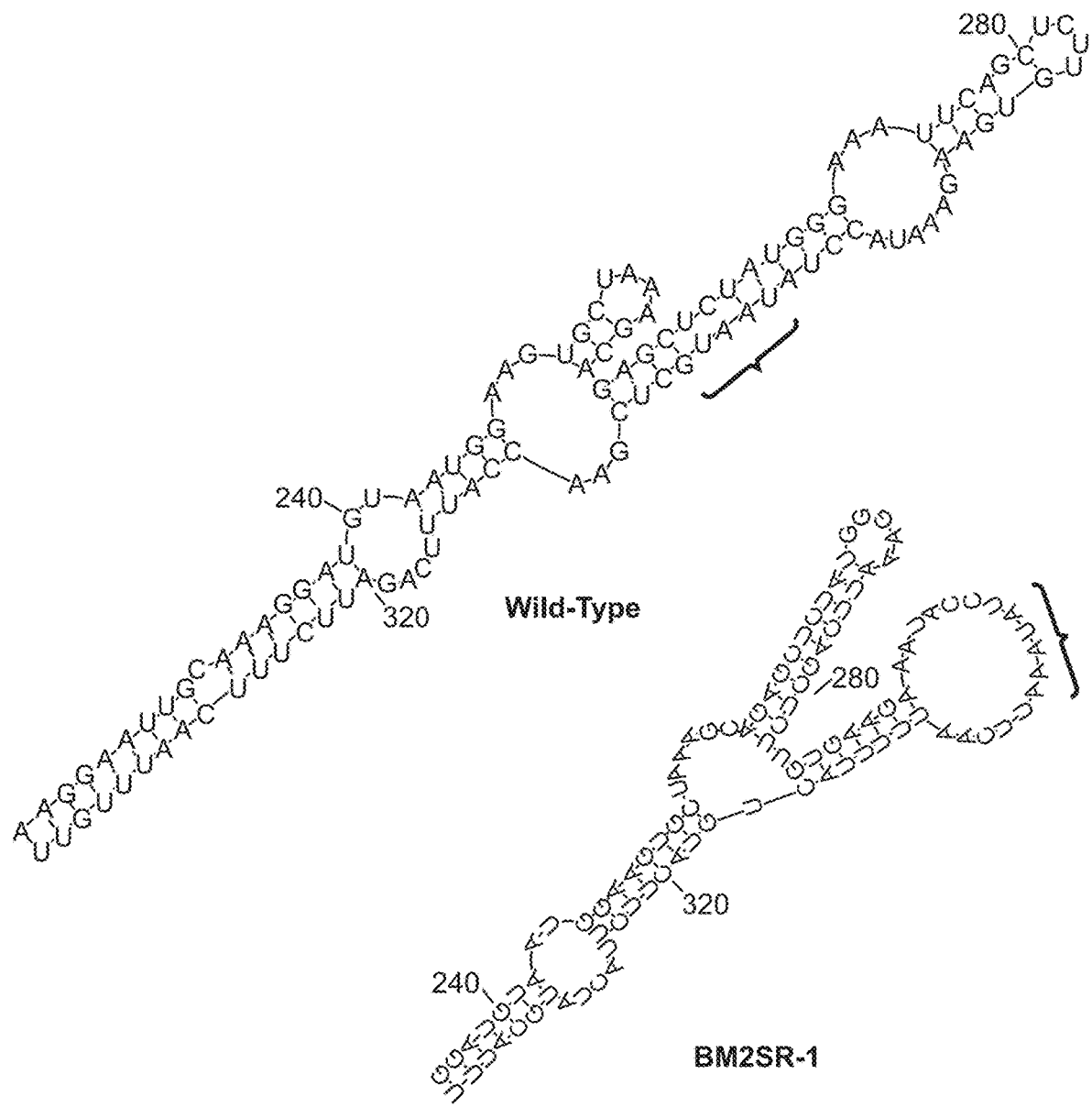
FIG. 3 shows folding models of the influenza B segment 7 mRNA pentanucleotide region modeled using the MFold RNA folding algorithm. The pentanucleotide translational stop-start region is indicated by a bracket. The wild-type model comprises the influenza genomic segment 7 of B/FL/04/2006. The BM2SR-1 mutant comprises a complete deletion of the BM2 open reading frame (ORF). The BM2SR-2 mutant comprises a BM2 deletion with the M1 translational regulatory elements intact.
Figure 3:
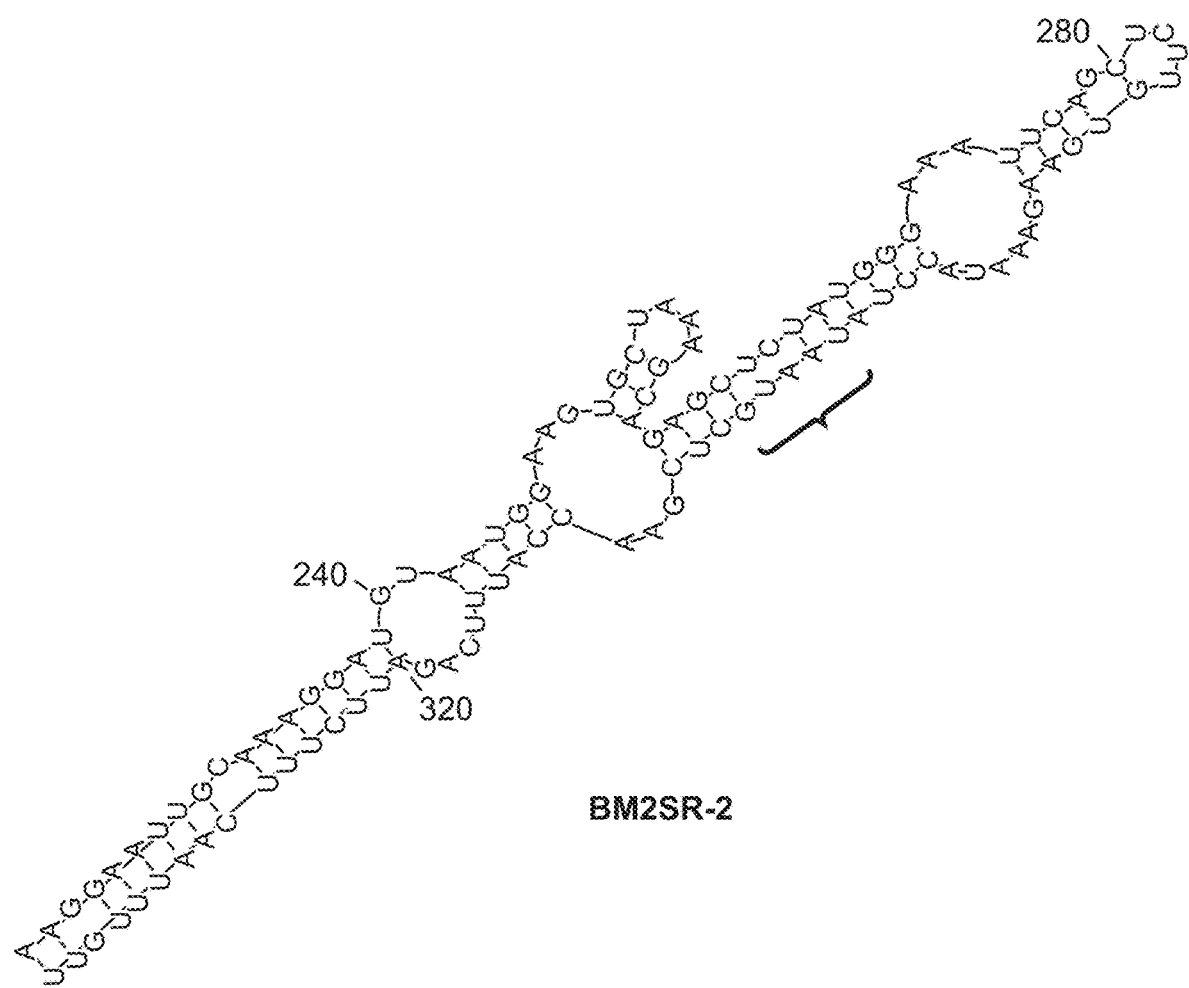

The B/Florida/4/2006 wild-type segment 7 as well as BM2SR-1 and BM2SR-2 were modeled using the MFold RNA folding algorithm. The region surrounding the BM2SR-2 pentanucleotide was predicted to fold into an RNA structure similar to that wild-type while the BM2SR-1 mutant with complete BM2 ORF deletion including 2 bp of the pentanucleotide was not (FIG. 3). Thus, addition of 32 bp to the BM2SR-2 construct is predicted by the thermodynamic MFold model to promote normal RNA structure.

The BM2SR-3 construct (SEQ ID NO: 3) is identical to BM2SR-2 with a single mutation: incorporation of a valine in place of the absolutely-conserved methionine at amino acid 86 in the influenza B M1 gene (M1 M86V). The substitution of M86V is known to improve the growth of wild-type influenza B strains in Vero cells (N. Wressnigg et al., Vaccine 27:2851-2857 (2009)).

The BM2SR-4 construct (SEQ ID NO: 4) is a smaller deletion from M2 of only 90 bp that is based upon the observation that alterations of the segment sizes of the genomic RNAs can have negative impact on stability of the virus segment. This has been attributed to sequences near the 5' end of the genomic RNA that fall within the coding region of the viral proteins (Hatta et al. (2009)). This is likely to be the case for the M2 ORF located proximal to the 5' end of genomic segment 7 (3' end of mRNA). Segment instability can cause increases in the number of defective virus particles lacking a given segment with attenuated viral growth and reduced final viral titer (Hutchinson et al., J. Virol. 82:11869-11879 (2008)). The 90-bp deletion from BM2SR-4 represents less than 8% the total native length of 1190 bp for segment 7.

The BM2SR-5 construct (SEQ ID NO: 5) is a combination of all the segment 7 improvements: smaller deletion from M2 for segment stability, M1 translation regulation for M1 expression, and M1 M86V mutation to improve virus titer and growth in the Vero cell substrate.

The BM2SR-1 and BM2SR-3 mutants do not express a BM2 polypeptide. The BM2SR-2, BM2SR-4, and BM2SR-5 mutants could potentially express a truncated polypeptide comprising the first eleven amino acids of the BM2 protein; however, this has not yet been demonstrated.

IV. Cell-Based Virus Production System

A. Producing "First Generation" Mutant Viruses and Virus Reverse Genetics

Mutant virus, such as those carrying mutant BM2 nucleic acid, can be generated by plasmid-based reverse genetics as described by Neumann et al., Proc. Natl. Acad. Sci. USA 96:9345-9350 (1999). Briefly, eukaryotic host cells are transfected with one or more plasmids encoding the eight viral RNAs, corresponding to each of the eight influenza B segments. Each viral RNA sequence is flanked by an RNA polymerase I promoter and an RNA polymerase I terminator. Notably, the viral RNA encoding the BM2 protein includes the mutant BM2 nucleic acid sequence. The host cell is additionally transfected with one or more expression plasmids encoding the viral proteins (e.g., polymerases, nucleoproteins, and structural proteins), including a wild-type BM2 protein. Transfection of the host cell with the viral RNA plasmids results in the synthesis of all eight influenza viral RNAs, one of which harbors the mutant BM2 sequence. The co-transfected viral polymerases and nucleoproteins assemble the viral RNAs into functional vRNPs that are replicated and transcribed, ultimately forming infectious influenza virus having a mutant BM2 nucleic acid sequence, yet having a functional BM2 polypeptide incorporated into the viral lipid envelope.

For example, in BM2SR mutants based upon the B/FL/04/2006 segment 7 and a B/Lee/1940 control, BM2-deleted segment 7 were inserted into standard influenza reverse genetics plasmid vectors and used to generate vaccine-candidate influenza B viruses with HA and NA combinations from modern Victoria and Yamagata lineage segments 4 and 6. Segments 1, 2, 3, 5, and 8, encoding internal gene products including but not limited to PB1, PB2, PA, NP, NS1 and NS2, were derived from B/Lee/40. Recombinant viruses were generated by chemically-mediated transfection into 293T cells. Recovery of 293T-generated, BM2-deficient mutant viruses was performed in Madin-Darby Canine Kidney (MDCK) cells that constitutively express BM2 protein (i.e., BM2CK cells).

Twelve BM2-deficient, influenza B BM2SR mutant viruses described in Table 4 were constructed. B/Lee/40-0, B/FL/04/2006-1, B/FL/04/2006-2, B/FL/04/2006-3, B/FL/04/2006-4, and B/FL/04/2006-5 as shown in Table 4 correspond to BM2SR-0, BM2SR-1, BM2SR-2, BM2SR-3, BM2SR-4, and BM2SR-5, respectively.

TABLE 4

Influenza B BM2SR Mutant Virus Genotypes

| Segment (Number) | HA:NA (4, 6) | BM2SR (7) | Internal Genes (1, 2, 3, 5, 8) |
|---|---|---|---|
| | B/Brisbane/ 60/2008 | B/Lee/40-0 B/FL/04/2006-1 B/FL/04/2006-2 B/FL/04/2006-3 B/FL/04/2006-4 B/FL/04/2006-5 | B/Lee/40 |
| | B/Wisconsin/ 01/2010 | B/Lee/40-0 B/FL/04/2006-1 B/FL/04/2006-2 B/FL/04/2006-3 B/FL/04/2006-4 B/FL/04/2006-5 | |

Alternative methods of producing a "first generation" mutant virus include a ribonucleoprotein (RNP) transfection system that allows the replacement of influenza virus genes with in vitro generated recombinant RNA molecules, as described by Enami & Palese, J. Virol. 65(5):2711-2713 (1991).

The viral RNA is synthesized in vitro and the RNA transcripts are coated with viral nucleoprotein (NP) and polymerase proteins that act as biologically active RNPs in the transfected cell as demonstrated by Luytjes et al., Cell 59:1107-1113 (1989).

The RNP transfection method can be divided into four steps: 1) Preparation of RNA: plasmid DNA coding for an influenza virus segment is transcribed into negative-sense RNA in an in vitro transcription reaction; 2) Encapsidation of the RNA: the transcribed RNA is then mixed with gradient purified NP and polymerase proteins isolated from disrupted influenza virus to form a biologically active RNP complex; 3) Transfection and rescue of the encapsidated RNA: the artificial ribonucleocapsid is transfected to the cells previously infected with a helper influenza virus that contains a different gene from the one being rescued; the helper virus will amplify the transfected RNA; 4) Selection of transfected gene: because both the helper virus and the transfectant containing the rescued gene are in the culture supernatant, an appropriate selection system using antibodies is necessary to isolate the virus bearing the transfected gene.

The selection system allows for the generation of novel transfectant influenza viruses with specific biological and molecular characteristics. Antibody selection against a target surface protein can then be used for positive or negative selection.

Additionally or alternatively, the same antibodies can be used to 'capture' the helper virus and allow for the enrichment of the transfectant. For example, the antibodies can be used to coat the bottom of a tissue culture dish or can be used in a column matrix to allow for enrichment for the transfectant in the supernatant or eluate.

The transfectant virus can be grown in BM2 expressing cells in multi-well plates by limit dilution and then be identified and cloned, for example, by creating replica plates. For example, one-half of an aliquot of a given well of the multi-well plate containing the grown virus can be used to infect MDCK cells and the other half to infect MDCK cells that express BM2 protein (i.e., BM2CK cells). Both the transfectant virus and helper virus will grow in MDCK cells that express BM2 protein. However, only helper virus will grow in standard MDCK cells allowing for identifying the well in the multi-well plate that contains the transfectant. The transfectant virus can be further plaque purified in the cells that express BM2 protein.

B. Propagating Viral Mutants

In some embodiments, viral mutants described herein are maintained and passaged in host cells. By way of example, but not by way of limitation, exemplary host cells appropriate for growth of influenza viral mutants, such as influenza B viral mutants include any number of eukaryotic cells, including, but not limited to Madin-Darby canine kidney cells (MDCK cells), simian cells such as African green monkey cells (e.g., Vero cells), CV-1 cells and rhesus monkey kidney cells (e.g., LLcomk.2 cells), bovine cells (e.g., MDBK cells), swine cells, ferret cells (e.g., mink lung cells) BK-1 cells, rodent cells (e.g., Chinese Hamster Ovary cells), human cells, e.g., embryonic human retinal cells (e.g., PER-C6®), 293T human embryonic kidney cells and avian cells including embryonic fibroblasts.

Additionally or alternatively, in some embodiments, the eukaryotic host cell is modified to enhance viral production, e.g., by enhancing viral infection of the host cell and/or by enhancing viral growth rate. For example, in some embodiments, the host cell is modified to express, or to have increased expression, of 2,6-linked sialic acid on the cell surface, allowing for more efficient and effective infection of these cells by mutant or wild-type influenza B viruses. See, e.g., U.S. Patent Publication No. 2010-0021499, and U.S. Pat. No. 7,176,021. Thus, in some illustrative embodiments, Chinese Hamster Ovary Cells (CHO cells) and/or Vero cells modified to express at least one copy of a 2,6-sialyltransferase gene (ST6GAL 1) are used. By way of example, but not by way of limitation, the Homo sapiens ST6 beta-galatosamide alpha-2,6-sialyltransferase gene sequence denoted by the accession number BC040009.1, is one example of a ST6Ga1 gene that can be integrated into and expressed by a CHO cell. One or more copies of a polynucleotide that encodes a functional ST6Ga1 I gene product can be engineered into a cell. That is, cells which have been stably transformed to express 1, 2, 3, 4, 5, 6, 7, 8, 9, 10, 11, 12, or more than 12 copies of a ST6Ga1 I gene may be used. A single expression cassette may include one or more copies of the ST6Ga1 I gene to be expressed, which is operably linked to regulatory elements, such as promoters, enhancers, and terminator and polyadenylation signal sequences, to facilitate the expression of the ST6Ga1 I gene or its copies. Alternatively, a single expression cassette may be engineered to express one copy of an ST6Ga1 I gene, and multiple expression cassettes integrated into a host cell genome. Accordingly, in some embodiments, at least one ST6Ga1 I gene is incorporated into the genome of a host cell, such that the cell expresses the ST6Ga1 I gene and its enzymatic protein product. Depending on the copy number, a single host cell may express many functional ST6Ga1 I gene proteins.

Suitable vectors for cloning, transfecting and producing stable, modified cell lines are well known in the art. One non-limiting example includes the pcDNA3.1 vectors (Invitrogen).

Additionally or alternatively, in some embodiments, the eukaryotic host cell is modified to produce a wild-type version of a mutant viral gene, thereby providing the gene to the virus in trans. For example, a viral strain harboring a mutant BM2 protein may exhibit an enhanced growth rate (e.g., greater viral production) when passaged in host cells producing the wild-type BM2 protein. In some embodiments, the viral strain harboring a mutant BM2 protein may not grow or replicate in a cell which does not express a wild-type BM2 gene. In addition, such host cells may slow or prevent viral reversion to a functional BM2 sequence, because, for example, there is no selective pressure for reversion in such a host.

Methods for producing both expression vectors and modified host cells are well known in the art. For example, a BM2 expression vector can be made by positioning the BM2 nucleic acid sequence (BM2 ORF sequence; that is, "wild-type" BM2's start codon to stop codon (Table 5)) below in a eukaryotic expression vector.

TABLE 5

Wild-type BM2 nucleic acid sequence (SEQ ID NO: 13)

ATGCTCGAACCACTTCAGATTCTTTCAATTTGTTCTTTCATTTTATCAGCTCTCCAT
TTCATGGCTTGGACAATAGGGCATTTGAATCAAATAAGAAGAGGGGTAAACCTG
AAAATACAAATAAGGAATCCAAATAAGGAGGCAATAAACAGAGAGGTGTCAAT
TCTGAGACACAATTACCAAAAGGAAATCCAAGCCAAAGAAACAATGAAGAAAA
TACTCTCTGACAACATGGAAGTATTGGGTGACCACATAGTAGTTGAAGGGCTTTC
AACTGATGAGATAATAAAAATGGGTGAAACAGTTTTGGAGGTGGAAGAATTGCA
ATGAGCCCAATTTTCACTGTATTTCTTACTATGCATTTAAGCAAATTGTAATCAAT
GTCAGTGAATAAAACTGGAAAAAGTGCGTTGTTTCTACT

Host cells (e.g., MDCK cells, Vero cells) can then be transfected by methods known in the art, e.g., using commercially available reagents and kits. By way of example, but not by way of limitation, cells can be selected and tested for BM2 expression by cotransfection with a detectable marker or a selectable marker (e.g., hygromycin-resistance) and/or by screening, for example, with indirect immunostaining using a BM2 antibody. BM2 expression can be determined by indirect immunostaining, flow cytometry or ELISA.

In some embodiments, cells and viral mutants are cultured and propagated by methods well known in the art. By way of example, but not by way of limitation, in some embodiments, host cells are grown in the presence of MEM supplemented with 10% fetal calf serum. Cells expressing BM2 are infected at an MOI of 0.001 by washing with PBS followed by adsorbing virus at 37° C. In some embodiments, viral growth media containing trypsin/TPCK is added and the cells are incubated for 2-3 days until cytopathic effect is observed.

Along these lines, disposable bioreactor systems have been developed for mammalian cells, with or without virus, whose benefits include faster facility setup and reduced risk of cross-contamination. The cells described herein, for instance, can be cultured in disposable bags or single use bioreactors from HyClone or Celltainer from Lonza. Bioreactors can be 1 L, 10 L, 50 L, 250 L, 1000 L size formats. In some embodiments, the cells are maintained in suspension in optimized serum free medium, free of animal products. The system can be a fed-batch system where a culture can be expanded in a single bag from 1 L to 10 L, for example, or a perfusion system that allows for the constant supply of nutrients while simultaneously avoiding the accumulation of potentially toxic by-products in the culture medium.

For long term storage, mutant virus can be stored as frozen stocks.

V. BM2-Expressing Cell Lines

A. Growth of M2-Deficient Influenza a and BM2-Deficient Influenza B Strains in BM2-Expressing Cell Substrate As described above, BM2 is an integral membrane protein that is incorporated into influenza B virion envelopes. Electrophysiological studies have demonstrated that BM2 has proton ($H^+$) ion channel activity as a functional counterpart of the influenza A virus M2 protein. Mould, et al., *Dev. Cell* 5:175-184 (2003). The influenza M2 protein is required for replication in both the influenza A and influenza B viruses (Watanabe, S., et al. *J. Virol.* 83:5947-5950 (2009)). Deletion or mutation of the open reading frame (ORF) encoding the M2 ion channel within influenza A or influenza B genomic RNA segment 7 causes a failure in virus maturation that completely blocks release of progeny particles from any infected cell.

Inactivating mutations in M2 can be complemented in trans by M2 proteins encoded within the genome of cell lines engineered to stably express influenza A or influenza B M2 cDNAs. Expression of the wild-type A/PR/8/1934 M2 (SEQ ID NO: 23) and the B/Lee/40 BM2 (SEQ ID NO: 24) cDNAs allow M2-deficient mutant A viruses (M2SRs) and BM2-deficient mutant B viruses (BM2SRs) to replicate. For example, this can be demonstrated in modified Madin-Darby Canine Kidney (MDCK) cell lines known as M2CK (FluA) cells and BM2CK (FluB) cells that employ the strong synthetic CAG promoter (Miyazaki, J; Takaki, S; Araki, K; Tashiro, F; Tominaga, A; Takatsu, K; Yamamura, K (Jul. 15, 1989)). "Expression vector system based on the chicken beta-actin promoter directs efficient production of interleukin-5.". Gene. 79 (2): 269-77) to drive high-level constitutive expression of the A/PR/8 M2 and B/Lee/40 BM2 proteins, respectively. To determine whether influenza A M2 and influenza B M2 proteins can complement M2-deficient influenza A and/or BM2-deficient B viruses, a standard 50% tissue culture infectious dose ($TCID_{50}$) assay (WHO) can be used according to methods known in the art.

Accordingly, in some embodiments, the present disclosure provides a BM2CK cell line that supports the growth of both BM2-deficient influenza B viruses (i.e., BM2SR viruses) and M2-deficient influenza A viruses (i.e., M2SR viruses). In some embodiments, influenza A mutants deficient in M2 are grown in BM2CK cells in which BM2 is supplemented in trans. In some embodiments, the BM2CK cells described herein complement and support the growth of influenza A M2-deficieint M2SR viral strains.

In some embodiments, influenza B mutants deficient in BM2 are grown in M2CK cells in which M2 is supplemented in trans. In some embodiments, the M2CK cells described herein complement and support the growth of influenza B M2-deficient BM2SR viral strains.

B. Chimeric M2 Proteins

The rescue of influenza B BM2-deficient BM2SR viruses by reverse genetics (RG) requires that the BM2 protein be supplied in trans within the recipient cell substrate. However, the 293T cells that are most often employed for high-efficiency RG lack BM2 expression. Therefore, BM2SR viruses are typically generated in 293T by supplying a $13^{th}$ plasmid encoding the BM2 protein along with the standard 12 plasmid influenza RG system encoding the flu replicase (4) and genomic RNAs (8) used as previously described. See, e.g., Hatta & Kawaoka, *J. Virol.* 77:6050-6054 (2003); Neumann et al., *Proc. Natl. Acad. Sci. USA* 96:9345-9350 (1999).

M2 proteins can be divided into three domains: 1) an extracellular or ectodomain; 2) a transmembrane (TM) domain; and 3) an intracellular cytoplasmic or endodomain (FIG. 10).

The extracellular domain of influenza A M2 is about 24 to 27 amino-acids in length, has a known structure, and encodes the 14C2 epitope as compared to only 6 to 9 residues for the BM2 domain that is not known to be antigenic or to have a well-defined structure (Cross, *Nature Structural & Molecular Biology* 16:1207-1209 (2009)). The initial 9 amino acids of the influenza A M2 extracellular domain are identical to the N-terminus of M1 protein as they are encoded in a shared exon that is differentially spliced to make M2. This arrangement is not present in influenza B and thus BM1 and BM2 do not share protein sequence identity.

The transmembrane (TM) domains in both influenza A and B encode pH-dependent proton channels about 22-24 residues long that contain a canonical 19 amino acid structures with histidine and tryptophan residues of identical spacing that have been shown to be required for channel function. The TM domain of influenza A M2 is the target for amantadine, a therapeutic channel inhibitor, while BM2 is not.

The endodomain of BM2 is larger at about 81 to 83 amino acids in length compared to about 47 to 51 for influenza A M2. Both endodomains are extremely hydrophilic with spatially separate highly-charged acidic and basic regions. Indeed, the BM2 endodomain has one of the largest dipole moments ever reported for a protein.

In some embodiments, the present disclosure provides for chimeric fusions of the three domains from influenza A M2 and influenza B BM2 in various permutations as shown in FIG. 10. In some embodiments, the influenza A TM domain can be split into subdomains encoding the amantadine binding site nearer the cell surface and the remainder of the TM domain. The domain structures for these mutants are given in FIG. 10. In some embodiments, a BM2 channel-null (BM2 null; BBB null) mutant that combines two amino substitutions, S12L and H19C, that have each been shown to abolish BM2 $H^+$-channel activity is provided.

The wild-type and chimeric amino acid sequences for influenza A/PR/8 M2, influenza B/Lee/40 BM2, and chimeric fusion proteins thereof are provided in Table 6.

TABLE 6

M2 and Chimeric M2 protein amino acid sequences: Influenza A/PR/8 M2, influenza B/Lee/40 BM2 and chimeric fusion proteins thereof.

A/PR/8 M2 (SEQ ID NO: 14) 97 amino acid wild-type influenza A/Puerto Rico/1934 (H1N1) M2 protein.
MSLLTEVETPIRNEWGCRCNGSSDPLTIAANIIGIL*H*LTL*W*ILDRLFFKCIYRRFKYGLK
GGPSTEGVPKSMREEYRKEQQSAVDADDGHFVSIELE
UPPER CASE = M2 Protein
UNDER LINE = Transmembrane Domain
*UPPER CASE ITALICS* = Canonical Proton Channel Residues B/Lee/40 BM2 (SEQ ID NO: 15) 109 amino acid wild-type influenza B/Lee/1940 BM2 protein.
**MLEPLQILSICSFILSAL*H*FMA*W*TIGHLNQIRRGVNLKIQIRNPNKEAINREVSILR**
HNYQKEIQAKETMKKILSDNMEVLGDHIVVEGLSTDEIIKMGETVLEVEELQ
BOLD UPPER CASE = BM2 Protein
BOLD UNDER LINE = BM2 Transmembrane Domain
*UPPER CASE ITALICS* = Canonical Proton Channel Residues BM2 Null (SEQ ID NO: 16) 109 amino acid influenza B/Lee/1940 BM2 protein with Null Channel Mutation.

**MLEPLQILSICSFILSAL*C*FMA*W*TIGHLNQIRRGVNLKIQIRNPNKEAINREVSILR**

HNYQKEIQAKETMKKILSDNMEVLGDHIVVEGLSTDEIIKMGETVLEVEELQ
BOLD UPPER CASE = BM2 Protein
BOLD UNDER LINE = BM2 Transmembrane Domain
*UPPER CASE ITALICS* = Canonical Proton Channel Residues BOXED TEXT = His 19Cys Proton Channel Null Mutation ABB influenza M2 (SEQ ID NO: 17) Chimeric 127 amino acid M2 protein: influenza A M2 Ectoplasmic Domain + influenza B M2 Transmembrane Domain + influenza BM2 Cytoplasmic Domain.
MSLLTEVETPIRNEWGCRCNGSSDPLS**ICSFILSAL*H*FMA*W*TIGHLNQIRRGVNLKI**
QIRNPNKEAINREVSILRHNYQKEIQAKETMKKILSDNMEVLGDHIVVEGLSTDE
IIKMGETVLEVEELQ
UPPER CASE = Influenza A M2 Protein
BOLDNDER LINE = BM2 Transmembrane Domain
BOLD UPPER CASE = BM2 Protein
*UPPER CASE ITALICS* = Canonical Proton Channel Residues AAB influenza M2 (SEQ ID NO: 18) Chimeric 127 amino acid M2 protein: influenza A M2 Ectoplasmic Domain + influenza A M2 Transmembrane Domain + influenza BM2 Cytoplasmic Domain.
MSLLTEVETPIRNEWGCRCNGSSDPLTIAANIIGIL*H*LTL*W*ILDRLNQIRRGVNLKIQI
RNPNKEAINREVSILRHNYQKEIQAKETMKKILSDNMEVLGDHIVVEGLSTDEDI
KMGETVLEVEELQ
UPPER CASE = Influenza A M2 Protein
UNDER LINE = Influenza A Transmembrane Domain
BOLD UPPER CASE = BM2
*UPPER CASE ITALICS* = Canonical Proton Channel Residues AA'B influenza M2 (SEQ ID NO: 19) Chimeric 127 amino acid M2 protein: influenza A M2 Ectoplasmic Domain + influenza A M2 Transmembrane Domain Portion + influenza BM2 Transmembrane Domain Portion + influenza BM2 Cytoplasmic Domain.
MSLLTEVETPIRNEWGCRCNGSSDPLTIAANIGIL*H***FMA*W*TIGHLNQIRRGVNLKIQI**
RNPNKEAINREVSILRHNYQKEIQAKETMKKILSDNMEVLGDHIVVEGLSTDEII
KMGETVLEVEELQ
UPPER CASE = Influenza A M2 Protein
UNDER LINE = A M2-BM2 Chimeric Transmembrane Domain
BOLD UPPER CASE = BM2
*UPPER CASE ITALICS* = Canonical Proton Channel Residues BAB influenza M2 (SEQ ID NO: 20) Chimeric 109 amino acid M2 protein: influenza B M2 Ectoplasmic Domain + influenza A M2 Transmembrane Domain + influenza BM2 Cytoplasmic Domain.
MLEPLQILTIAANIIGIL*H*LTL*W*ILDRLNQIRRGVNLKIQIRNPNKEAINREVSILRH
NYQKEIQAKETMKKILSDNMEVLGDHIVVEGLSTDEIIKMGETVLEVEELQ
UPPER CASE = Influenza A M2 Protein
UNDER LINE = Influenza A M2 Transmembrane Domain
BOLD UPPER CASE = BM2
*UPPER CASE ITALICS* = Canonical Proton Channel Residues TABLE 6-continued

M2 and Chimeric M2 protein amino acid sequences: Influenza A/PR/8 M2, influenza B/Lee/40 BM2 and chimeric fusion proteins thereof.

BBA influenza M2 (SEQ ID NO: 21) Chimeric 79 amino acid M2 protein: influenza BM2 Ectoplasmic Domain + influenza BM2 Trans TABLE 7-continued cDNA sequences encoding M2 and Chimeric M2 protein amino acid sequences: Influenza
A/PR/8 M2, influenza B/Lee/40 BM2, codon-optimized Influenza A/PR/8 M2, codon-
optimized influenza B/Lee/40 BM2, and codon-optimized chimeric fusion proteins thereof.

TCAAGTATGGACTGAAAGGAGGACCAAGCACAGAGGGAGTGCCTAAATCCATGA
GGGAGGAATACCGCAAAGAGCAGCAGAGCGCCGTGGACGCAGATGATGGACAT
TTCGTGAGCATTGAACTGGAAtga
UNDER LINE = Start Codon
Small Case= Stop Codon BM2 OPT (SEQ ID NO: 27) codon-optimized wild-type influenza B/Lee/1940 BM2 cDNA.
5'<u>ATG</u>**CTGGAACCACTGCAGATCCTGAGTATTTGCTCTTTTATCCTGAGCGCA
CTGCACTTTATGGCCTGGACTATCGGGCACCTGAACCAGATCAGAAGGGGC
GTGAACCTGAAGATCCAGATCAGAAACCCAAACAAGGAGGCCATCAACCGC
GAAGTGAGCATCCTGAGACACAATTACCAGAAGGAGATCCAGGCTAAAGAA
ACCATGAAGAAAATCCTGTCTGACAATATGGAGGTGCTGGGCGATCACATC
GTGGTGGAAGGACTGAGCACCGACGAAATCATCAAAATGGGCGAGACTGTC
CTGGAAGTGGAAGAACTGCAGtaa**
BOLD UNDER LINE = BM2 Start Codon
Bold Small Case = BM2 Stop Codon ABB M2 OPT (SEQ ID NO: 28): cDNA Encoding Codon-Optimized, Chimeric M2 protein:
influenza A M2 Ectoplasmic Domain + influenza BM2 Transmembrane Domain + influenza
BM2 Cytoplasmic Domain.
<u>ATG</u>TCCCTGCTGACCGAAGTGGAAACTCCTATTAGAAACGAGTGGGGCTGTAGA
TGTAACGGCTCAAGCGACCCTCTGACCATTGCTGCCAACATCATTGGCATCCTGC
ACCTGACCCTGTGGATTCTGGACCGACTG**AACCAGATCAGAAGGGGCGTGAAC
CTGAAGATCCAGATCAGAAACCCAAACAAGGAGGCCATCAACCGCGAAGTG
AGCATCCTGAGACACAATTACCAGAAGGAGATCCAGGCTAAAGAAACCATG
AAGAAAATCCTGTCTGACAATATGGAGGTGCTGGGCGATCACATCGTGGTG
GAAGGACTGAGCACCGACGAAATCATCAAAATGGGCGAGACTGTCCTGGAA
GTGGAAGAACTGCAGtaa**
UPPER CASE = Codon-optimized A M2 cDNA
BOLD UPPER CASE = Codon-optimized BM2 cDNA
UNDER LINE = A M2 Start Codon
Bold Small Case = BM2 Stop Codon AAB M2 OPT (SEQ ID NO: 29): cDNA Encoding Codon-Optimized, Chimeric M2 protein:
influenza A M2 Ectoplasmic Domain + influenza A M2 Transmembrane Domain + influenza
BM2 Cytoplasmic Domain.
<u>ATG</u>TCCCTGCTGACCGAAGTGGAAACTCCTATTAGAAACGAGTGGGGCTGTAGA
TGTAACGGCTCAAGCGACCCTCTGACCATTGCTGCCAACATCATTGGCATCCTGC
ACCTGACCCTGTGGATTCTGGACCGACTG**AACCAGATCAGAAGGGGCGTGAAC
CTGAAGATCCAGATCAGAAACCCAAACAAGGAGGCCATCAACCGCGAAGTG
AGCATCCTGAGACACAATTACCAGAAGGAGATCCAGGCTAAAGAAACCATG
AAGAAAATCCTGTCTGACAATATGGAGGTGCTGGGCGATCACATCGTGGTG
GAAGGACTGAGCACCGACGAAATCATCAAAATGGGCGAGACTGTCCTGGAA
GTGGAAGAACTGCAGtaa**
UPPER CASE = Codon-optimized A M2 cDNA
BOLD UPPER CASE = Codon-optimized BM2 cDNA
UNDER LINE = A M2 Start Codon
Bold Small Case = BM2 Stop Codon AA2FB M2 OPT (SEQ ID NO: 30): cDNA Encoding Codon-Optimized, Chimeric M2
protein: influenza A M2 Ectoplasmic Domain + influenza A M2 Transmembrane Domain
with 2F longer + influenza BM2 Cytoplasmic Domain.
5'<u>ATG</u>TCCCTGCTGACCGAAGTGGAAACTCCTATTAGAAACGAGTGGGGCTGTAG
AT<u>GT</u>AACGGCTCAAGCGACCCTCTGACCATTGCTGCCAACATCATTGGCATCCTG
CACCTGACCCTGTGGATTCTGGACCGACTGTTCTTT**AACCAGATCAGAAGGGGC
GTGAACCTGAAGATCCAGATCAGAAACCCAAACAAGGAGGCCATCAACCGC
GAAGTGAGCATCCTGAGACACAATTACCAGAAGGAGATCCAGGCTAAAGAA
ACCATGAAGAAAATCCTGTCTGACAATATGGAGGTGCTGGGCGATCACATC
GTGGTGGAAGGACTGAGCACCGACGAAATCATCAAAATGGGCGAGACTGTC
CTGGAAGTGGAAGAACTGCAGtaa**
UPPER CASE = Codon-optimized A M2 cDNA
BOLD UPPER CASE = Codon-optimized BM2 cDNA
UNDER LINE = A M2 Start Codon
Bold Small Case = BM2 Stop Codon BAB M2 OPT (SEQ ID NO: 31): cDNA Encoding Codon-Optimized, Chimeric M2 protein:
influenza BM2 Ectoplasmic Domain + influenza A M2 Transmembrane Domain + influenza
BM2 Cytoplasmic Domain.
5'<u>ATG</u>CTCGAACCACTTCAGATTCTTTACTATTGCTGCCAACATCATTGGCATCCT
GCACCTGACCCTGTGGATTCTGGACCGACTG**AACCAGATCAGAAGGGGCGTGAA
CCTGAAGATCCAGATCAGAAACCCAAACAAGGAGGCCATCAACCGCGAAGT
GAGCATCCTGAGACACAATTACCAGAAGGAGATCCAGGCTAAAGAAACCAT
GAAGAAAATCCTGTCTGACAATATGGAGGTGCTGGGCGATCACATCGTGGT
GGAAGGACTGAGCACCGACGAAATCATCAAAATGGGCGAGACTGTCCTGGA
AGTGGAAGAACTGCAGtaa**

TABLE 7-continued cDNA sequences encoding M2 and Chimeric M2 protein amino acid sequences: Influenza
A/PR/8 M2, influenza B/Lee/40 BM2, codon-optimized Influenza A/PR/8 M2, codon-
optimized influenza B/Lee/40 BM2, and codon-optimized chimeric fusion proteins thereof.

UPPER CASE = Codon-optimized A M2 cDNA
BOLD UPPER CASE = Codon-optimized BM2 cDNA
BOLD UNDER LINE = BM2 Start Codon
Bold Small Case = BM2 Stop Codon BBA M2 OPT (SEQ ID NO: 32): cDNA Encoding Codon-Optimized, Chimeric M2 protein:
influenza BM2 Ectoplasmic Domain + influenza BM2 Transmembrane Domain + influenza
A M2 Cytoplasmic
Domain.5'ATGCTGGAACCACTGCAGATCCTGAGTATTTGCTCTTTTATCCTGA
GCGCACTGCACTTTATGGCCTGGACTATCGGGCACCTGTTCTTTAAGTGCATC
TACCGGAGATTCAAGTATGGACTGAAAGGAGGACCAAGCACAGAGGGAGTGCCT
AAATCCATGAGGGAGGAATACCGCAAAGAGCAGCAGAGCGCCGTGGACGCAGA
TGATGGACATTTCGTGAGCATTGAACTGGAAtga
UPPER CASE = Codon-optimized A M2 cDNA
BOLD UPPER CASE = Codon-optimized BM2 cDNA
BOLD UNDER LINE = BM2 Start Codon
small case = A M2 Stop Codon As described herein, in some embodiments, Vero cells are modified to produce wild-type A M2 protein (SEQ ID NO: 14), wild-type BM2 protein (BBB (SEQ ID NO: 15)), or BM2 chimeric protein (e.g., ABB (SEQ ID NO. 17), AAB (SEQ ID NO: 18), AA'B (SEQ ID NO: 19), BAB (SEQ ID NO: 20), BBA (SEQ ID NO: 21), and BA'B (SEQ ID NO: 22)).

Methods for producing both expression plasmids and modified host cells, such as modified Vero cells, are well known in the art. For example, a chimeric M2 fusion protein expression plasmid can be made by positioning the M2 fusion protein nucleic acid sequence (e.g., codon-optimized BBA (SEQ ID NO: 32)) in a eukaryotic expression plasmid.

Vero cells can then be transfected by methods known in the art, e.g., using commercially available reagents and kits. By way of example, but not by way of limitation, cells can be selected and tested for BM2 expression by cotransfection with a detectable marker or a selectable marker (e.g., hygromycin-resistance) and/or by screening, for example, with indirect immunostaining using a BM2 antibody. BM2 expression can be determined by indirect immunostaining, flow cytometry or ELISA.

In some embodiments, the performance of Vero host cells for the production of M2-deficient influenza A M2SR and BM2-deficient BM2SR vaccine viruses can be improved by the use and expression of engineered M2 proteins, including chimeric fusions of M2 genes from different serotypes, influenza A and influenza B. For example, in some embodiments, Vero cells expressing A M2 and BM2 chimeric proteins (e.g., ABB (SEQ ID NO: 17), AAB (SEQ ID NO: 18), BAB (SEQ ID NO: 20), BBA (SEQ ID NO: 21)) support the growth of influenza A M2SR mutants. In some embodiments, Vero cells expressing wild-type BM2 protein (BBB (SEQ ID NO: 15)) support the growth of influenza A M2SR mutants. In some embodiments, Vero cells expressing wild-type BM2 protein (BBB (SEQ ID NO: 15)) support the growth of influenza BM2SR mutants.

C. BM2 Vero Cells Support the Growth of Influenza A M2SR Mutants

Due to their capacity to support rapid replication of influenza virus to a high titer, MDCK cells are typically employed for influenza research and development. However, it is difficult to achieve regulatory approval for any biological products derived from MDCK cells as the cells themselves have been shown to be neoplastic/tumorigenic. Vero cells, on the other hand, have been approved for cell-based vaccine manufacture, such as in polio and MMR vaccines, since the 1960s.

In some embodiments, the present disclosure provides a Vero cell line that can serve as production cells for the manufacture of an M2-deficient influenza A virus. In some embodiments, the Vero cell line comprises a codon-optimized wild-type influenza B/Lee/40 BM2 nucleotide sequence (SEQ ID NO: 27) that expresses a BM2 protein. This Vero cell line is referred to herein as BM2Vero4. In some embodiments, the M2-deficient influenza A virus is A/California/07/2009pdm H1N1 M2SR (A/CA/07), which contains the H1 and N1 segments of A/California/07/2009pdm. The cDNA sequence for the influenza A M2 viral mutant is provided below in Table 8. In some embodiments, the BM2Vero4 cells produce influenza A H1N1 M2SR virus at a level that is substantially equivalent to that of MDCK cells expressing the influenza A version of the M2 protein.

TABLE 8

Influenza A M2 (SEQ ID NO: 33) M2 ectodomain + 2 stop codons + TM deletion (PR8 M
segment + 2 stops (786-791) without 792-842 (TM)); also known as "M2KOTMdel,"
"M2KOΔTM"

3'AGCAAAAGCAGGTAGATATTGAAAGatgagtcttctaaccgaggtcgaaacGTACGTACTCTC
TATCATCCCGTCAGGCCCCCTCAAAGCCGAGATCGCACAGAGACTTGAAGATGT
CTTTGCAGGGAAGAACACCGATCTTGAGGTTCTCATGGAATGGCTAAAGACAAG
ACCAATCCTGTCACCTCTGACTAAGGGGATTTTAGGATTTGTGTTCACGCTCACC
GTGCCCAGTGAGCGAGGACTGCAGCGGTAGACGCTTTGTCCAAAATGCCCTTAATG
GGAACGGGGATCCAAATAACATGGACAAAGCAGTTAAACTGTATAGGAAGCTCA
AGAGGGAGATAACATTCCATGGGGCCAAAGAAATCTCACTCAGTTATTCTGCTG
GTGCACTTGCCAGTTGTATGGGCCTCATATACAACAGGATGGGGCTGTGACCAC
TGAAGTGGCATTTGGCCTGGTATGTGCAACCTGTGAACAGATTGCTGACTCCCAG TABLE 8-continued Influenza A M2 (SEQ ID NO: 33) M2 ectodomain + 2 stop codons + TM deletion (PR8 M segment + 2 stops (786-791) without 792-842 (TM)); also known as "M2KOTMdel," "M2KOΔTM"

```
CATCGGTCTCATAGGCAAATGGTGACAACAACCAATCCACTAATCAGACATGAG
AACAGAATGGTTTTAGCCAGCACTACAGCTAAGGCTATGGAGCAAATGGCTGGA
TCGAGTGAGCAAGCAGCAGAGGCCATGGAGGTTGCTAGTCAGGCTAGACAAATG
GTGCAAGCGATGAGAACCATTGGGACTCATCCTAGCTCCAGTGCTGGTCTGAAA
AATGATCTTCTTGAAAATTTGCAGgcctatcagaaacgaatggggtgcagatgcaacggttcaagtgatTA
ATAGgatcgtctttttttcaaatgcatttaccgtcgctttaaatacggactgaaaggagggccttctacggaaggagtgccaaa
gtctatgagggaagaatatcgaaaggaacagcagagtgctgtggatgctgacgatggtcattttgtcagcatagagctggagtaa
AAAACTACCTTGTTTCTACT
```
Lower case letters = M2 sequence
UPPER CASE LETTERS = M1 sequence
BOLD, UNDERLINE = Mutant sequence (e.g., stop codons)

The M2 polypeptide sequence produced from this mutant is as follows: MSLLTEVETPIRNEWGCRCNGSSD (SEQ ID NO: 34).

D. M2 Protein Content of Influenza A M2SR Virion Produced by BM2 Vero Cells

In some embodiments, the present disclosure provides for an influenza A M2SR virus comprising an influenza A M2SR backbone expressing the HA and NA from (e.g., A/Brisbane/10 (SEQ ID NO: 33)) wherein the virus fails to express an influenza A M2 protein, but contains a BM2 protein, and methods of making the same as set forth in the examples below. In some embodiments, the BM2 Vero cells are BM2Vero4 cells expressing wild-type B/Lee/40 BM2 protein from codon-optimized cDNA (SEQ ID NO: 27).

VI. Vaccines and Method of Administration

A. Immunogenic Compositions/Vaccines

There are various different types of vaccines which can be made from the cell-based virus production system disclosed herein. The present disclosure includes, but is not limited to, the manufacture and production of live attenuated virus vaccines, single replication vaccines, replication-deficient vaccines, viral vector vaccines, inactivated virus vaccines, whole virus vaccines, split virus vaccines, virosomal virus vaccines, viral surface antigen vaccines and combinations thereof. Thus, there are numerous vaccines capable of producing a protective immune response specific for different influenza viruses where appropriate formulations of any of these vaccine types are capable of producing an immune response, e.g., a systemic immune response. Live attenuated virus vaccines have the advantage of being also able to stimulate local mucosal immunity in the respiratory tract.

In some embodiments, vaccine antigens used in the compositions described herein are "direct" antigens, i.e., they are not administered as DNA, but are the antigens themselves. Such vaccines may include a whole virus or only part of the virus, such as, but not limited to viral polysaccharides, whether they are alone or conjugated to carrier elements, such as carrier proteins, live attenuated whole microorganisms, inactivated microorganisms, recombinant peptides and proteins, glycoproteins, glycolipids, lipopeptides, synthetic peptides, or ruptured microorganisms in the case of vaccines referred to as "split" vaccines.

In some embodiments a complete virion vaccine is provided. A complete virion vaccine can be concentrated by ultrafiltration and then purified by zonal centrifugation or by chromatography. Typically, the virion is inactivated before or after purification using formalin or beta-propiolactone, for instance.

In some embodiments, a subunit vaccine is provided, which comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as that commercialized under the name TRITON X100. The hemagglutinin may also be isolated after treatment of the virions with a protease such as bromelin, then purified by standard methods.

In some embodiments, a split vaccine is provided, which comprises virions that have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

In some embodiments, inactivated influenza virus vaccines are provided. In some embodiments, the inactivated vaccines are made by inactivating the virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

Additionally or alternatively, in some embodiments, live attenuated influenza virus vaccines are provided. Such vaccines can be used for preventing or treating influenza virus infection, according to known method steps.

In some embodiments, attenuation is achieved in a single step by transfer of attenuated genes from an attenuated donor virus to an isolate or reassorted virus according to known methods (see, e.g., Murphy, *Infect. Dis. Clin. Pract.* 2:174 (1993)). In some embodiments, a virus is attenuated by mutation of one or more viral nucleic acid sequences, resulting in a mutant virus. For example, in some embodiments, the mutant viral nucleic acid sequence codes for a defective protein product. In some embodiments, the protein product has diminished function or no function. In other embodiments, no protein product is produced from the mutant viral nucleic acid.

The virus can thus be attenuated or inactivated, formulated and administered, according to known methods, as an immunogenic composition (e.g., as a vaccine) to induce an immune response in an animal, e.g., an avian and/or a mammal. Methods are well-known in the art for determining whether such attenuated or inactivated vaccines have maintained similar antigenicity to that of the clinical isolate or a high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) or other mutant sequences (e.g., M2) are not present in the attenuated viruses. See, e.g., Robertson et al., *Giornale di Igiene e Medicina Preventiva*, 29:4 (1988); Kilbourne, Bull. M2 World Health Org., 41:643 (1969); and Robertson et al., *Biologicals*, 20, 213 (1992).

In some embodiments, the vaccine includes a recombinant influenza virus that lacks expression of a functional BM2 protein. In some embodiments, the mutant virus replicates well in cells expressing BM2 proteins, but in the corresponding wild-type cells, expresses viral proteins without generating infectious progeny virions.

Pharmaceutical compositions of the present invention, suitable for intradermal administration, inoculation or for parenteral or oral administration, comprise attenuated or inactivated influenza viruses, and may optionally further comprise sterile aqueous or non-aqueous solutions, suspensions, and emulsions. The compositions can further comprise auxiliary agents or excipients, as known in the art. See, e.g., Berkow et al., The Merck Manual, 15th edition, Merck and Co., Rahway, N.J. (1987); Goodman el al., eds., Goodman and Gilman's The Pharmacological Basis of Therapeutics, Eighth Edition, Pergamon Press, Inc., Elmsford, N.Y. (1990); Avery's Drug Treatment: Principles and Practice of Clinical Pharmacology and Therapeutics, Third Edition, ADIS Press, LTD., Williams and Wilkins, Baltimore, Md. (1987); and Katzung, ed., Basic and Clinical Pharmacology, Fifth Edition, Appleton and Lange, Norwalk, Conn. (1992).

In some embodiments, preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For immunogenic compositions or vaccines, adjuvants, substances that augment a specific immune response, can be used. Normally, the adjuvant and the composition are mixed prior to presentation to the immune system, or presented separately, but into the same site of the organism being immunized.

In some embodiments, the immunogenic compositions (e.g., vaccines) disclosed herein include multiple, different types of virus or viral antigens, at least one of which includes a mutant BM2 gene (e.g., a virus comprising the BM2SR-1 (SEQ ID NO: 1), BM2SR-2 (SEQ ID NO: 2), BM2SR-3 (SEQ ID NO: 3), BM2SR-4 (SEQ ID NO: 4), or BM2SR-5 (SEQ ID NO: 5) mutation).

In some embodiments, the vaccine comprises a virus comprising the BM2SR-1 (SEQ ID NO: 1), BM2SR-2 (SEQ ID NO: 2), BM2SR-3 (SEQ ID NO: 3), BM2SR-4 (SEQ ID NO: 4), or BM2SR-5 (SEQ ID NO: 5) mutation together with other viral components and/or genes expressing other viral components. In some embodiments, the vaccine (e.g., a virus comprising the BM2SR-1 (SEQ ID NO: 1), BM2SR-2 (SEQ ID NO: 2), BM2SR-3 (SEQ ID NO. 3), BM2SR-4 (SEQ ID NO: 4), or BM2SR-5 (SEQ ID NO: 5) mutation) comprises genes from other viral strains, including but not limited to, for example, HA and NA genes from other viral strains. In some embodiments, the vaccine comprises HA and NA genes from, for example, B/Florida/04/2006, B/Brisbane/60/2008, B/Wisconsin/01/2010, or B/Lee/1940 viruses.

A pharmaceutical composition according to the present invention may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-$\alpha$, interferon-$\beta$, interferon-$\gamma$, tumor necrosis factor-$\alpha$, thiosemicarbazones, methisazone, rifampin, ribavirin, a pyrimidine analog, a purine analog, foscamet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition of the invention is administered.

B. Administration

An immunogenic composition (e.g., vaccine) as disclosed herein may be administered via any of the routes conventionally used or recommended for vaccines: parenteral route, mucosal route, and may be in various forms: injectable or sprayable liquid, formulation which has been freeze-dried or dried by atomization or air-dried, etc. Vaccines may be administered by means of a syringe or by means of a needle-free injector for intramuscular, subcutaneous or intradermal injection. Vaccines may also be administered by means of a nebulizer capable of delivering a dry powder or a liquid spray to the mucous membranes, whether they are nasal, pulmonary, vaginal, or rectal.

A vaccine as disclosed herein may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

The present invention thus includes methods for preventing or attenuating a disease or disorder, e.g., infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral, or transdermal routes. Parenteral administration can be by bolus injection or by gradual perfusion over time. In some embodiments, an immunogenic composition as disclosed herein is by intramuscular or subcutaneous application.

In some embodiments, a regimen for preventing, suppressing, or treating an influenza virus related pathology comprises administration of an effective amount of a vaccine composition as described herein, administered as a single treatment, or repeated as enhancing or booster dosages, over a period up to and including between one week and about 24 months, or any range or value therein. In some embodiments, an influenza vaccine as disclosed herein is administered annually.

According to the present invention, an "effective amount" of a vaccine composition is one that is sufficient to achieve a desired biological effect. It is understood that, in some embodiments, the effective dosage will be dependent upon the age, sex, health, and weight of the recipient, kind of concurrent treatment, if any, frequency of treatment, and the nature of the effect wanted. The ranges of effective doses provided below are not intended to be limiting and represent exemplary dose ranges. Thus, in some embodiments, the dosage will be tailored to the individual subject, as is understood and determinable by one of skill in the art. The dosage of an attenuated virus vaccine for a mammalian (e.g., human) adult can be from about $10^1$-$10^{10}$ plaque forming units (PFU)/kg, or any range or value therein. In some embodiments, the dosage of an attenuated virus vaccine for a mammalian (e.g., human) adult can be from about $10^2$-$10^{10}$ plaque forming units (PFU)/kg, or any range or value therein. In some embodiments, the dosage of an attenuated virus vaccine for a mammalian (e.g., human) adult can be from about $10^3$-$10^{10}$ plaque forming units (PFU)/kg, or any range or value therein. In some embodiments, the dosage of an attenuated virus vaccine for a mammalian (e.g., human) adult can be from about $10^4$-$10^{10}$ plaque forming units (PFU)/kg, or any range or value therein. In some embodiments, the dosage of an attenuated virus vaccine for a mammalian (e.g., human) adult can be from about $10^5$-$10^{10}$ plaque forming units (PFU)/kg, or any range or value therein. In some embodiments, the dosage of an attenuated virus vaccine for a mammalian (e.g., human) adult can be from about $10^6$-$10^{10}$ plaque forming units (PFU)/kg, or any range or value therein. In some embodiments, the dosage of an attenuated virus vaccine for a mammalian (e.g., human) adult can be from about $10^7$-$10^{10}$ plaque forming units (PFU)/kg, or any range or value therein. In some embodiments, the dosage of an attenuated virus vaccine for a mammalian (e.g., human) adult can be from about $10^8$-$10^{10}$ plaque forming units (PFU)/kg, or any range or value therein. In some embodiments, the dosage of an attenuated virus vaccine for a mammalian (e.g., human) adult can be from about $10^9$-$10^{10}$ plaque forming units (PFU)/kg, or any range or value therein. In some embodiments, the dosage of an attenuated virus vaccine for a mammalian (e.g., human) adult can be from about $10^9$-$10^{10}$ plaque forming units (PFU)/kg, or any range or value therein. In some embodiments, the dosage of an attenuated virus vaccine for a mammalian (e.g., human) adult can be greater than $10^{10}$ plaque forming units (PFU)/kg. The dose of inactivated vaccine can range from about 0.1 to 200, e.g., 50 μg of hemagglutinin protein. However, the dosage should be a safe and effective amount as determined by conventional methods, using existing vaccines as a starting point.

C. Intracutaneous Delivery

Live flu vaccines are traditionally delivered intranasally to mimic the natural route of infection and promote a similar immune response to that of natural virus infection. As an alternative, disclosed herein are intradermal delivery methods which involve the use of a novel microneedle device to capitalize on the immunological benefits of intradermal delivery. In some embodiments, an attenuated virus (e.g., a BM2 viral mutant) is used in a vaccine composition for intradermal administration. In some embodiments, a BM2 viral mutant, which does not produce infectious progeny virus, is provided in a vaccine. Thus, any potential of reassortment with wild-type circulating influenza viruses is virtually eliminated.

In embodiments disclosed herein, intradermal delivery (intracutaneous) administers vaccine to the skin. In some embodiments, intradermal delivery is performed using a microneedle delivery device. As disclosed herein, intracutaneous delivery has numerous advantages. For example, the immunogenicity of the vaccine is enhanced by triggering the immunological potential of the skin immune system. The vaccine has direct access to the potent antigen-presenting dendritic cells of the skin, i.e., epidermal Langerhans Cells and dermal dendritic cells. Skin cells produce proinflammatory signals which enhance the immune response to antigens introduced through the skin. Further, the skin immune system produces antigen-specific antibody and cellular immune responses. Intradermal delivery allows for vaccine dose sparing, i.e., lower doses of antigen may be effective, in light of the above factors, when delivered intracutaneously.

And, because the vaccine is delivered to the skin through the device's microneedle array, the risk of unintended needle-sticks is reduced, and intracutaneous vaccine delivery via microneedle array is relatively painless compared to intramuscular injections with conventional needle and syringe.

Microneedle devices are known in the art, are known in the art, including, for example, those described in published U.S. patent applications 2012/0109066, 2011/0172645, 2011/0172639, 2011/0172638, 2011/0172637, and 2011/0172609. Microneedle devices may be made, for example, by fabrication from stainless steel sheets (e.g., Trinity Brand Industries, Georgia; SS 304; 50 μm thick) by wet etching. In some embodiments, individual microneedles have a length of between about 500 μm and 1000 μm, e.g., about 750 μm, and a width of between about 100 μm to 500 μm, e.g., about 200 μm. Vaccine can then be applied to the microneedles as a coating. By way of example, but not by way of limitation, a coating solution may include 1% (w/v) carboxymethyl cellulose sodium salt (low viscosity, USP grad; Carbo-Mer, San Diego CA), 0.5% (w/v) Lutrol F-68 NF (BASF, Mt. Olive, NJ) and the antigen (e.g., soluble HA protein at 5 ng/ml; live, attenuated virus such as the BM2 mutant virus described herein, etc.). To reach a higher vaccine concentration, the coating solution may be evaporated for 5 to 10 minutes at room temperature (~23° C.). Coating may be performed by a dip coating process. The amount of vaccine per row of microneedles can be determined by submerging the microneedles into 200 µl of phosphate-buffered saline (PBS) for 5 minutes and assaying for the antigen by methods known in the art.

In some embodiments, a microneedle device is used that is made mainly of polypropylene and stainless steel first-cut pieces that fit together with simple snap fits and heat seals. In some embodiments, the device is completely self-contained and includes the vaccine, a pump mechanism, an activation mechanism, and a microneedle unit. These components are hidden within a plastic cover. With the device, vaccine infusion is initiated by pressing an actuation button. Pressing the button simultaneously inserts the microneedles into the skin and initiates the pumping mechanism that exerts pressure on the primary drug container. When a spring mechanism exerts sufficient pressure on the vaccine reservoir, vaccine begins to flow through the microneedle array, and into the skin. In some embodiments, the delivery of the vaccine dose is completed within about 2 minutes after actuation of the device. After infusion is complete, the device is gently removed from the skin.

In some embodiments, a method for intracutaneous administration of an immunogenic composition (e.g., a vaccine) is provided using a microneedle device. In some embodiments, the microneedle device comprises a puncture mechanism and an immunogenic composition layer comprising a plurality of microneedles capable of puncturing skin and allowing an immunogenic composition to be administered intracutaneously. In some embodiments, the method comprises depressing the puncture mechanism. In some embodiments, the immunogenic composition (e.g. vaccine) comprises a virus comprising a nucleic acid sequence encoding a mutant BM2 protein that is expressed or a mutant BM2 protein that is not expressed; wherein the expressed mutant BM2 protein comprises, or consists of, the amino acid sequence encoded by a nucleotide sequence selected from the group consisting of SEQ ID NO: 1, SEQ ID NO: 2, SEQ ID NO: 3, SEQ ID NO: 4, and SEQ ID NO: 5. In some embodiments, the microneedle array is initially positioned inside of a device housing, and upon actuation of a lever allows the microneedles to extend through the device bottom and insert into the skin thereby allowing infusion of the vaccine fluid into the skin.

The delivery device described herein may be utilized to deliver any substance that may be desired. In one embodiment, the substance to be delivered is a drug, and the delivery device is a drug delivery device configured to deliver the drug to a subject. As used herein the term "drug" is intended to include any substance delivered to a subject for any therapeutic, preventative or medicinal purpose (e.g., vaccines, pharmaceuticals, nutrients, nutraceuticals, etc.). In one such embodiment, the drug delivery device is a vaccine delivery device configured to deliver a dose of vaccine to a subject. In one embodiment, the delivery device is configured to deliver a flu vaccine. The embodiments discussed herein relate primarily to a device configured to deliver a substance transcutaneously. In some embodiments, the device may be configured to deliver a substance directly to an organ other than the skin.

EXAMPLES

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims.

Example 1: Generation of BM2 Viral Mutants

A series of five novel BM2 null mutant constructs (BM2SR-1, BM2SR-2, BM2SR-3, BM2SR-4, and BM2SR-5) based upon the B/Florida/4/2006 segment 7 (FIG. 2) were designed and then synthesized as double-stranded DNA fragments that are suitable for standard in vitro gene-assembly procedures using standard techniques known in the art. The single-stranded mRNA or plus-sense DNA nucleotide sequences of the constructs BM2SR-1 (SEQ ID NO: 1), BM2SR-2 (SEQ ID NO: 2), BM2SR-3 (SEQ ID NO: 3), BM2SR-4 (SEQ ID NO: 4), and BM2SR-5 (SEQ ID NO: 5) are provided in Table 1.

Example 2: Generation and Culturing of BM2 Mutant Virus

This example demonstrates the culturing of BM2SR mutants based upon the B/Florida/04/2006 segment 7 comprising the BM2SR-1 (SEQ ID NO: 1), BM2SR-2 (SEQ ID NO: 2), BM2SR-3 (SEQ ID NO: 3), BM2SR-4 (SEQ ID NO: 4), or BM2SR-5 (SEQ ID NO: 5) mutation and a B/Lee/1940 control, BM2-deleted segment 7. Mutant viruses, such as those carrying mutant BM2 nucleic acid, can be generated by plasmid-based reverse genetics as described by Neumann et al., *Proc. Natl. Acad. Sci. USA* 96:9345-9350 (1999). Briefly, 293T host cells were transfected with one or more plasmids encoding the eight viral RNAs, corresponding to each of the eight influenza B segments. Each viral RNA sequence was flanked by an RNA polymerase I promoter and an RNA polymerase I terminator. Notably, the viral RNA encoding the BM2 protein includes the mutant BM2 nucleic acid sequence. The host cell is additionally transfected with one or more expression plasmids encoding the viral proteins (e.g., polymerases, nucleoproteins, and structural proteins), including a wild-type BM2 protein.

The plasmids were mixed with transfection reagent per standard protocols, incubated at room temperature for 15-30 minutes, and added to $1 \times 10^6$ 293T cells. Forty-eight hours later, viruses in the supernatant were serially diluted and inoculated into BM2CK cells. Two to four days after inoculation, viruses in supernatant of the last dilution well in which cells showing clear cytopathic effect (CPE) were inoculated into BM2CK cells for the production of stock virus. The M genes of generated viruses were sequenced to confirm the gene and the presence of the intended mutations and to ensure that no unwanted mutations were present.

Mutant BM2 viruses were grown and passaged as follows. BM2CK host cells were grown in the presence of MEM supplemented with 10% fetal calf serum. Cells were infected at an MOI of 0.001 by washing with PBS followed by adsorbing virus at 37° C. Virus growth media containing trypsin/TPCK was added and the cells were incubated for 2-3 days until cytopathic effect was observed.

Twelve BM2-deficient, influenza B BM2SR mutant viruses described in Table 4 were constructed. B/FL/4/2006-1, B/FL/4/2006-2, B/FL/4/2006-3, B/FL/4/2006-4, and B/FL/4/2006-5 as shown in Table 4 correspond to BM2SR-1, BM2SR-2, BM2SR-3, BM2SR-4, and BM2SR-5, respectively.

Example 3: BM2SR Virus Protein Expression

This example demonstrates the proteins expressed by the twelve BM2-deficient, influenza B BM2SR viruses described in Table 4.

Vero cells (200,000) were cultured in MEM media with 10% fetal calf serum (FCS) for 24 hours in TC-12 plate wells. After two washes with D-PBS, the Vero cells were infected at high multiplicity-of-infection of 1.0 with the twelve constructed B/Florida/4/2006 BM2SR-1 through BM2SR-5 and B/Lee/40 BM2SR mutant viruses along with two wild-type virus controls B/Lee/1940 and B/Florida/4/2006. After 6 hours of incubation at 35° C. in 5% $CO_2$ atmosphere to allow a single round of replication, samples were harvested for Western analysis.

Infected cells were mildly lysed in 50 mM Tris-HCl pH 8.0, 300 mM NaCl, 1% Triton X-100 with protease inhibitors. Nuclei and insoluble debris were pelleted by centrifugation ay 14,000×G. Clarified supernatant was denatured and reduced prior to sodium dodecyl sulfate polyacrylamide gel electrophoresis (SDS-PAGE) in a 4-12% gradient acrylamide gel in MES buffer (Invitrogen). Resolved proteins were transferred to polyvinylidiene difluoride (PVDF) membrane by semi-dry apparatus for 7 minutes. PVDF was blocked in phosphate buffered saline with 0.1% Tween 20 (PBS-T) containing 3% non-fat dry milk (NFDM).

Proteins were detected in 1% NFDM, PBS-T by antisera specific to two influenza B antigens HA and M1 and for a cell substrate control protein glyceraldehyde 3-phosphate dehydrogenase (GAPDH). Influenza B M1 was detected by a primary antibody cocktail of three 1000:1 diluted monoclonal antibodies (sc-101353, sc-101408, sc-101409; Santa Cruz Biotechnology) and 2000:1 diluted secondary anti-mouse IgG-horse radish peroxidase (HRP) conjugate. The influenza B hemagglutinin protein (HA) was detected by 2000:1 primary polyclonal goat anti-HA serum (NR-3120, BEI) and 2000:1 secondary anti-goat IgG-HRP conjugate. Control GAPDH was detected by primary polyclonal antiserum to GAPDH (NB100-56875, Novusbio) and 2000:1 secondary anti-rabbit IgG-HRP conjugate. Specific bands were detected using the chromogenic HRP substrate 3,3',5,5'-tetramethylbenzidine (TMB).

Figure 4:
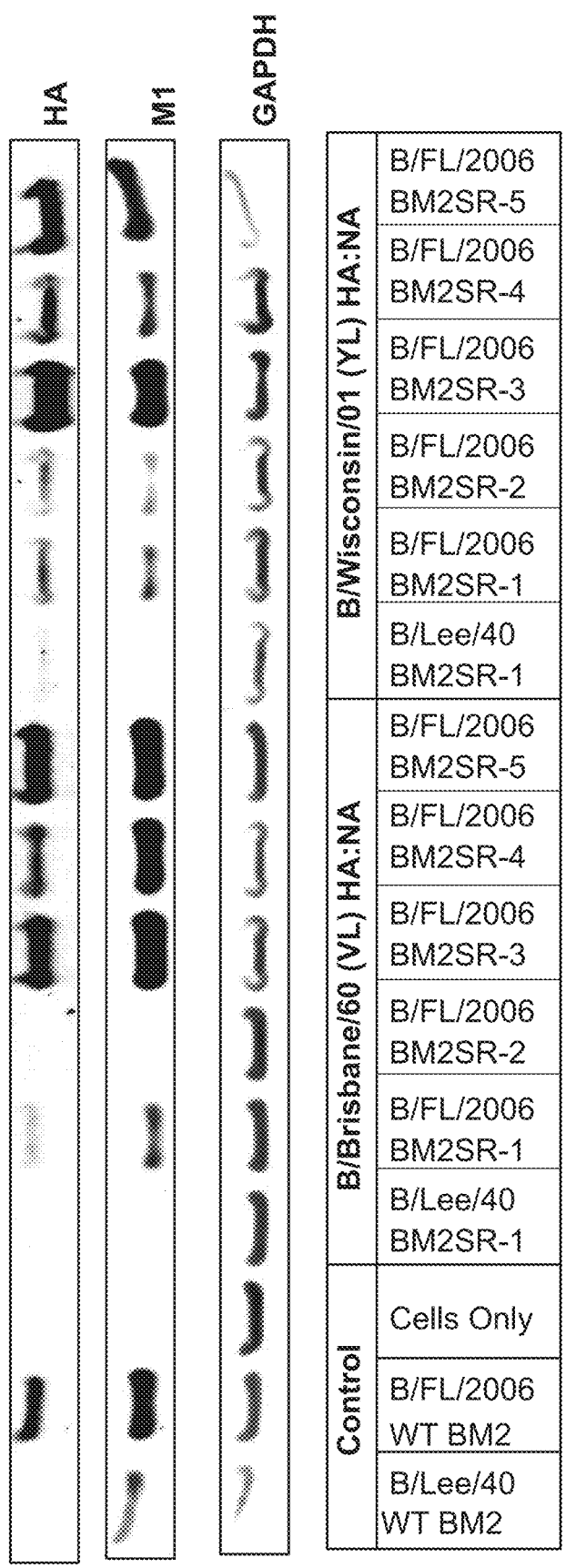
FIG. 4 is a Western blot showing influenza B protein expression. Wild-type (WT) Vero cells were infected with influenza B virus mutants at multiplicity-of-infection (MOI) greater than 1 per cell. B/Lee/1940 and B/Florida/4/2006 were used as wild-type controls. Cytoplasmic protein was extracted 6 hours post-infection and then subjected to SDS-PAGE and transferred to PVDF blots. Blots were sequentially tested by Western analysis with three antisera specific for: 1) influenza B HA protein (top panel); 2) influenza B M1 protein (middle panel); and 3) mammalian GAPDH protein loading control (bottom panel).

Results provided in FIG. 4 indicate that influenza B/Lee/40 M1 and HA expression is less than that of the B/FL/4/2006. Similarly, the B/Lee/40 BM2SR virus expresses low levels or undetectable M1 and HA proteins in both the B/Brisbane/60/2008 and B/WI/01/2010 HA:NA backgrounds. Changing the BM2SR segment from B/Lee/1940 to B/Florida/4/2006 in BM2SR-1 appears to increase the amount of both M1 and HA proteins. No increase was observed from the BM2SR-2 mutation. The BM2SR-3 mutation M1 M86V has a very large effect increasing both M1 and HA expression. The BM2SR-4 mutation also improves expression as compared to B/Lee/40 control. The final combination of the mutations in BM2SR-5 also produces a large improvement in M1 and HA expression as compared to the complete deletion strain. These results also demonstrate that disruption of BM2 expression according to the scheme of FIG. 2 may disrupt BM1 protein expression.

Example 4: BM2SR Virus Replication

This example demonstrates the growth kinetics of the twelve BM2-deficient, influenza B BM2SR viruses described in Table 4.

The viral growth kinetics of the constructed influenza BM2SR viruses were tested in BM2Vero, a Vero-derived cell line that constitutively expresses the B/Lee/40 BM2 protein. BM2Vero cells were cultured in MEM media with 10% fetal calf serum (FCS) for 24 hours in P-060 dishes. Viral infections in triplicate at MOI of 0.001 were performed for twelve viruses with addition of 1 microgram/mL tosyl phenylalanyl chloromethyl ketone-treated trypsin (T-TPCK). Further T-TPCK was added once daily for 3 days (days 1, 2, 3 post-infection) for a total addition of 4 microgram/mL. Infections were incubated at 35° C. 5% $CO_2$. At two-day intervals (days 2, 4, 6, 8 post-infection), the infected-Vero-cell tissue culture supernatant containing secreted influenza B virus was aseptically sampled and the aliquots stored frozen at −80° C. Following completion of the growth curve, the frozen aliquots were titered by standard 50% tissue culture inhibitory dose (TCID50) determination using BM2CK cells (MDCK cells that express BM2 protein). Productive infection from a given dilution was determined using standard World Health Organization hemagglutination assay and analysis (WHO HA assay). The mean and standard deviation of the triplicate $TCID_{50}$ determinations for each virus at each time point was calculated. The results are given in FIGS. 5A and 5B.

Figures 5A, 5B:
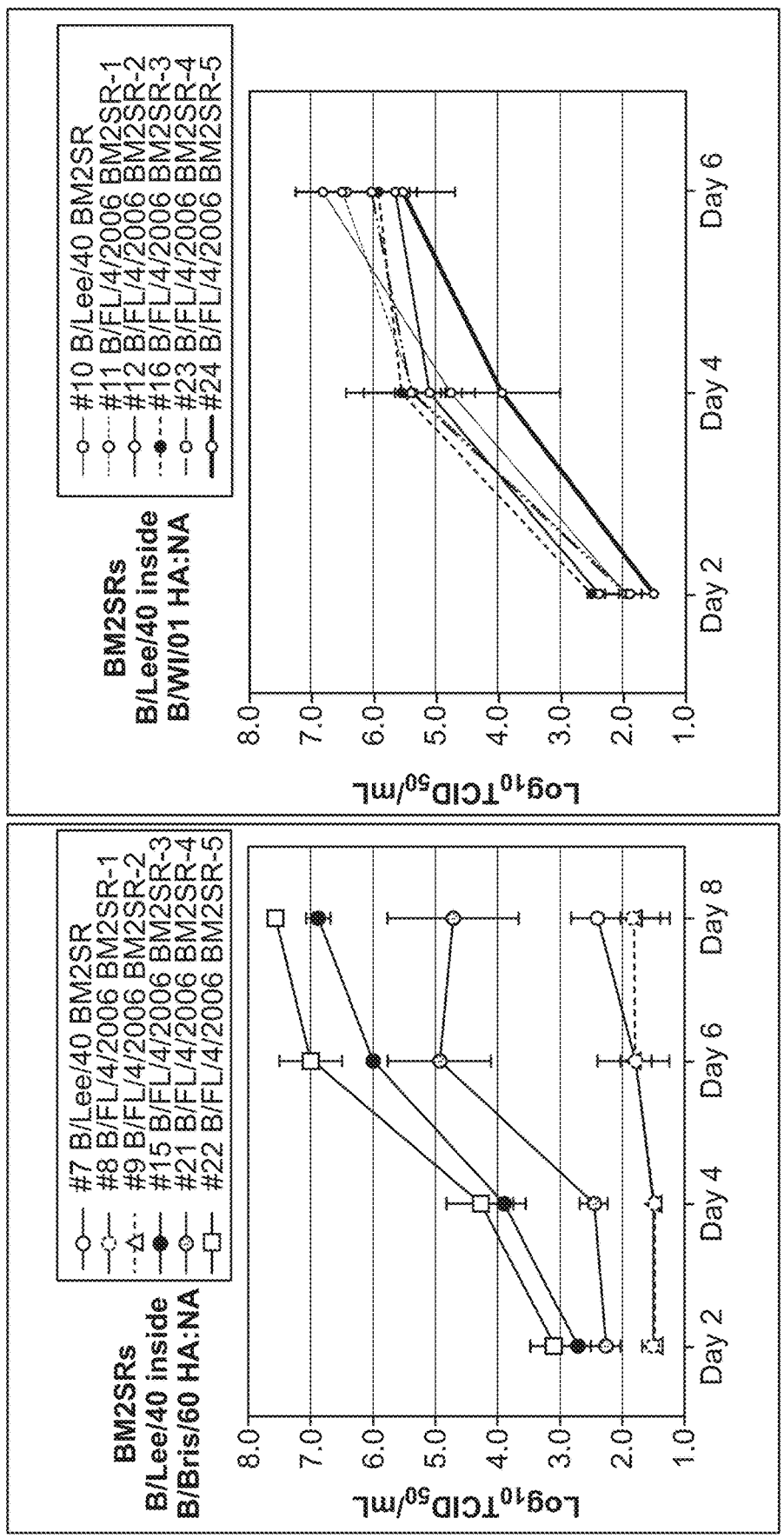
FIGS. 5A and 5B are charts showing the growth curve of BM2SR mutant viruses with B/Brisbane/60 and B/WI/01 HA:NA genes in BM2Vero cells. Cultures of influenza B BM2SR viruses grown in BM2Vero cells (Vero cells expressing BM2 protein) were tested for viral replication by $TCID_{50}$ titration of BM2Vero culture supernatants. Titration was performed in BM2CK cells (Madin-Darby Canine Kidney (MDCK) cells expressing BM2). Six BM2SR mutant viruses expressing the HA and NA from B/Brisbane/60/2008 (B/Bris/60): #7, #8, #9, #15, #21, and #33; and six BM2SR viruses expressing the HA and NA of B/Wisconsin/01/2010 (B/WI/01): #10, #11, #12, #16, #23, and #24 were tested. Relative to mutant viruses #21, #22, #23, and #24, mutant viruses #7, #8, #9, #11, and #12 contain larger deletions (i.e., shorter mRNA sequences) and exhibit slower growth.

The growth curve for the six viruses expressing HA and NA from B/Brisbane/60/2008 given in FIG. 5A indicate that the nearly-full-length mutant BM2SR-4 and especially the M1 M86V mutants BM2SR-3 and BM2SR-5, directed the faster viral growth and reached higher final titer. The M1 M86V mutation appeared to improve viral growth in the BM2Vero4 cell substrate when combined with the BM2SR-2 mutation in mutant BM2SR-3, and with the BM2SR-4 mutation in the BM2SR-5 mutant. The best mutant strain, BM2SR-5, reached final titer of 7.50 log 10±0.1 log 10 $TCID_{50}$ equivalents/mL in the BM2Vero cell substrate. The B/FL/04 2006 BM2SR-3, -4, -5 mutations confer from a 2 log 10 up to a more than 5 log 10 improvement in yield as compared to the B/Lee/1940 BM2SR strain $TCID_{50}$ value of 2.42 log 10±0.39 log 10 $TCID_{50}$ equivalents per mL when combined with the B/Brisbane/60 HA and NA.

Growth of influenza B strains with HA and NA from B/Wisconsin/01/2010 was more uniform (FIG. 5B). A subtle improvement of about 10^0.5 $TCID_{50}$/mL could be noted for the BM2SR-2, BM2SR-3 and BM2SR-4 mutants at day 4 of the growth curve. By Day 6, the difference was lost and the final titers were statistically similar. Thus, in the context of the viruses containing HA and NA from B/Wisconsin/01/2010, the engineered BM2SR constructs, especially BM2SR-4 and BM2SR-5, could only slightly improve virus growth kinetics but had less effect on final viral yield. Performance of a given virus is dependent on the HA and NA constellation of the given strain.

Example 5: Stability of BM2SR Variants

Figure 6A:
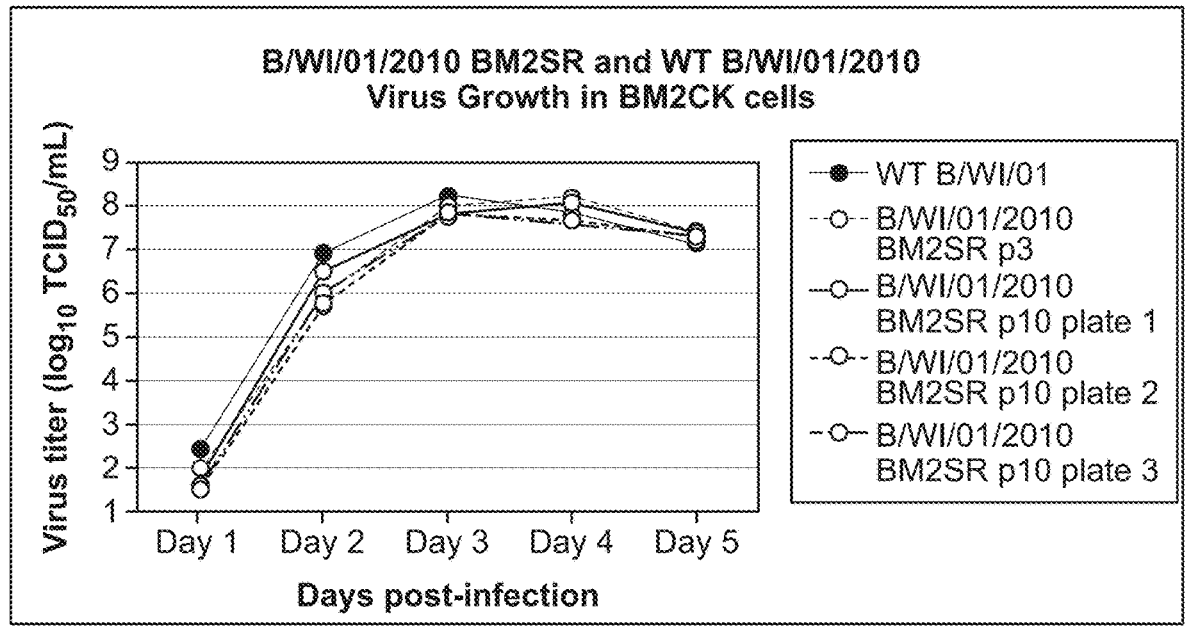
FIGS. 6A and 6B are charts showing the stability of BM2SR-WI01 (i.e., BM2SR expressing HA and NA of B/Wisconsin/01/2010) in BM2CK and MDCK cells.
Figure 6B:
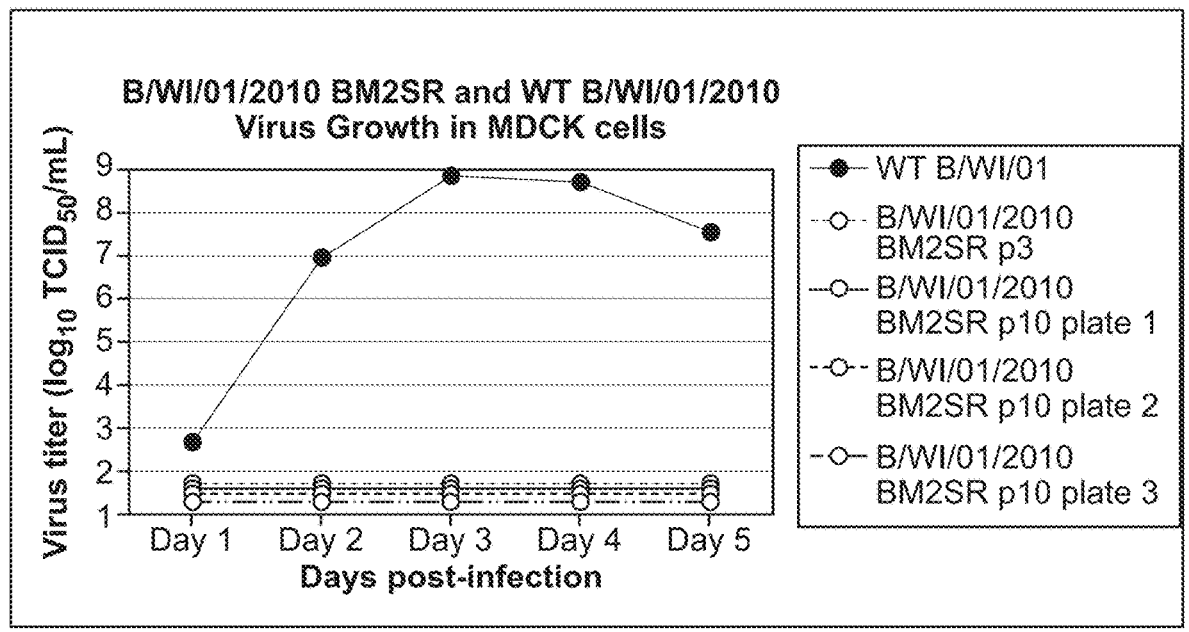

To test the stability of the BM2 gene of BM2SR variants in wild-type cells, the BM2SR variants were passaged in wild-type MDCK cells, which lack BM2 protein expression, along with BM2CK cells, which are BM2-protein-expressing MDCK cells. All BM2SR variants and wild-type influenza B viruses (WT B/WI01) were passageable in BM2CK cells without any mutations until at least passage 10 (FIG. 6A). However, BM2SR variants were not able to be passaged in wild-type MDCK cells (FIG. 6B).

Example 6: BM2 Mutant Viruses are Attenuated In Vivo

An experiment was performed to demonstrate that BM2SR mutant viruses are attenuated in vivo. Six-week-old BALB/c, female mice were inoculated intranasally with one of the following mutants: BM2SR Bris60 and BM2SR Wisc01 (both of which contain the mutant M segment from B/Lee/40 as set forth in SEQ ID NO: 6 (BM2SR-0)). The mutants were administered at a dose of $1.2\times10^6$ TCID$_{50}$ per mouse. A control group of mice was given PBS. The mice were observed for 14 days after inoculation for any change in body weight and symptoms of infection.

Figure 7:
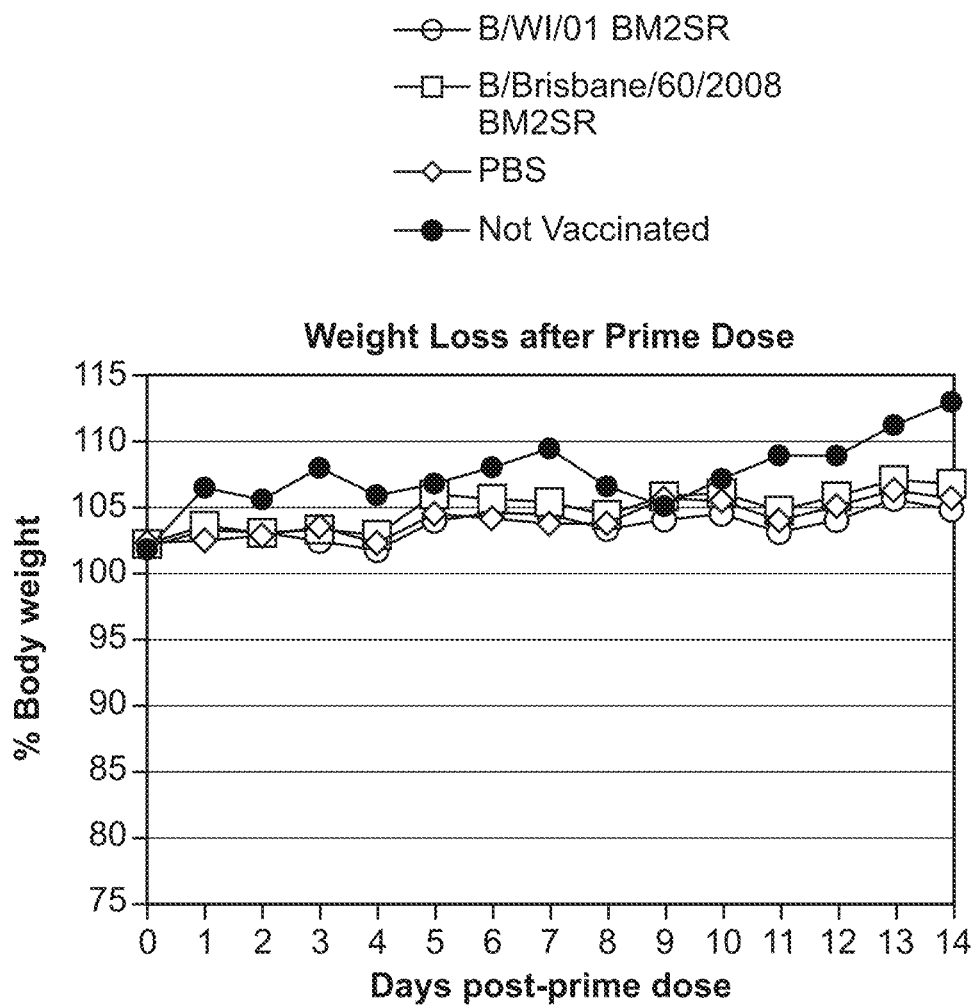
FIG. 7 is a chart showing the change in mouse body weight after inoculation with BM2SR-0 variants (BM2SR-Bris60 and BM2SR-WI01 having a mutant BM2 gene comprising SEQ ID NO: 6).

As shown in FIG. 7, mice inoculated with the BM2SR viruses and PBS did not show any clinical symptoms of infection nor lose any body weight over the 14-day period. The change in body weight between the groups was comparable over the 14-day period. Taken together, the lack of clinical symptoms and lack of loss of body weight indicate that the BM2SR mutant viruses are attenuated and not pathogenic in mice.

Figure 8A:
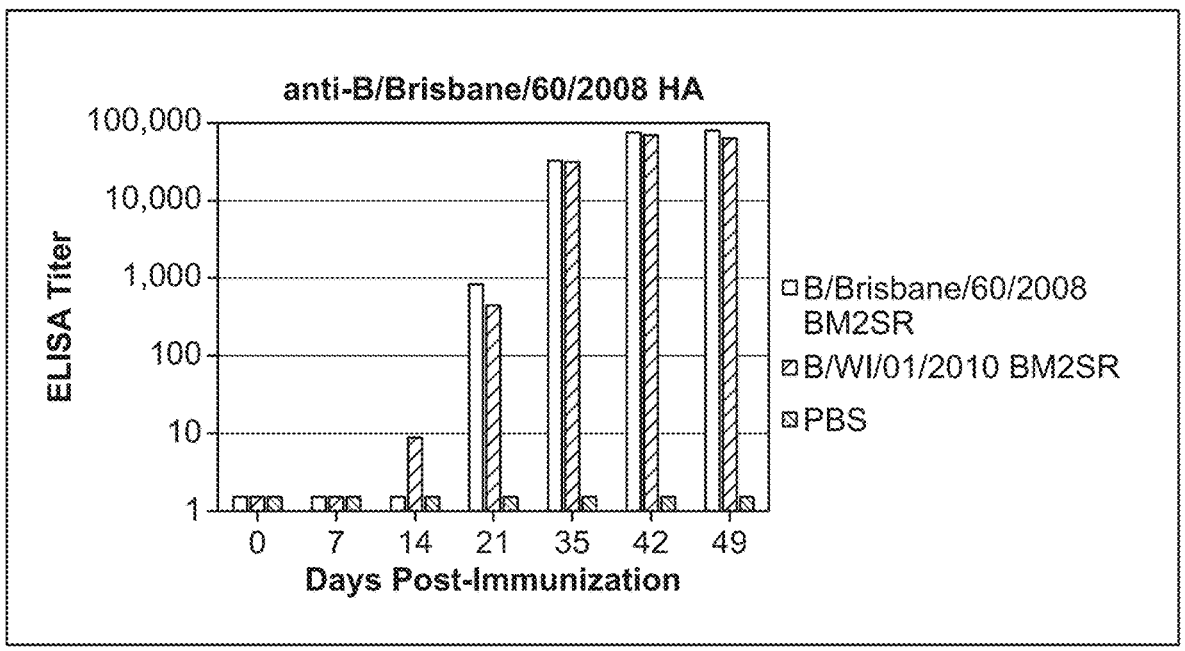
FIGS. 8A and 8B are charts showing anti-HA IgG antibody responses in mice inoculated with BM2SR-0 variants (BM2SR-Bris60 and BM2SR-WI01) having a mutant BM2 gene comprising SEQ ID NO: 6. Serum samples were collected on days 7, 14, and 21 after prime inoculation and on days 35, 42, and 49 after the second immunization on day 28.
Figure 8B:
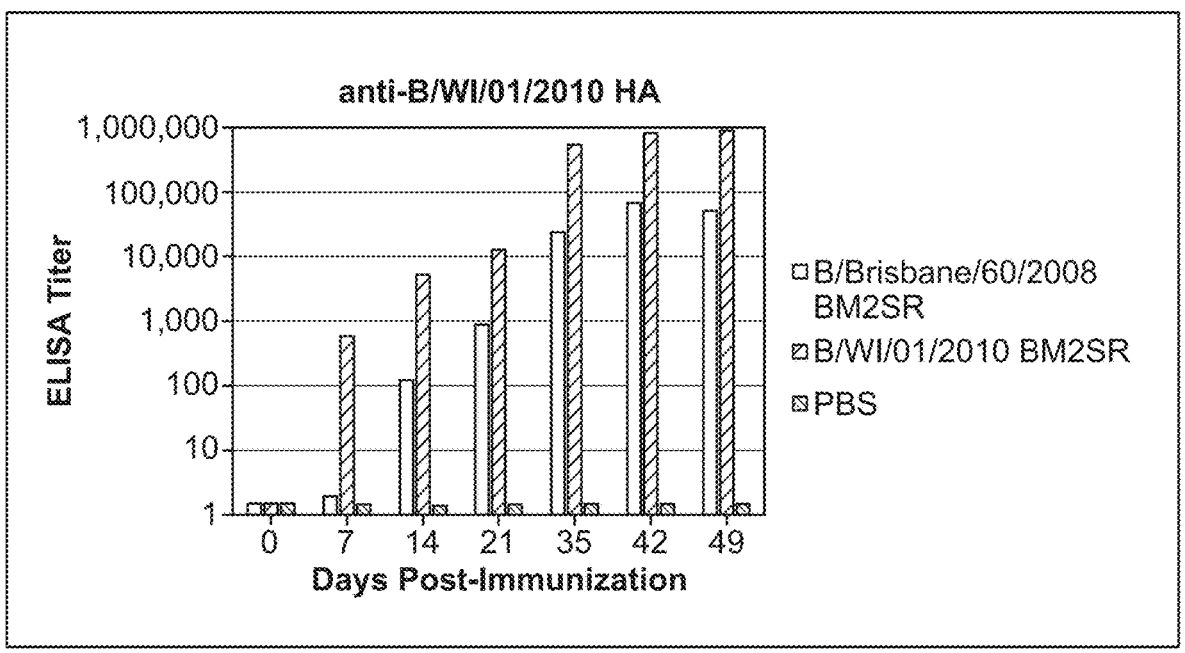
Figure 10:
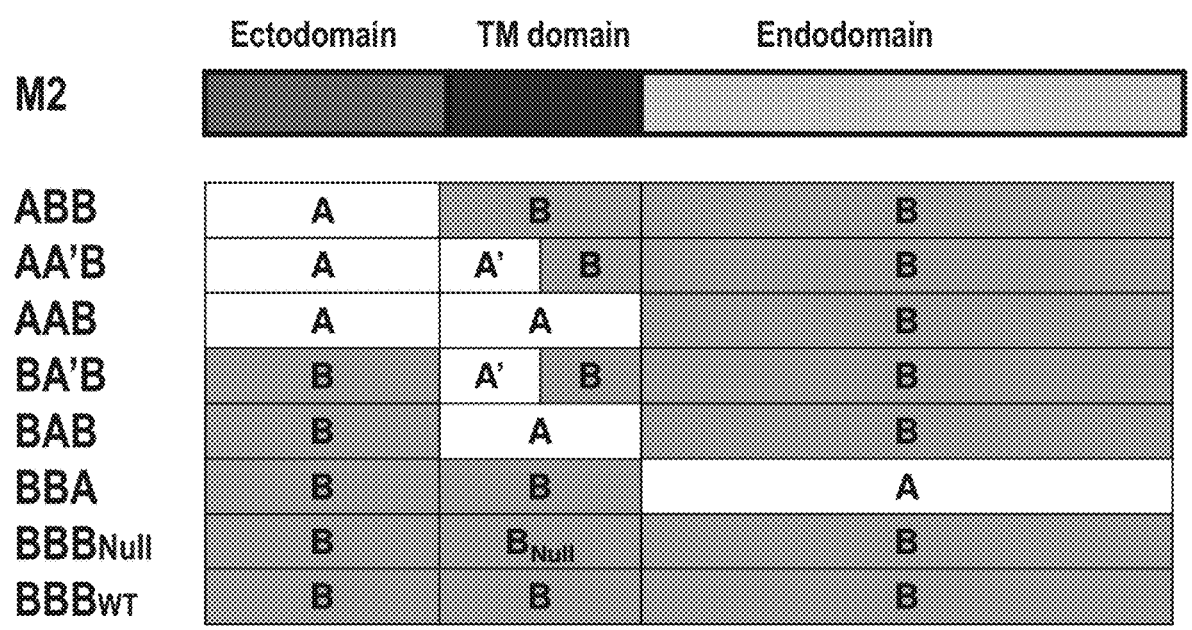
FIG. 10 is a schematic diagram showing influenza A M2 and influenza B M2 (BM2) chimeric fusion constructs.

Example 7: BM2 Mutants Induce Antibodies Against Influenza B Virus Challenge Testing was performed to determine antibody titers against two influenza B lineages, Yamagata and Victoria, in serum samples from the mice described above. Serum samples were taken on days 7, 14, and 21 after prime inoculation and on days 35, 42 and 49 after the second immunization on day 28. Anti-HA IgG antibody titers from the serum samples were determined by enzyme-linked immunosorbent assay (ELISA) against B/Wisconsin/01/2010 and B/Brisbane/60/2008. The humoral response is shown in FIGS. 8A-8B, which show that both BM2SR mutants, which comprise the M segment from B/Lee/40 with a deletion of M2 (SEQ ID NO. 6, BM2SR-0), elevated anti-influenza virus antibodies higher than the control PBS group against both antigens. Mice boosted by BM2SR mutant viruses had higher level of anti-influenza HA antibodies after the second immunization than the level after the prime dose.

Example 8: Growth of M2-Deficient Influenza a and BM2-Deficient Influenza B Strains in BM2-Expressing Cell Substrate An experiment was performed to test the ability of influenza A M2 and influenza B BM2 to complement M2-deficient influenza A (A/CA/07 M2SR and A/Brisbane/10 M2SR, both of which comprise the M2 mutant as set forth in SEQ ID NO: 33) and B (B/WI/01 BM2SR-0 and B/Brisbane/60 BM2SR-0) viruses using a standard 50% tissue culture infectious dose (TCID$_{50}$) assay (WHO). Confluent monolayers of M2CK and BM2CK cells prepared in 96-well tissue culture plates were infected in quadruplicate with 0.2 mL from a 10-fold dilution series of four influenza viruses: 2 dilutions prepared from the influenza A M2SR and 2 from the influenza B BM2SR virus strains. After 4 days of incubation at 35° C., 5% CO$_2$ atmosphere, the cytopathic effect and an erythrocyte hemagglutination assay (HA) (WHO) were used at end-point to test the culture supernatant for influenza replication. The highest dilution factors where influenza replication was observed from each of the replicate infections were then used to determine the log$_{10}$ TCID$_{50}$ values for each infection of two cell lines with four viruses shown in FIG. 9.

Surprisingly, the BM2CK cell substrate was able to complement both influenza A M2-deficient M2SR virus strains equally as well as the serotype-matched M2CK cells (FIG. 9). M2SR viruses containing surface antigens derived from both of the common HA NA subtypes of human influenza, H1N1 and H3N2, were both able to replicate to equivalent log$_{10}$ TCID$_{50}$ values of about 7.0. Conversely the influenza A M2 protein in M2CK cells only poorly supported the replication of BM2-deficient influenza B BM2SR strains tested, yielding a TCID$_{50}$ titer about 3 log$_{10}$ less than that provided by the type matched BM2CK cells. This indicates that the influenza B M2 protein can substitute for the influenza A protein and can support the replication of influenza A viruses from two subtypes. In contrast, the influenza A M2 protein does not appear capable of replacing the BM2 protein for influenza B replication.

Example 9: Chimeric M2 Proteins

Figure 11:
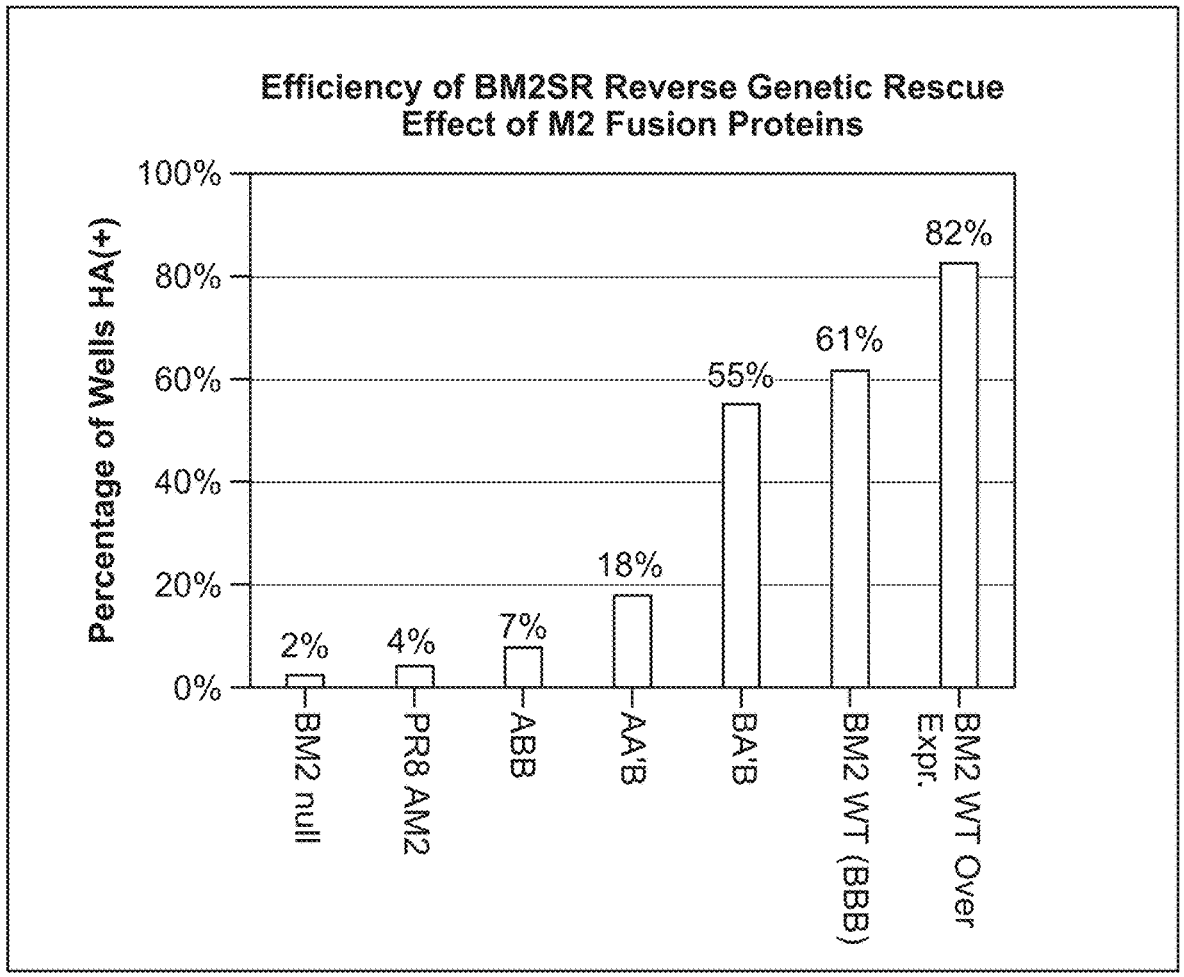
FIG. 11 is a chart showing the capability of M2 and BM2 chimeras to support rescue of a BM2-deficient influenza B (BM2SR) virus. A BM2-deficient virus was generated by standard influenza rescue techniques using plasmids to transiently supply chimeric forms of M2 in 293T cells. The percentage of BM2CK TC96 wells productively infected by 293T influenza B BM2SR RG supernatant was determined by WHO HA assay.

To test the function of chimeric M2 proteins, fusion constructs were inserted by typical gene assembly procedures into standard plasmids containing the CMV IE promoter and the bovine growth hormone poly-adenylation transcriptional control sequences for high-level expression in mammalian cells in culture. Wild-type M2 and BM2 cDNA expression plasmids were also constructed. In addition, the wild-type BM2 cDNA sequence was inserted into the pCAGGS promoter terminator plasmid for the highest possible level expression—even greater than CMV. The plasmids were used to supply M2 function in reverse genetics (RG) of influenza B BM2SR virus. The efficiency of the RG was estimated by inoculating 1% of the 293T-RG-produced virus onto 96 independent wells of recipient BM2CK cells for recovery of the BM2-deficient progeny. After 4 days incubation at 35° C., 5% CO$_2$, the BM2CK culture supernatant was tested for virus replication by standard hemagglutination assay (WHO HA). The percentage of wells that became WHO HA-positive are plotted in FIG. 11.

The BM2 null mutation did not support RG, confirming the requirement for M2 proton channel activity in the replication of influenza. The wild-type influenza A M2 also did not support replication. The chimeric M2 proteins, ABB and AA'B, which contain the influenza A M2 ectodomain (M2e), do not support RG nearly as well as the wild-type BM2 or the BA'B mutant that lacks M2e, suggesting the influenza A ectodomain domain is inhibitory. Combined data indicate that the influenza B endodomain is required for the replication of influenza B, while the influenza A transmembrane (TM) domain can substitute for the TM of BM2. Increased expression from the pCAGGS vector as compared to the standard CMV promoter improved the performance of the wild-type BM2 cDNA, indicating that total expression level of BM2 can also be limiting to RG.

Example 10: Capacity of Wild-Type and Chimeric M2 Proteins to Express BM2 Protein M2 proteins were tested for the capacity to support M2-deficient and BM2-deficient virus growth when expressed from the cell-substrate genome. Vero cells were chemically transfected with plasmids encoding M2 and chimeric mutants as well as the neomycin phosphotransferase (neo) gene that confers resistance to the aminoglycoside inhibitor of protein synthesis, G418.

After two days in culture, the transfected cells were dissociated and re-plated in medium containing G418. Cells were cultured under G418 selection for several weeks in order to select for clones that have randomly integrated the plasmid DNA into the cell line genome. Some fraction of the G418-resistant clones will also contain a functional, integrated copy of the M2 chimeric mutant transgene. These functional clones can then be tested for capacity to support virus selection. Replication can be tested either from G418-resistant clone pools selected in bulk or from individual clones that are selected and isolated using standard limit of dilution cloning (LDC) procedures. Analysis of clone pools provides measurement on the performance of a construct within a few weeks of growth, while LDC takes much longer. However, it is important that several rounds of LDC are required for isolation of cell substrates suitable for regulated production of vaccine for use in human.

After multiple rounds of selection and LDC using both the wild-type and the mutant cDNA plasmids, suitable clones that express high levels of BM2 were not isolated (data not shown). Western analysis showed rapidly decreasing amounts of detected BM2 after each passage of cells in culture. Early passage clone pool M2SR and BM2SR virus replication data suggested that the constructs were functional, but stable expression of the constructs from cell genome was not established in Vero cells. Analysis of the influenza encoded gene sequences indicated that they were 60% A-T and that viral codon usage bias differed significantly from that of the host Vero. Furthermore, multiple sequence motifs that can silence or repress transcription were identified within the native viral gene coding regions. This phenomenon is common when genes from one organism are transferred into another, but may be underappreciated for influenza virus. Although the virus must replicate in human cells, influenza does not employ the same codon usage pattern as the host.

Figure 12:
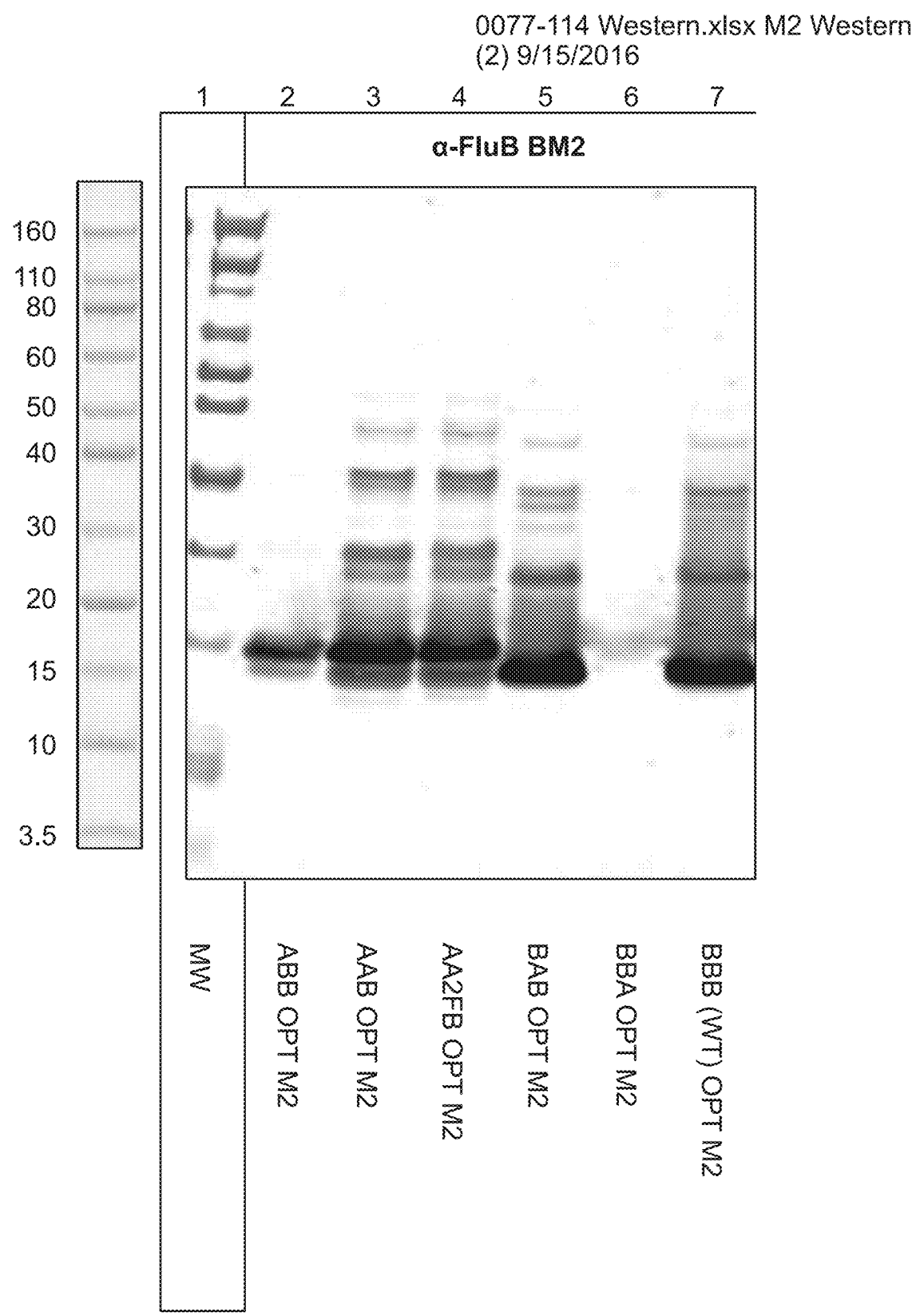
FIG. 12 shows a Western blot analysis of codon-optimized wild-type BM2 and chimeric M2 proteins. All M2 proteins exhibit altered mobility in the SDS-PAGE system used appearing approximately 5,000 Dalton larger than the calculated molecular weights (MW). Mutants ABB, AAB, AA2FB contain the larger influenza A ectodomain and so migrate in the SDS-PAGE at a correspondingly larger apparent MW.

To increase expression of the wild-type M2, BM2, and of the chimeric mutants; codon-optimization of the coding sequences was performed to remove negative regulatory motifs, make the cDNA about 50% A-T, and to alter the genes from influenza to Vero cell codon bias. These constructs were tested by chemically-mediated transfection of Vero cells. Two days post transfection, the transient expression of proteins was evaluated. Total cell protein extracts were analyzed by immunoblot using polyclonal antisera specific to BM2. The data in FIG. 12 show much higher protein expression from the designed transgenes than had previously been obtained in a transient assay from native sequences (native not shown). Of note, the BBA mutant could not be detected as the anti-BM2 antisera was directed against the BM2 endodomain.

Figure 13:
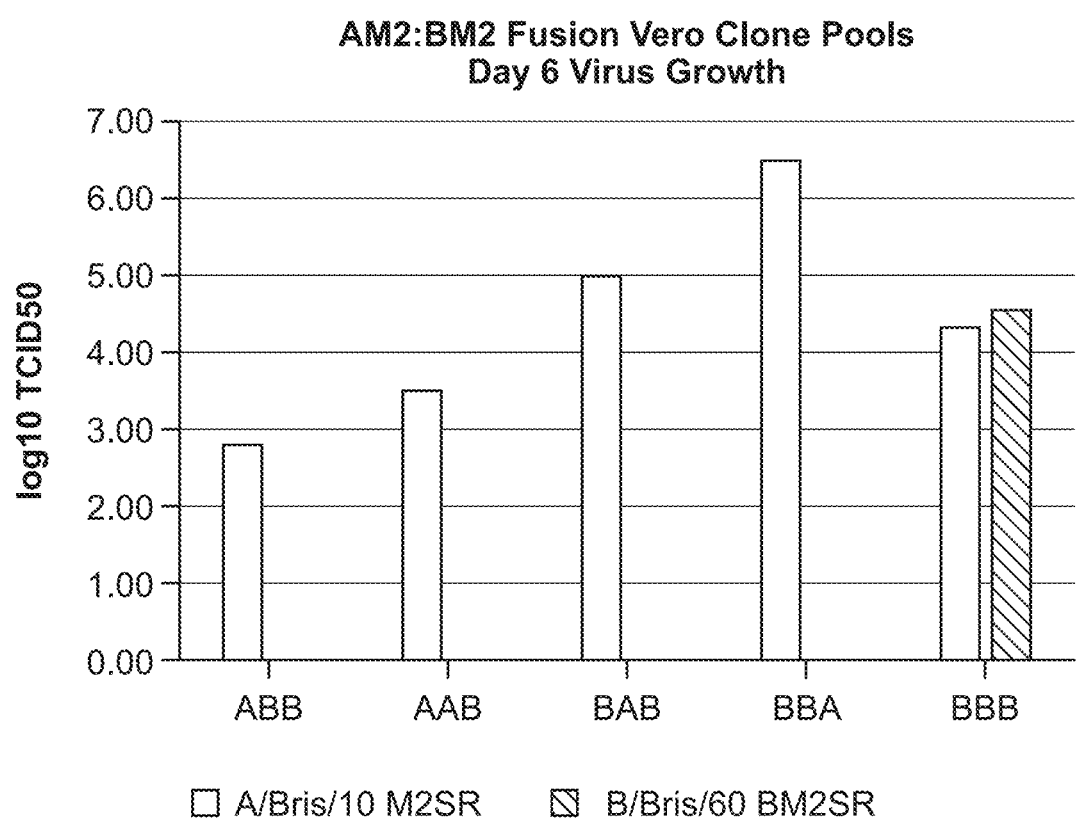
FIG. 13 is a chart showing the viral titer of M2-deficient influenza A CA/07/H1N1pdm M2SR in Vero cell substrates expressing influenza A M2:influenza B M2 (AM2:BM2) chimeric proteins six days post infection with influenza A/Brisbane/10 M2SR and with influenza B/Brisbane/60 M2SR M2-deficient viruses.

Example 11: Testing the Capacity of Chimeric, Codon-Optimized M2 Proteins to Support M2—Deficient and BM2-Deficient Virus Growth Codon optimized, chimeric M2 proteins were tested for the capacity to support M2-deficient and BM2-deficient virus growth. Vero cells were chemically transfected with plasmids encoding codon-optimized M2 chimeric mutants as well as the neomycin phosphotransferase (neo) gene that confers resistance to the aminoglycoside inhibitor of protein synthesis, G418. After two days in culture, the transfected cells were dissociated and re-plated in medium containing G418. Cells were cultured under G418 for 2 weeks to select for clones that have randomly integrated the plasmid DNA into the cell line genome. Some fraction of the G418 resistant clones will also contain a functional, integrated copy of the M2 chimeric mutant transgene. Clone pools transfected with BM2 and chimeras and selected in bulk were infected with influenza A/Brisbane/10 M2SR (comprising the M2 mutant as set forth in SEQ ID NO: 33) and with influenza B/Brisbane/60 BM2SR-0 (comprising the BM2 mutant as set forth in SEQ ID NO: 6) M2-deficient viruses at MOI 0.01. Six days after infection, viral titer in culture supernatant was measured using standard $TCID_{50}$ procedures and the data is presented in FIG. 13.

All of the M2 clone pools tested supported the growth influenza A M2SR in Vero cells. Only the wild-type BM2 (BBB) clone pool supported the growth of influenza B BM2SR. Thus all three BM2 domains appear to be specific for influenza B BM2SR replication in Vero cells. The clone pool expressing the BBA mutant that lacks the influenza A M2e and transmembrane (TM) domain, but contains the M2 endodomain was found to be best at supporting influenza A M2SR growth. The BM2 endodomain was not as effective, suggesting that the M2 endodomain has evolved to be somewhat influenza A-specific. The ABB and the AAB chimeric mutants exhibited worse performance than the BAB and BBA constructs showing that the influenza A ectodomain may be inhibitory to virus growth, even for influenza A itself. The inhibitory regions including, but not limited to, M2e may be removed and modified domains that increase replication and titer can be added.

Thus, performance of cell substrates for production of M2-deficient influenza A M2SR virus and for BM2-deficient BM2SR vaccine viruses can be improved by use and expression of engineered M2 proteins including chimeric fusions of M2 genes from totally different serotypes influenza A and influenza B.

Example 12: Growth of M2-Deficient Influenza A/California/07/H1N1pdm M2SR in BM2-Expressing Vero Cell Substrate A/California/07/2009pdm H1N1 M2SR (A/CA/07) is an M2-deficient influenza A virus containing the H1 and N1 segments of A/California/07/2009pdm, and comprising the M2 mutant as set forth in SEQ ID NO: 33. This vaccine candidate virus that is replication-incompetent in normal cells was used to infect 2 cell lines that constitutively express 2 types of M2 proteins. The first M2 cell substrate was the MDCK lineage standard cell line M2CK, which expresses A/PR8 M2 protein (encoded by the nucleotide sequence set forth in SEQ ID NO: 23). MDCK cells are typically employed for influenza research and development because they are known to support rapid replication of influenza virus to high titer in culture. Unfortunately, it is difficult to achieve regulatory approval for any biologic products derived from MDCK because the MDCK cells themselves have been shown to be carcinogenic. The second cell line, BM2Vero4, contains codon-optimized wild-type influenza B/Lee/40 BM2 protein (encoded by the nucleotide sequence set forth in SEQ ID NO: 27), but it was derived from Vero, an African green monkey kidney cell line. Vero cell substrates have been utilized for approved cell-based vaccine manufacture since the 1960's (polio & MMR vaccines).

Figure 14:
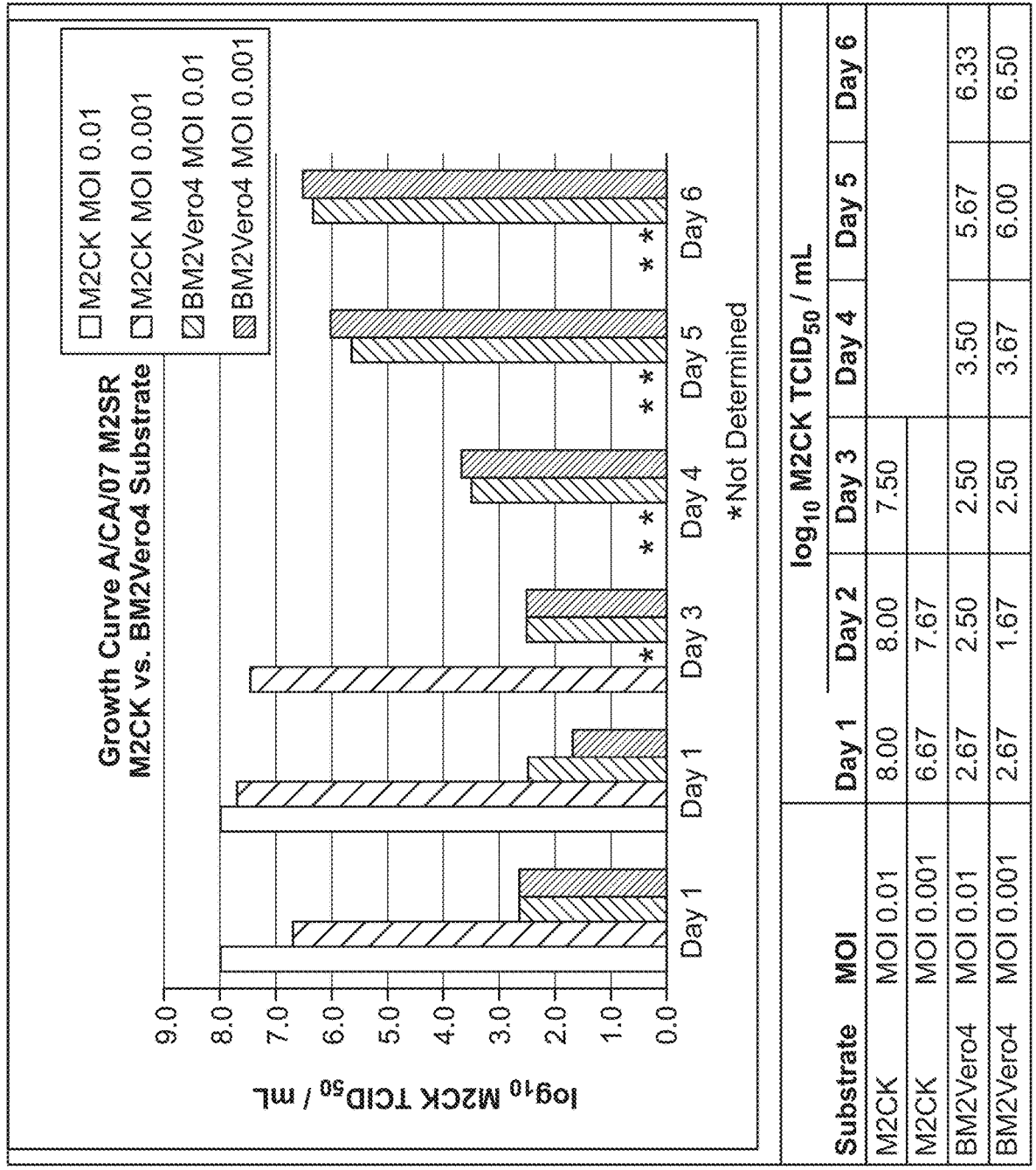
FIG. 14 is a chart showing the growth of M2-deficient influenza A CA/07/H1N1pdm M2SR in M2-expressing M2CK and BM2-expressing Vero cell substrates.

The virus infection was performed in Minimal Essential Media (MEM) supplemented with 0.3% BSA and 1.0 micro g/mL Trypsin-TTPK at two multiplicity of infection (MOI) levels, 0.01 and 0.001. Aliquots were withdrawn daily from Day 2 through Day 6 post-inoculation. The concentration of viable influenza A virus contained in the cell culture supernatant samples was assayed using the standard $TCID_{50}$ Assay, incubated for 4 days at 35° C., 5% $CO_2$ with the influenza A M2SR-permissive M2CK cells and BM2Vero4 cells. Results are presented in FIG. 14.

As expected, influenza A/CA/07/2009pdm M2SR replicated well in M2CK cells, quickly reaching peak titer at the Day 2-time point. The titer in the Vero lineage took 5-6 days to reach peak. The A/CA/07 grew to titers of $\log_{10}$ 5.67 and 6.00 in BM2Vero cells as compared to the viral titers of $\log_{10}$ 7.00 and 6.33 obtained with the M2CK cells. This was seen despite BM2Vero4 being derived from the Vero cell line that is much less-permissive for influenza replication as compared to MDCK cells.

Thus, expression of codon-optimized influenza B/Lee/40 *BM*2 protein (encoded by the nucleotide sequence set forth in SEQ ID NO: 27) in Vero cells achieves influenza A H1N1 M2SR virus production at levels nearly equivalent to that of the R&D quality MDCK cell substrate that expresses the influenza A form of the M2 protein.

Example 13A: Influenza BM2 Protein can Provide the Ion Channel Activity Necessary for Virus Un-Coatins to a Chimeric Influenza a M2SR Virus Although M2SR does not express M2 protein and therefore cannot produce progeny virions, M2SR does undergo de novo protein synthesis and produces viral antigens in normal cells. This example demonstrates that influenza BM2 protein can provide the ion channel activity necessary for virus un-coating to a chimeric influenza A M2SR virus (i.e., an influenza A M2SR virus produced in a complementing BM2 cell line resulting in BM2 proteins incorporated in the viral membrane).

To demonstrate this, influenza A M2SR Hong Kong/4801/2014 (H3N2) virus was passaged 3 times in influenza A M2-expressing M2VeroA cells and chimeric M2SR Hong Kong/4801/2014 (H3N2) was passaged 3 times in influenza B BM2-expressing BM2Vero cells. Then human A549, canine MDCK or African green monkey Vero cells were inoculated with M2SR or with chimeric M2SR virus at an MOI of 4 and cultured in medium without trypsin to ensure that viruses completed only one life cycle.

Figure 15A:
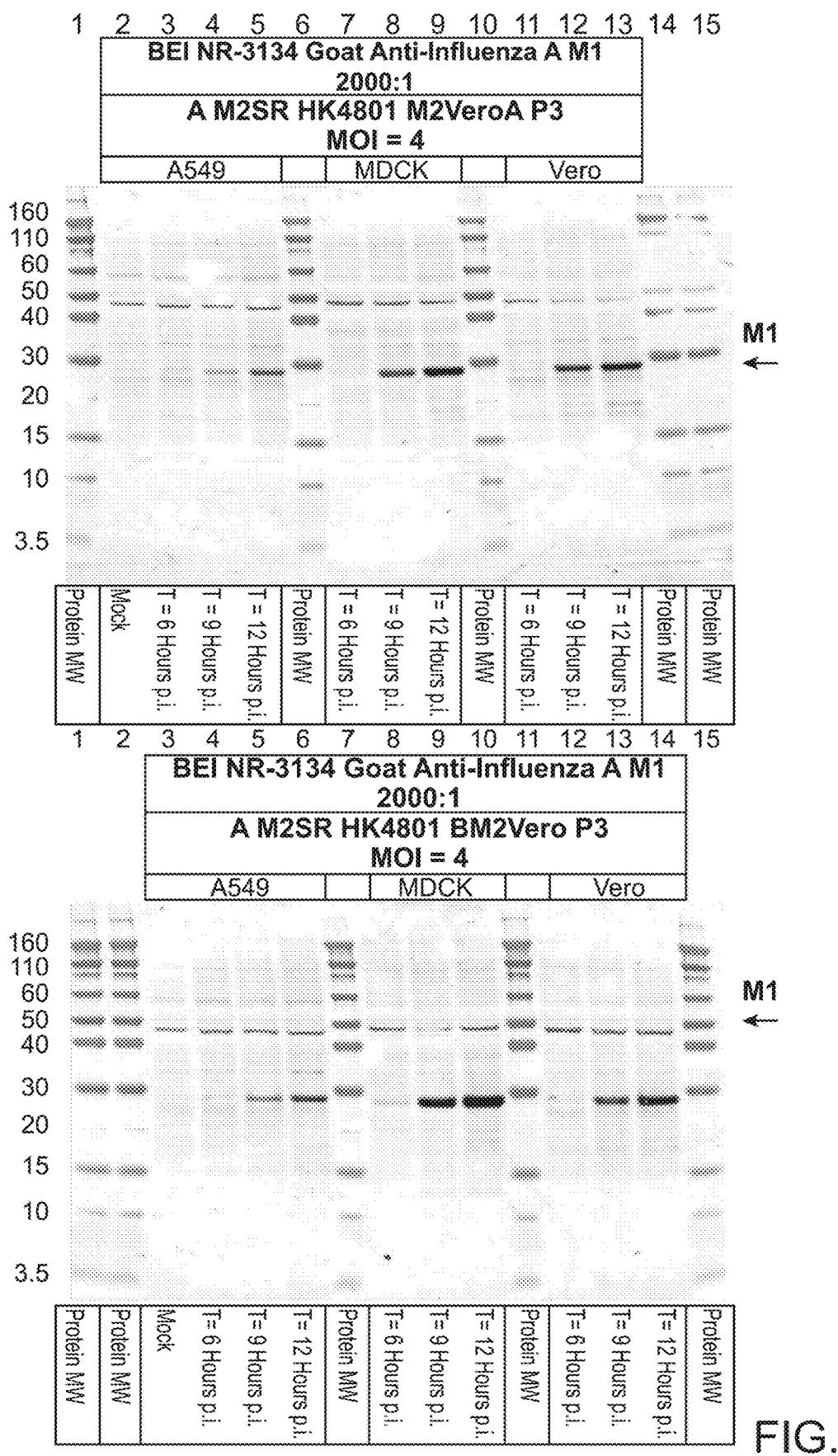
FIG. 15A is an influenza A matrix M1 immunoblot.

A crude cytoplasmic extract of cells was performed at timepoints 6, 9, and 12 hours post-infection (p.i.). Cells were lysed in 50 mM Tris HCl, pH=8.0, 150 mM NaCl, 1% Triton X-100, followed by centrifugation at 15,000×G. Soluble proteins in the supernatant were combined with LDS sample buffer (Thermo Fisher Scientific, Waltham, MA) and 5 mM TCEP and denatured by heating to 70° C. for 10 minutes. Proteins were separated on a 4-12% denaturing Bis-Tris NuPAGE polyacrylamide gel (Thermo Fisher Scientific, Waltham, MA) in MES buffer and transferred to PVDF membranes. Pre-stained protein molecular weight standards were run for size comparison. Membranes are blocked in 1% (w/v) non-fat dry milk and incubated with primary anti-influenza virus matrix protein polyclonal goat antiserum NR-3134 (BEI Resources, NIAID, NIH) at a 2000:1 dilution, followed by secondary horseradish peroxidase-conjugated anti-goat IgG (H+L) (SeraCare KPL, Milford, MA) at a 3000:1 dilution. Bands were visualized using TMB membrane peroxidase substrate (SeraCare KPL, Milford, MA). Polyclonal anti-serum against M1 matrix protein detects very similar expression of the 28 kDal molecular weight protein for the M2SR, and the chimeric M2SR viruses, with nearly identical induction kinetics of about 9 hours in all three cell lines tested (FIG. 15A).

Example 13B: Only Influenza B BM2 Protein and No Influenza a M2 Protein can be Detected in a Chimeric Influenza a M2SR Virus Produced in a Complementing BM2 Cell Line M2SR cannot produce progeny virions unless the virus is propagated in a supportive cell line that expresses the influenza A M2 protein or the influenza B BM2 protein since M2SR cannot express M2 protein. This example demonstrates that a chimeric influenza A M2SR virus produced in a complementing BM2 cell line results in only BM2 proteins incorporated in the viral membrane. M2SR virus grown in a complementing M2 cell line contains only M2 protein.

Figure 15B:
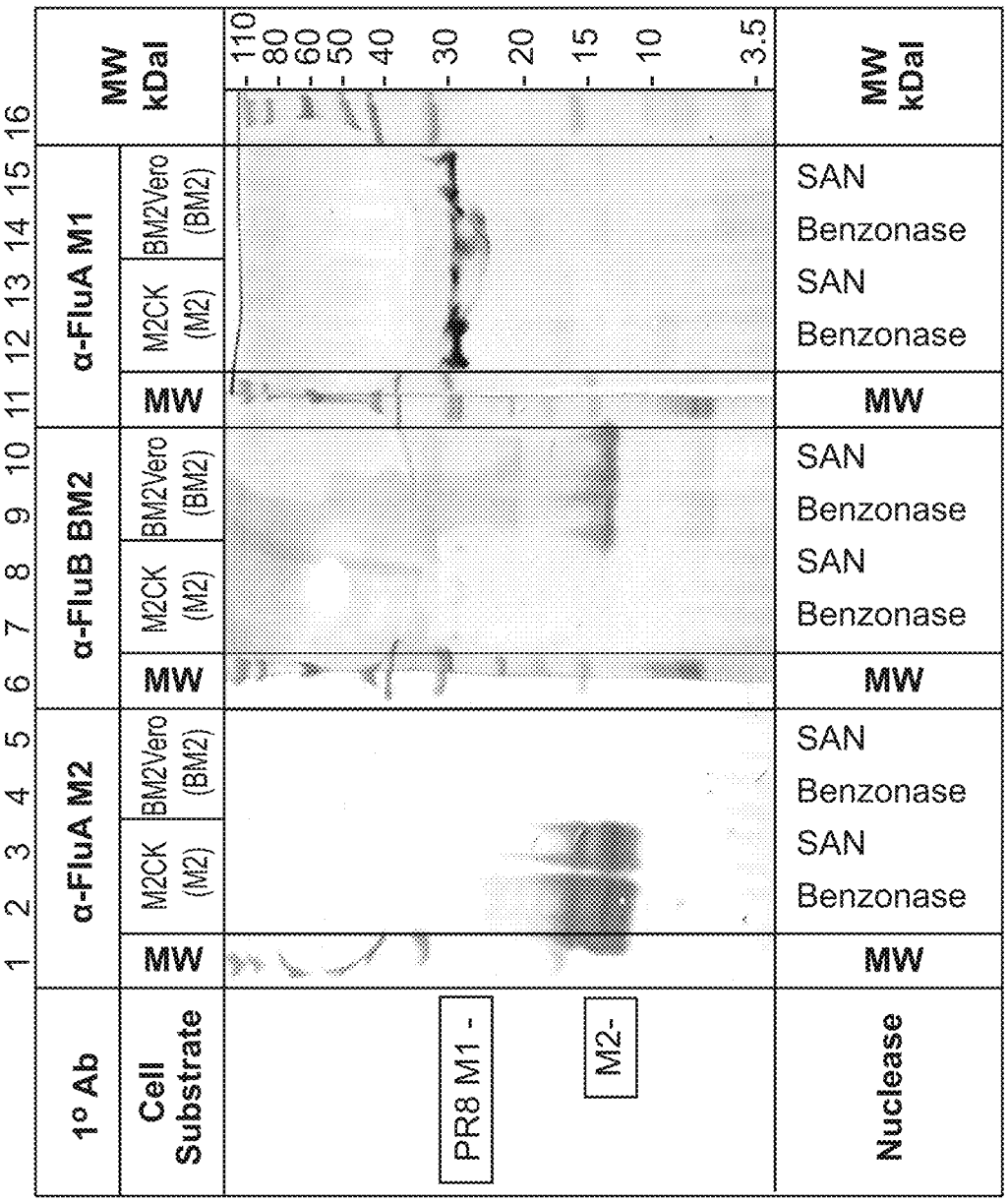
FIG. 15B is a Western blot showing the M2 protein content and identity of influenza A M2SR virus produced in M2-expressing M2CK and BM2-expressing BM2 Vero cell substrates.

To demonstrate this, influenza A M2SR Brisbane/10/2008 (H3N2) virus was passaged in influenza A M2-expressing M2CK cells and chimeric M2SR Brisbane/10/2008 (H3N2) was passaged 3 times in influenza B BM2-expressing BM2Vero cells in MEM media containing 0.3% BSA. Culture supernatant was clarified by centrifugation. Clarified culture media was treated with Benzonase (Novagen EMD, Merck KGaA, Darmstadt, Germany) or SAN (Articzymes, Tromso, Norway) nuclease to reduce viscosity by removing residual cell substrate DNA. Nuclease treated culture media was concentrated 60-fold using centrifugal concentrators with 100,000 nominal molecular weight cut-off regenerated cellulose membranes (Amicon, Merck KGaA, Darmstadt, Germany). Viral proteins in the supernatants were combined with LDS sample buffer (Thermo Fisher Scientific, Waltham, MA) and 5 mM TCEP and denatured by heating to 70° C. for 10 minutes. Proteins were separated in triplicate on a 4-12% denaturing Bis-Tris NuPAGE polyacrylamide gel (Thermo Fisher Scientific, Waltham, MA) in MES buffer and transferred to three PVDF membranes. Pre-stained protein molecular weight standards were run for size comparison. Membranes were blocked in 1% (w/v) non-fat dry milk and incubated with three different primary and antibody pairs. The first membrane was incubated with influenza A virus M2 protein monoclonal mouse antiserum 14C2 (Santa Cruz Biotechnology, Dallas, TX) at a 2000:1 dilution, followed by secondary horseradish peroxidase-conjugated anti-mouse IgG (H+L) (SeraCare KPL, Milford, MA) at a 3000:1 dilution. The second membrane was incubated with influenza B virus BM2 protein polyclonal rabbit antiserum (Hatta-M, et al, J. Virol, 78(11): 5576-5583. 2004) at a 2000:1 dilution, followed by secondary horseradish peroxidase-conjugated anti-rabbit IgG (H+L) (SeraCare KPL, Milford, MA) at a 3000:1 dilution. The third membrane was incubated with influenza virus matrix protein polyclonal goat antiserum NR-3134 (BEI Resources, NIAID, NIH) at a 2000:1 dilution, followed by secondary horseradish peroxidase-conjugated anti-goat IgG (H+L) (SeraCare KPL, Milford, MA) at a 3000:1 dilution. Bands were visualized using TMB membrane peroxidase substrate (SeraCare KPL, Milford, MA). Monoclonal anti-M2 antibody detected M2 in the influenza A M2SR virus preparation, and no influenza A M2 protein was detected in the chimeric M2SR preparation. Conversely polyclonal anti-BM2 serum detected BM2 in the envelope of the chimeric virus and no BM2 was detected in the standard M2SR virus. Polyclonal anti-serum against M1 matrix protein detected the 28 kDal molecular weight PR8 M1 protein in both the M2SR and the chimeric M2SR viruses (FIG. 15B).

Example 14: Use of Individual BM2 Mutants as Vaccine

Figure 16A:
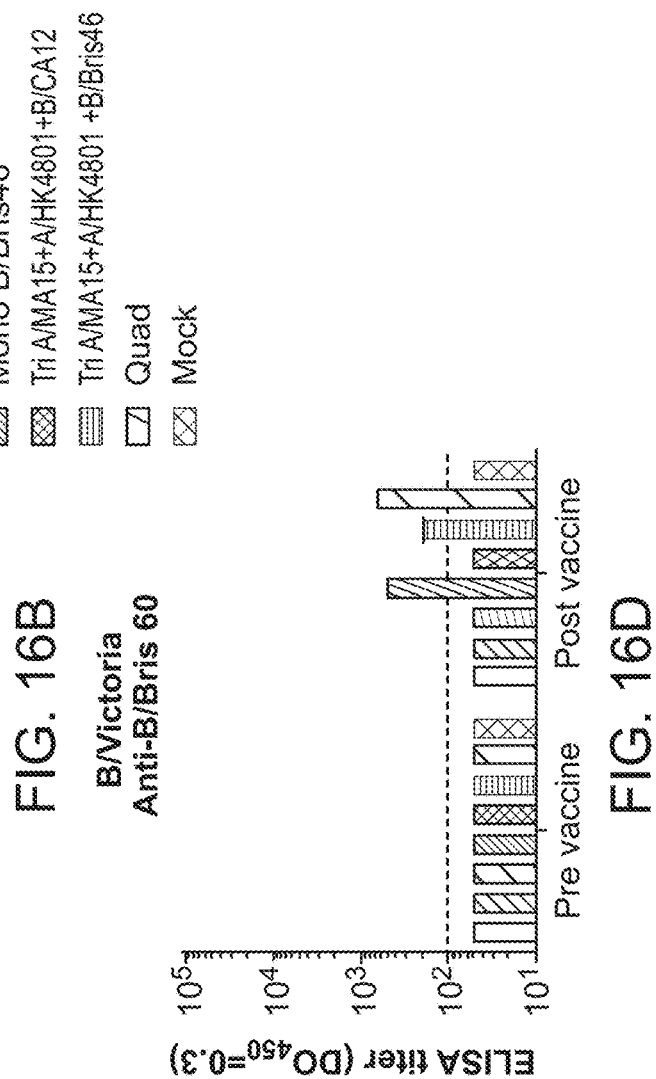
FIGS. 16A-16D are charts showing M2SR and BM2SR mutants elicit antibody responses against influenza A and influenza B viruses in multivalent formulations. Representative M2SR and BM2SR constructs. A/MA15 is H1N1 M2SR; A/HK4801 is H3N2 M2SR; B/CA12 is B Yamagata BM2SR-4; B/Bris46 is B Victoria BM2SR-4. The quadrivalent ("quad") formulation is a mix of all four. The trivalent ("tri") is a formulation of the indicated three viruses.
Figure 16B:
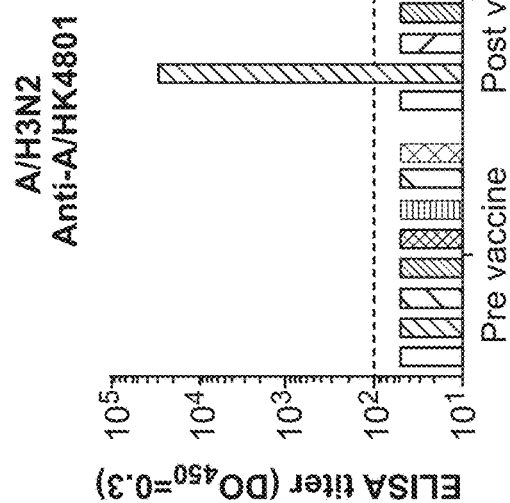
Figure 16C:
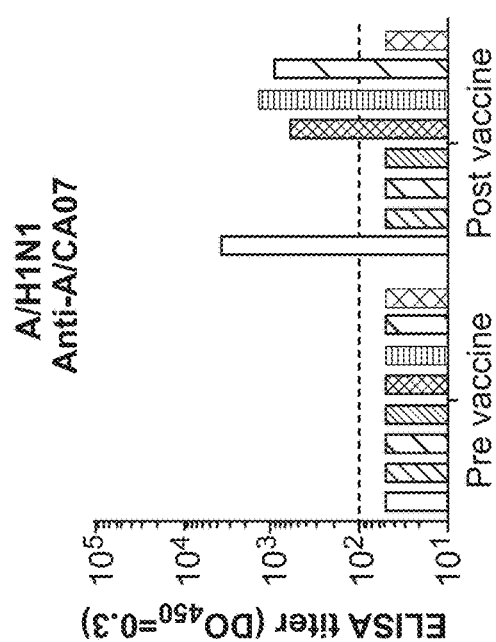
Figure 16D:
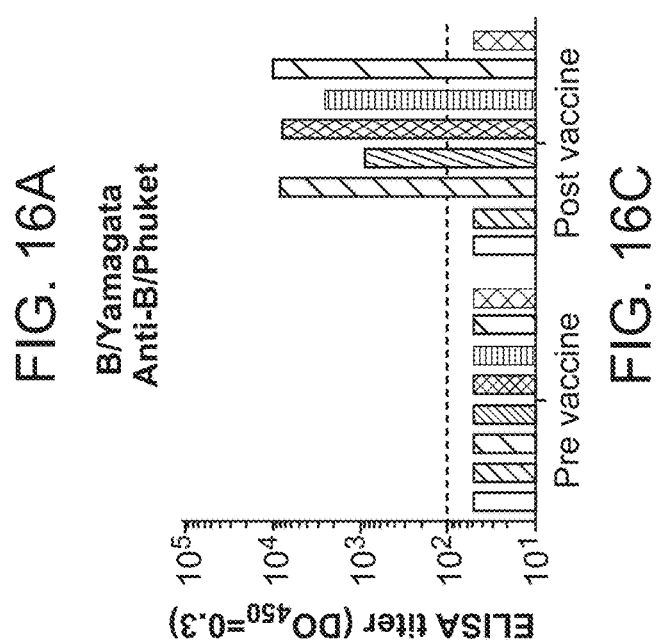

To test whether BM2 mutant viruses can elicit antibody responses in mice, BM2 mutant viruses (BM2SR-4 viruses representing B/Yamagata and B/Victoria lineages) were formulated either as a monovalent, trivalent, or quadrivalent vaccine with the influenza A H1N1 or H3N2 M2SR vaccines. Six-week-old BALB/c female mice were inoculated intranasally with monovalent, trivalent, or quadrivalent vaccines at doses ranging from $10^6$ to $10^7$ TCID50/mouse. A control group of mice were given PBS. Serum samples were taken on day 14 after prime inoculation. Anti-HA IgG antibody titers from the serum samples were determined by enzyme-linked immunosorbent assay (ELISA) against antigens representing B/Victoria lineage and B/Yamagata lineage. Additionally, anti-HA IgG antibody titers from the serum samples were determined by enzyme-linked immunosorbent assay (ELISA) against the influenza A H1N1 and H3N2 antigens (FIGS. 16A and 16B). Both BM2SR vaccine components (representing B/Victoria lineage and B/Yamagata lineage) elevated anti-influenza virus antibodies higher than the control PBS group against influenza B antigens representing the two influenza B lineages in multivalent formulations (FIGS. 16C and 16D). These results demonstrate that BM2SR vaccines generate antibody responses against the intended HA and that there is no interference between the monovalent components when formulated into multivalent vaccines. Immune responses are generated to each monovalent component in the multivalent formulations.

Figure 16E:
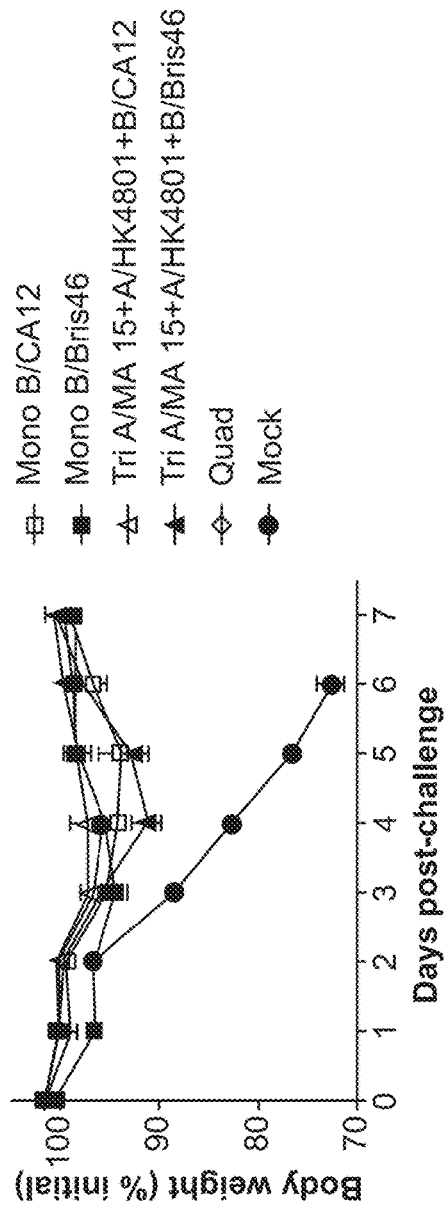
FIGS. 16E-16F are charts showing mouse body weight change and survival, respectively, after a lethal dose influenza B challenge, post-inoculation with monovalent BM2SR, trivalent, and quadrivalent formulations.
Figure 16F:
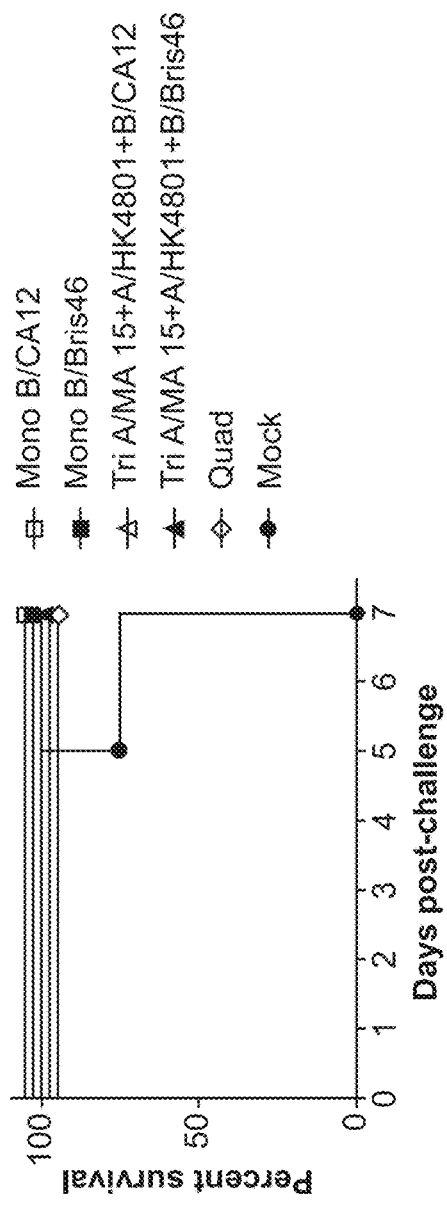

To show that BM2SR mutants protect mice from lethal influenza B virus challenge as monovalent, trivalent or quadrivalent formulations, BALB/c female mice (N=4) were challenged with a lethal dose of a heterosubtypic influenza B virus, such as B/Malaysia/2706/2004 virus (20 mouse 50% lethal dose ($MLD_{50}$)), 22 days after the inoculation. All mice vaccinated with the BM2SR, trivalent, and quadrivalent vaccines survived the challenge and lost no weight (FIGS. 16E and 16F). The control mice that were given only PBS, however, lost body weight and did not survive 7 days past the challenge date. These results indicate that the BM2SR viruses protect against influenza B virus challenge even when the virus does not match the vaccine component. The protection is provided by BM2SR viruses in multivalent formulations as well as monovalent formulations.

Example 15: Immune Responses Elicited by BM2SR in Monovalent and Quadrivalent Vaccine Formulations and Protective Efficacy in the Ferret Model A. Summary This example demonstrates that BM2SR vaccine can elicit immune responses in the ferret model both in a monovalent or multivalent formulation. That is, the protective immune responses elicited by BM2SR is not subject to interference from other vaccine components when formulated as a quadrivalent nor does BM2SR interfere with the immune responses of the other components (i.e., does not dominate the immune response). The BM2SR candidate viruses were administered intranasally to 12 male ferrets at a dose level of $1 \times 10^7$ $TCID_{50}$ (monovalents) or $4 \times 10^7$ $TCID_{50}$ (quadrivalent). As a control, a group of ferrets was administered as a placebo control. A prime-boost vaccination regimen was utilized for each treatment group. Ferrets were administered the prime vaccine (Day 0) and the boost vaccination 28 days later (Day 28). Following each vaccination, ferrets were observed for 14 days post inoculation for mortality, with body weights, body temperatures, and clinical signs measured daily. Serum was collected on days 21, 35, and 56 from all ferrets post-vaccination to evaluate antibody levels overtime.

All animals were challenged intranasally on Day 70 with $1 \times 10^6$ PFU of influenza A virus, A/California/07/2009 (H1N1pdm). Following challenge, ferrets were monitored for 14 days post inoculation for mortality, with body weights, body temperatures, and clinical signs measured daily. Nasal washes were collected on days 1, 3, 5, and 7 post challenge from ferrets (N=8) in each group for viral titers. Additionally, serum was collected post-challenge (day 82) from surviving ferrets for analysis. Necropsy was performed on 4 ferrets per group 3 days (day 73) post challenge. Organs were collected for determination of viral load (titers) after challenge.

No vaccine related adverse events were observed among the 5 groups. After challenge, the placebo control group exhibited a reduction (~15%) in weight. A reduction in weight was also observed in the antigenically mismatched monovalent BM2SR vaccinated groups; however, the reduction (~5-8%) was less than that observed in the placebo group. The Quadrivalent M2SR did not display any significant weight loss after challenge.

B. Materials and Methods

Vaccine Virus Inoculation. Ferrets were inoculated intranasally with either two doses of a monovalent BM2SR vaccine at a dose of $1 \times 10^7$ $TCID_{50}$ or inoculated intranasally with two doses of a quadrivalent M2SR vaccine at a dose of $4 \times 10^7$ $TCID_{50}$ as shown in Table 9. A vial of frozen stock was thawed at room temperature for at least 10 minutes and then stored refrigerated (or on wet ice) until use. Ferrets were anesthetized with ketamine/xylazine and the virus dose administered intranasally in a volume of 500 µL (250 µL per nare). Animals were observed daily for 7 days after each vaccination. Body weights, body temperature and clinical signs were monitored for 7 days.

TABLE 9

Vaccination and sample collection schedule

| Group | Vaccine Virus | N | Dose $(TCID_{50})$[1] | Vaccination (days) | Challenge (day) | Nasal Washes[2] (days) | Organs[3] n = 3 (day) | Serum collections[4] |
|---|---|---|---|---|---|---|---|---|
| 1 | Vehicle (Control) | 12 | N/A | 0, 28 | 70 | 71, 73, 75, 77 | 73 | 21, 35, 56, 82 |
| 2 | B/Bris BM2SR | 12 | $10^7$ | 0, 28 | 70 | 71, 73, 75,77 | 73 | 21, 35,56, 82 |
| 3 | B/Wisc BM2SR | 12 | $10^7$ | 0, 28 | 70 | 71,73, 75,77 | 73 | 21, 35, 56, 82 |
| 4 | Quad M2SR | 12 | $4 \times 10^7$ | 0, 28 | 70 | 71,73, 75.77 | 73 | 21, 35, 56, 82 |

[1]Inoculated intranasally
[2]Nasal Washes collected from animals not assigned for necropsy
[3]Organs (nasal turbinate, trachea, lung (left and right cranial and caudal lobes)) collected from 4 ferrets per group for viral titer analysis.
[4]Post-vaccination serum collections The BM2SR virus is a recombinant influenza B virus that does not express a functional BM2 protein, comprising a BM2SR-0 mutant comprising SEQ ID NO: 11, encoding the HA and NA of B/Brisbane/60/2008 (Victoria) or B/Wisconsin/01/2010 (Yamagata). The Quadrivalent M2SR is composed of 2 M2SR and 2 BM2SR viruses that encode for H1N1, H3N2, B/Victoria, B/Yamagata HA and NA.

Animals and Animal Care. Male ferrets were purchased from Triple F Farms and 48 of the ferrets were placed on study. Animals were approximately 4 months of age at the time of study initiation. The animals were certified by the supplier to be healthy and free of antibodies to infectious diseases. Upon arrival, the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison WI) and city of Chicago tap water were provided ad libitum and were refreshed at least three time per week. Fluorescent lighting in the animal rooms was maintained on a 12-hr light/dark cycle. Animal room temperature and relative humidity were within respective protocol limits and ranged from 20.0 to 25.0° C. and 30 to 63%, respectively, during the study.

Animal Quarantine and Randomization. The ferrets were held in quarantine for seven days prior to randomization and observed daily. Based on daily observations indicating general good health of the animals the ferrets were released from quarantine for randomization and testing. Following quarantine, ferrets were weighed and assigned to treatment groups using a computerized randomization procedure based on body weights that produced similar group mean values. Within a group, all body weights were within 20% of their mean. Animals selected for the study receive a permanent identification number by ear tag and transponder and individual cage cards also identified the study animals by individual numbers and group. The identifying numbers assigned were unique within the study.

Experimental Design. To assess the vaccine immunogenicity and efficacy, ferrets were immunized with each BM2SR or Quadrivalent M2SR virus or mock immunized by placebo control. Ferret body weight, body temperature, and clinical symptoms were monitored and immunological responses evaluated. Forty-eight male ferrets (Triple F Farms, Sayre PA), 4 months of age at the time of study initiation were utilized for the study. All animal procedures were performed in an animal biosafety level-2 facility in accordance with the protocols approved by the animal care and use committee at HT Research Institute. Prior to inoculation, ferrets were monitored for 3 days to measure body weight and establish baseline body temperatures. Temperature readings were recorded daily through a transponder (BioMedic data systems, Seaford, DE) implanted subcutaneously in each ferret. Blood was collected prior to study initiation, and serum tested for influenza antibodies. Pre vaccination serum samples were treated with receptor destroying enzyme (RDE) to remove nonspecific inhibitors, then serially diluted, tested against a defined amount of influenza virus A/California/07/2009-like (H1N1pdm), A/Switzerland/9715293/2013 (H3N2), Influenza B Virus, B/Brisbane/60/2008 (Victoria Lineage) and B/Wisconsin/01/2010 (Yamagata Lineage) and mixed with 0.5% turkey red blood cells or 0.75-1.0% guinea pig red blood cells. Antibody titers are defined by the lowest serum dilution causing inhibition of red blood cell agglutination. Only ferrets with HAI (hemagglutination inhibition) titers less than 40 were considered seronegative and used in this study. Study animals were randomized and divided into 4 groups (12 ferrets/group) as shown in Table 9.

Ferrets were inoculated intranasally with a single dose of $1\times10^7$ TCID$_{50}$ of BM2SR virus on days 0 and 28 or a single dose of $4\times10^7$ TCID$_{50}$ of Quadrivalent M2SR on days 0 and 28. Control group was mock inoculated intranasally with a placebo control on days 0 and 28. Ferret body temperatures, weights, and clinical symptoms were monitored daily for 14 days post-inoculations. Nasal wash samples were kept at −65° C. Blood was collected prior to inoculation (day −3 to −5) and days 21, 35 and 56 and serum kept at −65° C. until measurement of antibody titer by ELISA and HAI assay.

C. Results

Anti-HA IgG antibody titers from the serum samples were determined by enzyme-linked immunosorbent assay (ELISA) against A/Brisbane/10/2007 (H3N2), A/California/07/2009 (H1N1pdm), B/Wisconsin/01/2010 (Yamagata lineage), and B/Brisbane/60/2008 (Victoria lineage). Briefly, ELISA plates were coated by recombinant HA protein from each strain, blocked by bovine serum albumin (BSA), and samples were applied. Ferret IgG antibodies were detected by horseradish peroxidase labeled anti-ferret IgG-goat antibodies (KPL, Inc., Gaithersburg, MD) and SureBlue TMB (KPL, Inc.) substrate.

Figure 18:
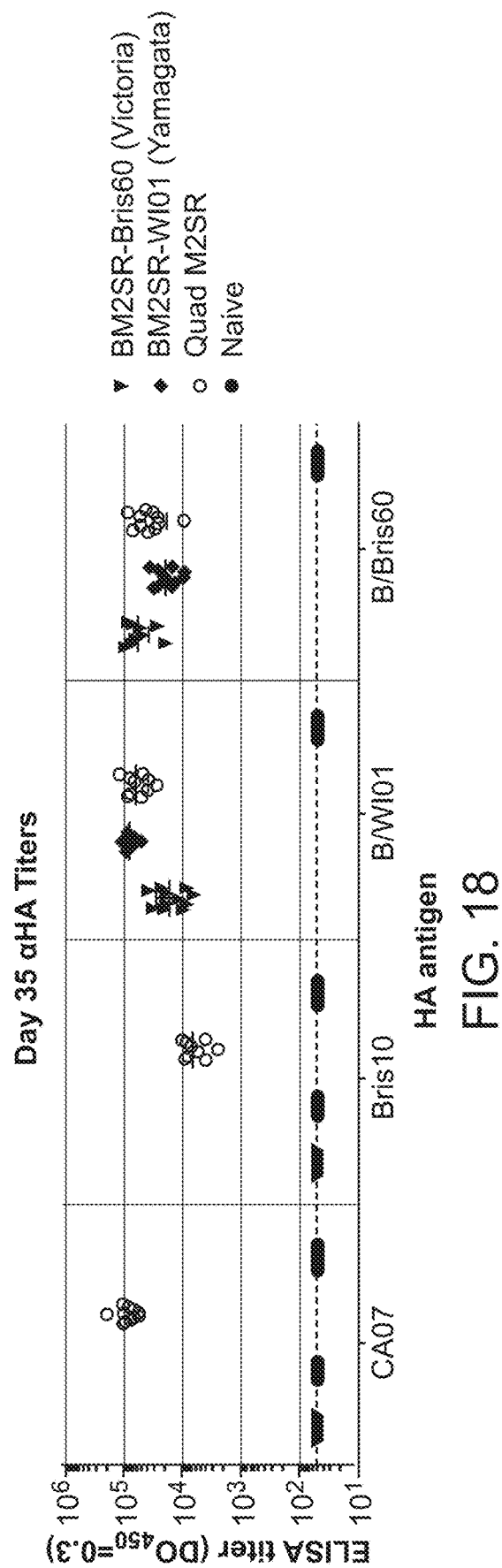
FIG. 18 is a chart showing enzyme-linked immunosorbent assay (ELISA) titers elicited against influenza A and B antigens in BM2SR and quadrivalent vaccines.

As expected, ferrets in each of the immunized groups showed significant elevation of anti-HA antibody in serum to its respective antigen. Serum from the BM2SR immunized groups demonstrated the expected specificity and did not react against the influenza A antigens (CA07-H1N1, Bris10-H3N2). More importantly, the Quadrivalent M2SR groups demonstrated significant elevation of anti-HA antibody in serum against all four antigens (FIG. 18) indicating that BM2SR is immunogenic when formulated as a quadrivalent vaccine and that there is no interference between the components of the multivalent formulation. These data suggest that the BM2SR and Quadrivalent M2SR viruses elicit significant immune responses in ferrets.

Serum samples were analyzed by Hemagglutination Inhibition (HAI) assay to demonstrate functional activity of the antibodies detected by ELISA. Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2), A/California/07/2009 (H1N1pdm), B/Wisconsin/01/2010 (Yamagata lineage) and B/Brisbane/60/2008 (Victoria lineage) influenza viruses. After incubation, 0.5% avian red blood cells were added to each sample and incubated for 30±5 minutes. Presence or absence of hemagglutination was then scored.

Figure 19:
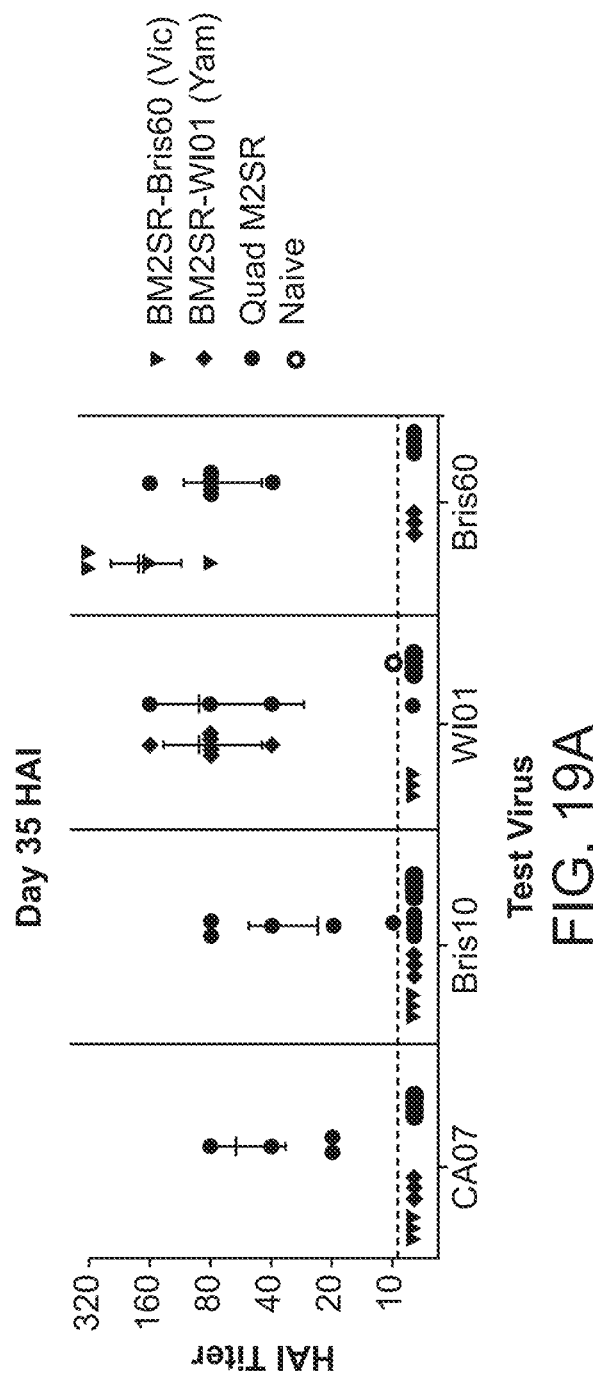
FIG. 19A is a chart showing hemagglutination inhibition (HAI) titers elicited against influenza A and B antigens in BM2SR and quadrivalent vaccines.
FIG. 19B is a table showing HAI titers elicited against BM2SR and quadrivalent vaccines in pooled sera at day 35 post inoculation.

As shown in FIGS. 19A and 19B, all immunized ferrets demonstrated significant HAI antibody titers against their respective test virus. The Quadrivalent M2SR demonstrated significant HAI titers against all four test viruses. The placebo (naïve) group did not elicit any influenza specific antibodies. The CDC states that serum HAI antibody titers of 40 are associated with at least a 50% reduction in risk for influenza infection or disease in populations. Therefore, these results suggest that BM2SR viruses elicit protective immune responses that are maintained when the viruses formulated as a Quadrivalent vaccine with influenza A M2SR viruses.

After challenge with A/California/09/2009 (H1N1pdm), a 5-8% loss of body weight was observed by Day 6 post challenge in the BM2SR immunized animals. Control ferrets (placebo group) lost the most weight (15%). Weight loss among vaccinated ferrets was dependent on the antigenicity of the vaccine. Ferrets receiving the Quadrivalent M2SR (that contains the H1N1pdm M2SR) did not display any significant weight loss. Ferrets receiving either of the BM2SR vaccines displayed ~5-8% weight loss.

Figure 20:
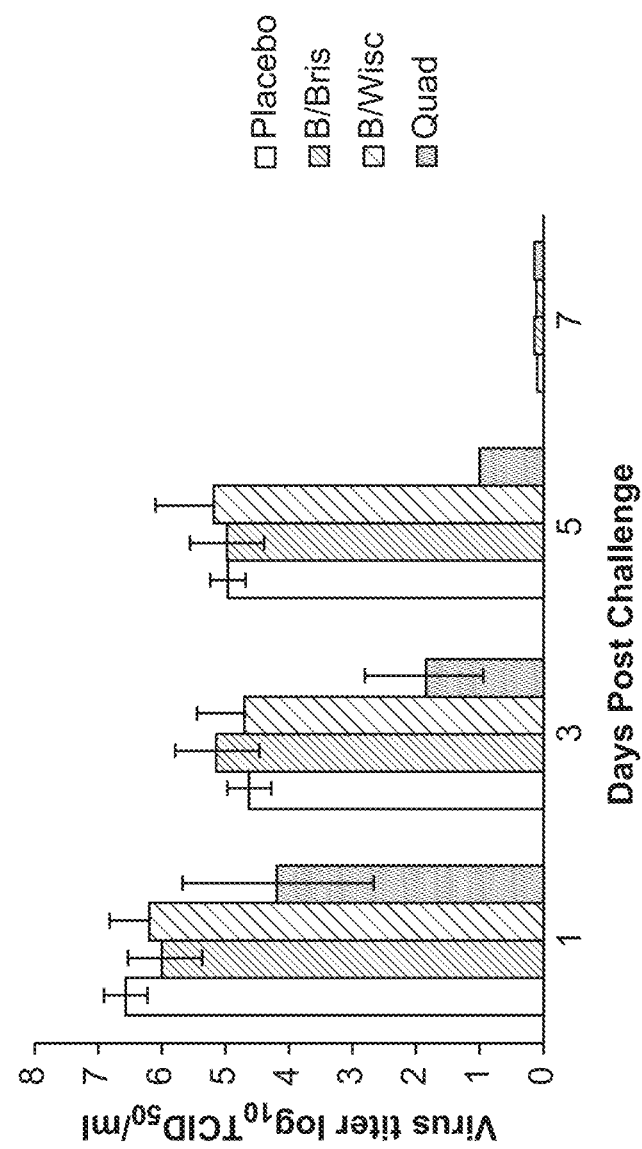
FIG. 20 is a chart showing nasal wash virus titers on days 1, 3, 5, and 7 post influenza A challenge.

Nasal wash samples were collected from all ferrets on days 1, 3, 5, and 7 post-challenge and evaluated for the presence of challenge virus by plaque assay in MDCK cells. FIG. 20 shows that the Quadrivalent M2SR controlled challenge virus replication. The placebo and BM2SR monovalent vaccines did not control the challenge virus with at least 5 logs of virus being detected up to 5 days post-infection. The BM2SR vaccine did not control the influenza A challenge virus but did have a tempering effect on disease progression as evidenced by less weight loss than the placebo group (data not shown).

Figure 21A:
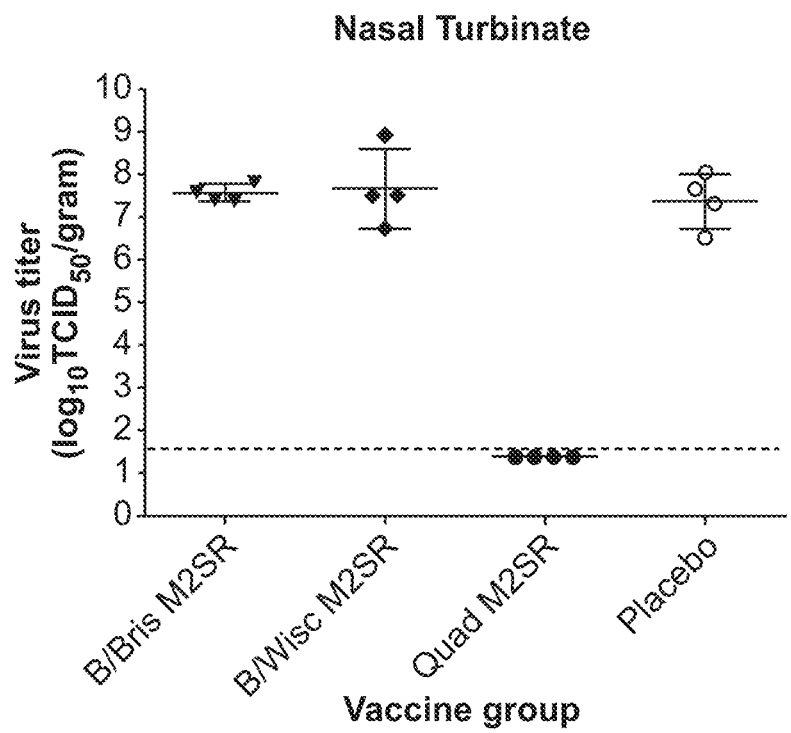
FIG. 21A is a chart showing virus titer in nasal turbinate tissue on day 3 post influenza A challenge.
Figure 21B:
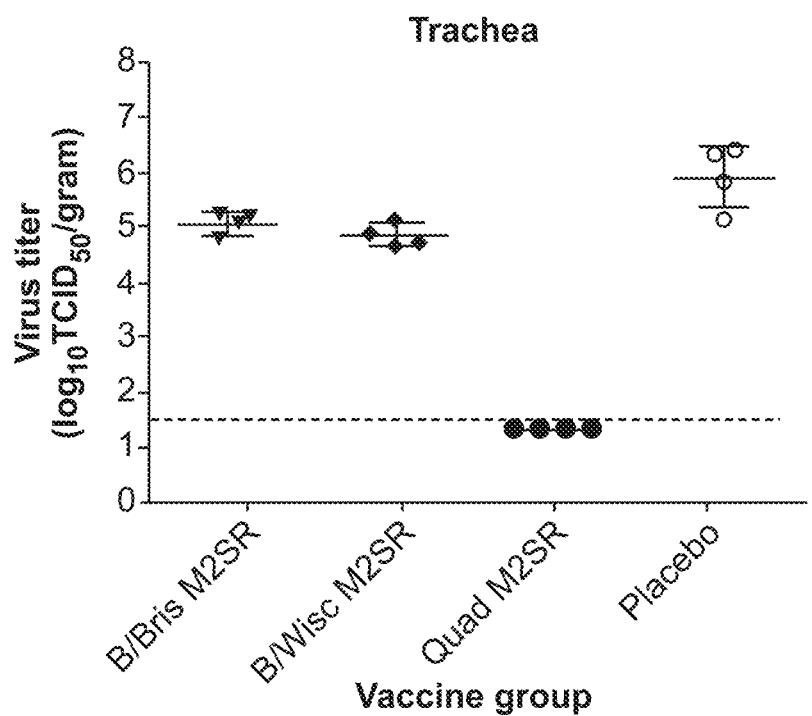
FIG. 21B is a chart showing virus titer in trachea tissue on day 3 post influenza A challenge.
Figure 21C:
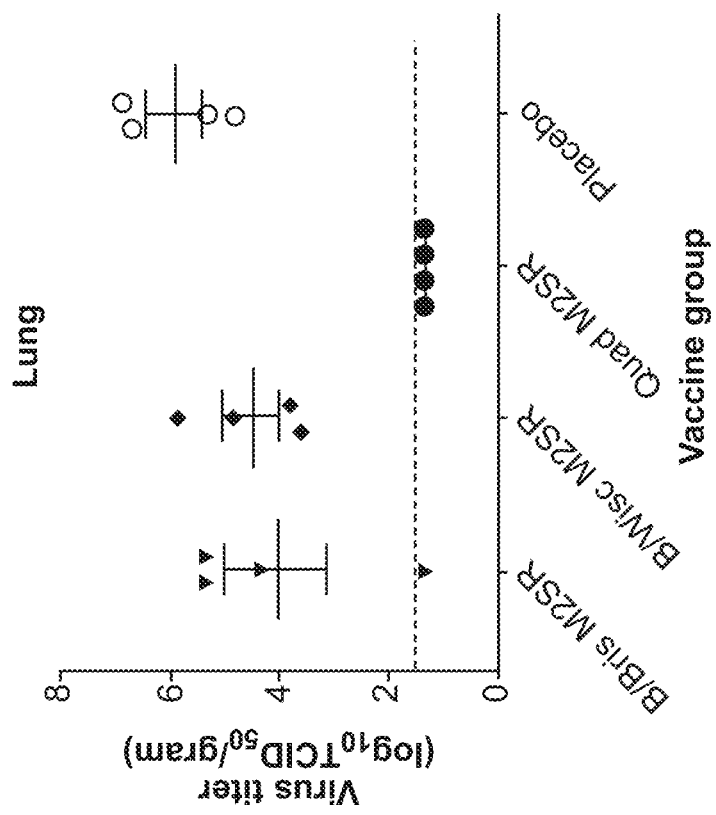
FIG. 21C is a chart showing virus titer in lung tissue on day 3 post influenza A challenge.

Respiratory organs harvested on day 3 post-infection further from 4 ferrets demonstrated the control of challenge virus. The Quad M2SR did not allow the challenge virus to replicate in the upper and lower respiratory tissues (e.g., nasal turbinate, trachea, and lung tissues) at all as shown in FIGS. 21A, 21B, and 21C. In contrast, the challenge virus grew to high titers in the upper respiratory tissues (nasal turbinate and trachea) of the other groups. In the lower respiratory tract (lung), the monovalent BM2SR vaccines controlled the challenge virus relative to the placebo group. These results suggest that the Quadrivalent M2SR prevented influenza infection from establishing itself and that the BM2SR vaccines reduced severity of infection.

D. Conclusion

This example shows that intranasal administration of the BM2SR and Quadrivalent M2SR vaccine virus to ferrets was not associated with any vaccine related adverse events (e.g., elevated body temperature, loss of weight, or clinical signs) and is useful as an intranasal influenza vaccine. These results show that the BM2SR elicits immune responses in ferrets and when formulated into a Quadrivalent M2SR virus elicits protective immune responses against each strain contained in the multivalent formulation.

Example 16: Influenza AOF Growth in Vero Cells

Virus Generation. M2SR and BM2SR-4 viruses were generated as previously described. For M2SR, influenza A viral RNA segments 1, 2, 3, 5, 8 and M2SR segment 7 from influenza A/Puerto Rico/1934 and the HA and NA viral RNA segments 4, 6 of influenza A/Hong Kong/4801/2014 (H3N2) were used. For BM2SR, influenza B viral RNA segments 1, 2, 3, 5, 8 from influenza B/Yamagata/1973 and segment 7 BM2SR-4 from B/Florida/2006 and the HA and NA viral RNA segments 4, 6 of influenza B/California/12/2015 (Yamagata Lineage) were used. Influenza cDNAs were cloned into a RNA Polymerase I expression cassette. Resulting plasmids were transfected along with viral polymerase, NP and M2 protein expression plasmids into BM2Vero cells and viruses released into supernatant were amplified in BM2Vero cells.

Cell and Virus Culture. Madin-Darby Canine Kidney (MDCK) cells were maintained in MEM, supplemented with 10% Fetal Bovine Serum (FBS). M2CK and BM2CK cells, MDCK cell lines that stably express the influenza A M2 and BM2 proteins, respectively, were maintained in MEM, supplemented with 10% FBS and 150 µg/mL Hygromycin B at 37° C., 5% $CO_2$. Vero (African green monkey kidney) cells were grown in either MEM, supplemented with 10% Fetal Bovine Serum (FBS) or OptiVero, an animal-origin-free (AOF) media formulated according to manufacturer recommendations (Invitria, Fort Collins, C). M2VeroA and BM2Vero cells, Vero cell lines that stably express the influenza A M2 and the influenza B BM2 proteins, respectively, were maintained in OptiVero medium, supplemented with 500 or 1000 microgram per mL G418 sulfate.

Wild-type influenza A/Hong Kong/4801/2014 (H3N2) was grown in MDCK cells and wild-type influenza B/CA/12/2015 was grown in Vero cells in MEM supplemented with 0.3% Bovine Serum Albumin (BSA) and 1 microgram per mL Trypsin-TPCK. M2SR and BM2SR-4 virus were grown in M2VeroA or BM2Vero cells using OptiVero media and 1 microgram per mL T-TPCK.

Figure 22A:
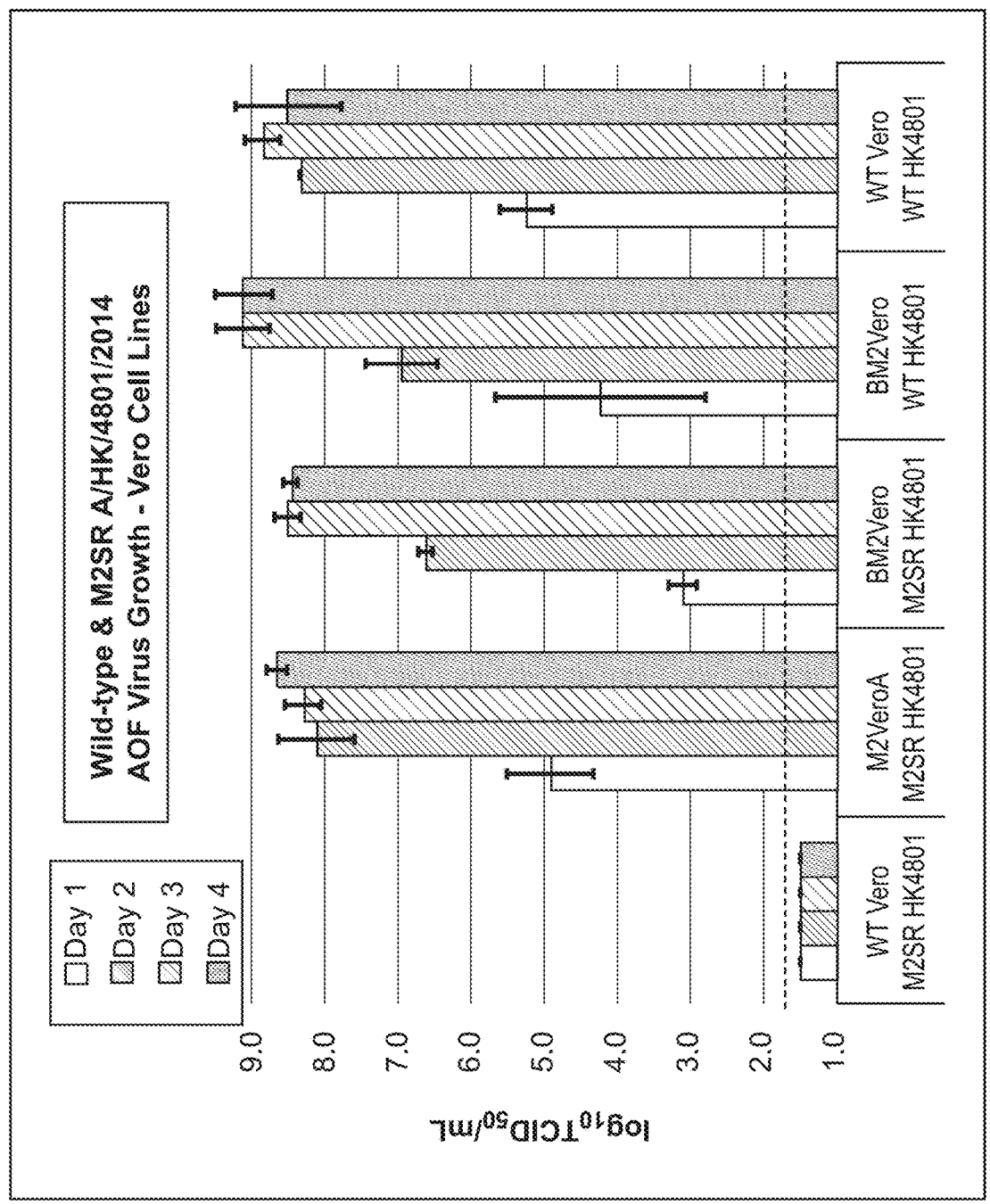
FIG. 22A is a chart showing the results of wild-type influenza A/Hong Kong/2014 (H3N2) and M2SR A/Hong Kong/2014 (H3N2) virus infection of Vero (WT Vero), M2-expressing Vero (M2VeroA), and BM2-expressing (BM2Vero) Vero cell lines at MOI of 0.001. Aliquots of culture supernatant were withdrawn at time points (t=1, 2, 3, 4 Days) after inoculation and were frozen. Aliquots were tested for viral replication by $TCID_{50}$ assay in M2CK cells. Samples with no detectable replication are plotted as $\log_{10} TCID_{50}=1.50$. Assay limit of detection $\log_{10} TCID_{50}=1.67$ shown as dotted line.

To directly compare viral growth kinetics, virus growth curves were performed using identical AOF culture conditions for each virus/cell line combination as follows. Vero, M2VeroA, or BM2Vero cells in exponential phase growth were plated at 1,000,000 cells per 60 mm tissue culture dish in AOF medium. After 24 hours culture in humidified incubator at 37° C. 5% $CO_2$, Vero cell lines were infected in triplicate in AOF media with the test virus at multiplicity of infection (MOI) of 0.001 $TCID_{50}$ unit per cell. After 120 minutes incubation at 35° C., 5% $CO_2$, the viral inoculum was removed and fresh AOF medium containing 1 microgram per mL Trypsin-TPCK was applied to the cells. Virus culture was performed in humidified incubator at 35° C., 5% $CO_2$. Every 24-hours, for 4 days, aliquots from the virus cultures were removed and stored frozen at −80° C. for later titration analyses. Viral titer of culture supernatant was determined by 50% tissue culture inhibitory dose ($TCID_{50}$) assay using supportive M2CK cells for M2SR virus and BM2CK cells for BM2SR4 virus samples. Wild-type virus samples were titrated on MDCK, or on M2-expressing M2CK and BM2CK cells. No viral titer was detected above assay limit of detection ($\log_{10} TCID_{50}$ per mL=1.67) for M2-deficient M2SR (FIG. 22A) or for BM2-deficient BM2SR4 virus cultures in wild-type Vero cells (FIG. 22B). The influenza A M2SR HK4801 well in cognate M2VeroA cells and the influenza B BM2SR4 CA12 virus replicated in BM2Vero cells with growth curves that are comparable to wild-type A/Hong Kong/2014 (H3N2) and B/CA/12/2015 respectively in wild-type Vero cells. The over-expression of M2 or BM2 had no effect on wild-type influenza A or B viral replication as compared to replication in the unmodified wild-type Vero cell line.

No viral replication was observed for BM2SR-4 influenza B virus grown in M2VeroA cell line (FIG. 22B). By contrast, the influenza A M2SR virus did replicate in the BM2Vero cells with kinetics very similar to that seen for influenza A M2SR growth in M2VeroA cells (FIG. 22A). Thus, expression of influenza BM2 protein in the BM2Vero cell line allows replication of influenza A M2-deficient M2SR virus strains, that is comparable to the growth kinetics of wild-type influenza A. Meanwhile, influenza A M2 does not substitute for the function of BM2 in replication of influenza B.

Example 17: Influenza a M2SR Genetic Stability in BM2Vero Cell Substrate

Virus Generation. Influenza A M2SR virus was generated using plasmid-based reverse genetics in M2VeroA cells. The influenza A viral RNA segments 1, 2, 3, 5, 8, and M2SR segment 7 from influenza A/Puerto Rico/1934 and the HA and NA viral RNA segments 4, 6 of influenza A/Hong Kong/4801/2014 (H3N2) were used to generate a M2SR HK4801 virus.

Influenza segment cDNAs were cloned into a unidirectional RNA Polymerase I expression cassette. Resulting 8 RNA-expression plasmids were co-transfected into M2VeroA cells along with 5 protein-expression plasmids including 3 viral polymerase plasmids, an NP plasmid and an M2 plasmid. Viruses released into supernatant were amplified in fresh M2Vero cells for 3 viral passages. After 3 passages, viral titer was determined, and genetic identity was confirmed by sequencing the entire strain genome.

Briefly, influenza A specific cDNA reaction products were amplified using influenza A specific PCR primers. The amplified products from all 8 segments were subjected to dye-terminator sequencing using segment-specific internal primers. The influenza A M2SR HK4801 virus was then passaged 10 additional rounds in the BM2-protein-expressing BM2Vero cell line. The M2VeroA P3/BM2Vero P10 virus strain, which had been passaged for a total of 13 passages in Vero cell lines, was again tested for genetic identity by determination of the complete genomic nucleotide sequence. The nucleotide sequence obtained from the genome of the M2SR HK4801 M2VeroA P3 virus strain generated by reverse genetics indicated that all eight virus segment sequences are identical to that of the starting cDNA plasmids. After 10 additional passages in culture in the BM2Vero cell line, the virus had undergone a very subtle adaptation. A total of four nucleotide substitutions were observed between the two strains. All the observed changes were silent mutations, meaning none of the observed substitutions are predicted to alter the amino acid coding of the adapted segment (Table 10). Accordingly, these results demonstrate that, first, the M2SR HK4801 virus generated by reverse genetics in Vero cells is genetically stable as only 4 base substitutions were observed in the 13,588 base influenza A gRNA genome after thirteen total rounds of viral amplification in Vero cell lines. Second, the BM2Vero cell line that expresses BM2 protein provides all needed functions of influenza A M2 and does not appear to exert any undue selection upon the influenza A M2SR virus as the genomic sequence remained stable after 10 viral passages supported only by BM2 protein.

TABLE 10

Genomic Nucleotide Sequence of M2SR HK4801 After Vero Passage

| | | Nucleotide Sequence Results | |
| --- | --- | --- | --- |
| Seg. | Gene | M2VeroA P3 | M2VeroA P3/ BM2Vero P10 |
| 1 | PB2 | Matches plasmid | 2 silent mutations |
| 2 | PB1 | Matches plasmid | Matches plasmid |
| 3 | PA | Matches plasmid | 1 silent mutations |
| 4 | HA | Matches plasmid | 1 silent mutations |
| 5 | NP | Matches plasmid | Matches plasmid |
| 6 | NA | Matches plasmid | Matches plasmid |
| 7 | M | Matches plasmid | Matches plasmid |
| 8 | NS | Matches plasmid | Matches plasmid |

What is claimed is:

1. A recombinant influenza A virus comprising a mutant BM2 protein encoded by a sequence selected from the group consisting of SEQ ID NO: 27, SEQ ID NO: 28, SEQ ID NO: 29, SEQ ID NO: 30, SEQ ID NO: 31, and SEQ ID NO: 32.

2. A host cell for propagating a recombinant influenza virus, wherein the host cell is a Vero cell expressing a sequence selected from the group consisting of SEQ ID NO: 27, SEQ ID NO: 28, SEQ ID NO: 29, SEQ ID NO: 30, SEQ ID NO: 31, and SEQ ID NO: 32.

3. The host cell of claim 2, wherein the recombinant influenza virus is an influenza A virus.

4. The host cell of claim 3, wherein the influenza A virus comprises a mutant M2 gene as set forth in SEQ ID NO: 33.

5. The host cell of claim 2, wherein the recombinant influenza virus is an influenza B virus.

6. The host cell of claim 5, wherein the influenza B virus comprises a mutant BM2 gene as set forth in SEQ ID NO: 4 or SEQ ID NO: 6.

7. The host cell of claim 6, wherein the host cell expresses SEQ ID NO: 27.

* * * * *